(12) United States Patent
Bayever et al.

(10) Patent No.: US 9,717,724 B2
(45) Date of Patent: *Aug. 1, 2017

(54) METHODS FOR TREATING PANCREATIC CANCER USING COMBINATION THERAPIES

(71) Applicant: IPSEN BIOPHARM LTD., Wrexham (GB)

(72) Inventors: Eliel Bayever, New York, NY (US); Navreet Dhindsa, Boston, MA (US); Jonathan Basil Fitzgerald, Arlington, MA (US); Peter Laivins, Scituate, MA (US); Victor Moyo, Ringoes, NJ (US); Clet Niyikiza, Gulph Mills, PA (US); Jaeyeon Kim, Lexington, MA (US)

(73) Assignee: Ipsen Biopharm Ltd., Wrexham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/241,128

(22) Filed: Aug. 19, 2016

(65) Prior Publication Data

US 2016/0375004 A1 Dec. 29, 2016

Related U.S. Application Data

(63) Continuation-in-part of application No. 14/406,776, filed as application No. PCT/US2013/045495 on Jun. 12, 2013, now Pat. No. 9,452,162.

(60) Provisional application No. 61/784,382, filed on Mar. 14, 2013, provisional application No. 61/659,211, filed on Jun. 13, 2012.

(51) Int. Cl.
| | | |
|---|---|---|
| *A01N 43/00* | (2006.01) |
| *A61K 31/33* | (2006.01) |
| *A61K 38/00* | (2006.01) |
| *A61P 35/00* | (2006.01) |
| *A61K 31/4745* | (2006.01) |
| *A61K 31/573* | (2006.01) |
| *A61K 45/06* | (2006.01) |
| *A61K 31/513* | (2006.01) |
| *A61K 31/517* | (2006.01) |
| *A61K 9/00* | (2006.01) |
| *A61K 9/127* | (2006.01) |
| *A61K 31/519* | (2006.01) |
| *A61K 47/28* | (2006.01) |
| *A61K 47/24* | (2006.01) |
| *A61K 47/26* | (2006.01) |

(52) U.S. Cl.
CPC ........ *A61K 31/4745* (2013.01); *A61K 9/0019* (2013.01); *A61K 9/127* (2013.01); *A61K 9/1271* (2013.01); *A61K 31/513* (2013.01); *A61K 31/519* (2013.01); *A61K 47/24* (2013.01); *A61K 47/26* (2013.01); *A61K 47/28* (2013.01)

(58) Field of Classification Search
None
See application file for complete search history.

(56) References Cited

U.S. PATENT DOCUMENTS

| | | |
|---|---|---|
| 4,604,463 A | 8/1986 | Miyasaka et al. |
| 5,013,556 A | 5/1991 | Woodle et al. |
| 5,077,056 A | 12/1991 | Bally et al. |
| 5,192,549 A | 3/1993 | Barenolz et al. |
| 5,316,771 A | 5/1994 | Barenholz et al. |
| 5,538,954 A | 7/1996 | Koch et al. |
| 5,593,622 A | 1/1997 | Yoshioka et al. |
| 5,676,971 A | 10/1997 | Yoshioka et al. |
| 5,783,568 A | 7/1998 | Schlessinger et al. |
| 5,785,987 A | 7/1998 | Hope et al. |
| 5,846,458 A | 12/1998 | Yoshioka et al. |
| 6,110,491 A | 8/2000 | Kirpotin |
| 6,241,999 B1 | 6/2001 | Ye et al. |
| 6,355,268 B1 | 3/2002 | Slater et al. |
| 6,403,569 B1 | 6/2002 | Achterrath |
| 6,465,008 B1 | 10/2002 | Slater et al. |
| 6,720,001 B2 | 4/2004 | Chen et al. |
| 6,794,370 B2 | 9/2004 | Achterrath |
| 7,060,828 B2 | 6/2006 | Madden et al. |
| 7,829,113 B2 | 11/2010 | Okada et al. |
| 7,846,473 B2 | 12/2010 | Yoshino et al. |
| 8,067,432 B2 | 11/2011 | Anderson et al. |
| 8,147,867 B2 | 4/2012 | Hong et al. |
| 8,329,213 B2 | 12/2012 | Hong et al. |
| 8,703,181 B2 | 4/2014 | Hong et al. |
| 8,992,970 B2 | 3/2015 | Hong et al. |
| 2002/0102298 A1 | 8/2002 | Needham |

(Continued)

FOREIGN PATENT DOCUMENTS

| | | |
|---|---|---|
| WO | WO 9728156 A1 | 8/1997 |
| WO | WO 03030684 A1 | 4/2003 |

(Continued)

OTHER PUBLICATIONS

Camptosar label (labeling revision Dec. 12, 2014). Retrieved from the internet: http://www.accessdata.fda.gov/drugsatfda_docs/label/2014/020571s048lbl.pdf.

(Continued)

*Primary Examiner* — Kortney L Klinkel
*Assistant Examiner* — Tori M Strong
(74) *Attorney, Agent, or Firm* — Honigman Miller Schwartz and Cohn LLP; Cynthia M. Bott; Jonathan P. O'Brien

(57) ABSTRACT

Provided are methods for treating pancreatic cancer in a patient by administering liposomal irinotecan (MM-398) alone or in combination with additional therapeutic agents. In one embodiment, the liposomal irinotecan (MM-398) is co-administered with 5-fluorouracil and leucovorin.

24 Claims, 34 Drawing Sheets

(56) References Cited

U.S. PATENT DOCUMENTS

| | | |
|---|---|---|
| 2002/0146450 A1 | 10/2002 | Slater et al. |
| 2002/0192275 A1 | 12/2002 | Zalipsky et al. |
| 2003/0138481 A1 | 7/2003 | Zadi |
| 2015/0182460 A1 | 7/2015 | Hong et al. |

FOREIGN PATENT DOCUMENTS

| | | |
|---|---|---|
| WO | WO 03030864 A1 | 4/2003 |
| WO | WO 2005107712 A1 | 11/2005 |

OTHER PUBLICATIONS

Camptosar label (labeling revision May 14, 2010). Retrieved from the internet: http://www.accessdata.fda.gov/drugsatfda_docs/label/2010/020571s031s032s033s036s037lbl.pdf.

Non-Final Rejection of U.S. Appl. No. 14/175,365 (U.S. Pat. No. 8,992,970), dated Jun. 26, 2014, and Notice of References Cited, dated Jun. 26, 2014.

Final Rejection of U.S. Appl. No. 11/121,294 (U.S. Pat. No. 8,147,867), dated Nov. 23, 2011, and Notice of References Cited, dated Nov. 23, 2011.

Katsu, T., et al., "Ion-Selective Electrode for Transmembrane pH Difference Measurements," Anal. Chem., vol. 73, 2001, pp. 1849-1854.

Chou, T., et al., "Effect of Composition on the Stability of Liposomal Irinotecan Prepared by a pH Gradient Method," Journal of Bioscience and Bioengineering, vol. 95 No. 4, 2003, pp. 405-408.

Author Unknown, "From Antinutrient to Phytonutrient: phytic acid gains respect," HighBeam Research, Environmental Nutrition, Apr. 1, 2004, 2 printed pages. URL: http://www.highbeam.com/doc/1G1-116341390.html/print (accessed Nov. 4, 2011).

Non-Final Rejection of U.S. Appl. No. 11/121,294 (U.S. Pat. No. 8,147,867), dated Apr. 13, 2011, and Notice of References Cited, dated Apr. 13, 2011.

Miles, David, et al., "Combination Versus Sequential Single-Agent Therapy in Metastatic Breast Cancer," The Oncologist, 7(suppl 6), 2002, pp. 13-19.

Maddison, J.E., SW Page, D Church. "Small Animal Clinical Pharmacology," (2002), p. 474.

Nentwich, Phyllis F., "Intravenous Therapy," (1990), p. 310.

Hong, K., "Anti-HER2 Immunoliposomes for Targeted Drug Delivery," Annals New York Academy of Sciences, vol. 886, Dec. 1999, pp. 293-296.

Sadzuka, Yasuyuki, et al, "Effect of Liposomalization on the Antitumor Activity, Side-Effects, and Tissue Distribution of CPT-11," Cancer Letters 127 (1998), pp. 99-106.

Shimada, Shinya, et al., "Irinotecan Plus Low-Dose Cisplatin for Alpha-Fetoprotein-Producing Gastric Carcinoma with Multiple Liver Metastases: Report of Two Cases," Surgery Today (2002) 32, pp. 1075-1080.

Ahmad, Imran, et al., "Antibody-Targeted Delivery of Doxorubicin Entrapped in Sterically Stabilized Liposomes Can Eradicate Lung Cancer in Mice," Cancer Research 53, Apr. 1, 1993, pp. 1484-1488.

Lee, Chun Man, et al. "Novel Chondroitin Sulfate-binding Cationic Liposomes Loaded with Cisplatin Efficiently Suppress the Local Growth and Liver Metastasis of Tumor Cells in Vivo." Cancer Research 62, Aug. 1, 2002, pp. 4282-4288.

Yeh, Brian K., et al. "Structural Basis for Activation of Fibroblast Growth Factor Signaling by Sucrose Octasulfate," Molecular and Cellular Biology, vol. 22, No. 20, Oct. 2002, pp. 7184-7192.

Non-Final Rejection of U.S. Appl. No. 13/654,373 (U.S. Pat. No. 8,703,181), dated Aug. 12, 2013, and Notice of References Cited, dated Aug. 12, 2013.

Doxil label (labeling revision Jun. 10, 2008). Retrieved from the internet: http://www.accessdata.fda.gov/drugsatfda_docs/label/2008/050718s033lbl.pdf.

Abraxane label (labeling revision Dec. 23, 2011). Retrieved from the internet: http://www.accessdata.fda.gov/drugsatfda_docs/label/2011/021660s025s026s029lbl.pdf.

Dawidczyk, et al., "State-of-the-art in design rules for drug delivery platforms: Lessons learned from FDA-approved nanomedicines," Journal of Controlled Release 187 (2014), pp. 133-144.

CAS Registry Record for 23214-92-8 (doxorubicin), entered STN Nov. 16, 1984.

CAS Registry Record for 97682-44-5 (irinotecan), entered STN Aug. 18, 1985.

Gemzar label (labeling revision Feb. 4, 2011). Retrieved from the internet: http://www.accessdata.fda.gov/drugsatfda_docs/label/2011/020509s069lbl.pdf.

Non-Final Rejection of U.S. Appl. No. 11/121,294 (U.S. Pat. No. 8,147,867), dated Dec. 6, 2010, and Notice of References Cited, dated Dec. 6, 2010.

Non-Final Rejection of U.S. Appl. No. 11/121,294 (U.S. Pat. No. 8,147,867), dated Aug. 17, 2009, and Notice of References Cited, dated Aug. 17, 2009.

Doxil label (labeling revision Apr. 15, 2015). Retrieved from the internet: http://www.accessdata.fda.gov/drugsatfda_docs/label/2015/050718s048lbl.pdf.

Abraxane label (labeling revision Jul. 21, 2015). Retrived from the internet: http://www.accessdata.fda.gov/drugsatfda_docs/label/2015/021660s041lbl.pdf.

Gemzar label (labeling revision May 8, 2014). Retrieved from the internet: http://www.accessdata.fda.gov/drugsatfda_docs/label/2014/020509s077lbl.pdf.

Drummond, Daryl. C., et al., "Development of a Highly Active Nanoliposomal Irinotecan Using a Novel Intraliposomal Stabilization Strategy," Cancer Research 2006; 66: (6). Mar. 15, 2006, pp. 3271-3277.

Rahma, O. E., et al. "Second-line treatment in advanced pancreatic cancer: a comprehensive analysis of published clinical trials," Annals of Oncology Advance Access published May 12, 2013, pp. 1-8.

Ko, A. H., et al. "A Multinational Phase II Study of PEP02 (MM-398), Liposome Irinotecan, for Patients with Gemcitabine-refractory Metastatic Pancreatic Cancer," Poster presented at the American Society of Clinical Oncology meeting, Jun. 3-Jun. 7, 2011, Chicago, Illinois.

Chen, L., et al. "Phase I study of liposome irinotecan (PEP02) in combination with weekly infusion of 5-FU/LV in advanced solid tumors," Journal of Clinical Oncology, 2010 ASCO Annual Meeting Abstracts, vol. 28, No. 15_suppl (May 20 Supplement) 2010: e13024.

"Study of PEP02 as a Second Line Therapy for Metastatic Pancreatic Cancer," Mar. 1, 2012. Retrieved from the internet: ClinicalTrials.gov Archive.

"A multinational phase II study of PEP02 (liposome irinotecan) for patients with gemcitabine-refractory metastatic pancreatic cancer," J Clin Oncol, vol. 29 (2011) ASCO Annual Meeting.

Chen, L., et al., "Phase I Study of Liposome Encapsulated Irinotecan (PEP02) in Advanced Solid Tumor Patients," Poster presented at the ASCO meeting of May 30-Jun. 3, 2008, Chicago, Illinois.

Kim, J., et al., "Sustained Intratumoral activation of MM-398 results in superior activity over irinotecan demonstrated by using a systems pharmacology approach." Poster presented at the AACR Pancreatic Cancer Symposium, Jun. 18-21, 2012, New York, New York.

Ko, A-H, et al. "A multinational phase 2 study of nanoliposomal irinotecan sucrosafate (PEP02,MM-398) for patients with gemcitabine-refractory metastatic pancreatic cancer," British Journal of Cancer (2013), 109, pp. 920-925.

"A Randomized Phase II Study of PEP02 or Irinotecan in Combination With Leucovorin and 5-Flourouracil in Second Line Therapy of Metastatic Colorectal Cancer," Clinical Trials Identifier: NCT01375816, Jun. 16, 2011 version. Retrieved from the internet: ClinicalTrials.gov archive.

"A Phase II Study of PEP02 as a Second Line Therapy for Patients With Metastatic Pancreatic Cancer," Clinical Trials Identifier: NCT00813163, Mar. 1, 2012 version. Retrieved from the internet: ClinicalTrials.gov.archive.

(56) References Cited

OTHER PUBLICATIONS

Makrilia, N., et al. "Treatment for Refractory Pancreatic Cancer," Highlights from the "2011 ASCO Gastrointestinal Cancers Symposium," San Francisco, CA, USA, Jan. 20-22, 2011, Journal of the Pancreas, vol. 12, No. 2—Mar. 2011 [ISSN 1590-8577], pp. 110-113.

Yi, Seong Yoon, et al., "Irinotecan monotherapy as second-line treatment in advanced pancreatic cancer," Cancer Chemother Pharmacol, (2009) 63, pp. 1141-1145.

Neuzillet, C., et al., "FOLFIRI regimen as second-/third-line chemotherapy in patients with advanced pancreatic adenocarcinoma refractory to gemcitabine and platinum salts: A retrospective series of 70 patients." 2011 Gastrointestinal Cancers Symposium, J Clin Oncol 29: 2011 (suppl 4; abstr 272), pp. 1-2.

Taieb, J., "FOLFIRI.3, a new regimen combining 5-fluorouracil folinic acid and irinotecan, for advanced pancreatic cancer: results of an Association des Gastro-Enterologues Oncologues (Gastroenterologist Oncologist Association) multicenter phase II study," Annals of Oncology, vol. 19, Issue 3 (2007), 11 pages.

Chen, L., et al., "Phase I study of liposome encapsulated irinotecan (PEP02) in advanced solid tumor patients," Journal of Clinical Oncology, 2008 ASCO Annual Meeting Proceedings (Post-Meeting Edition), vol. 26, No. 15S (May 20 Supplement), 2008: 2565.

Ko, A. H., et al., "A multinational phase II study of PEP02 (liposome irinotecan) for patients with gemcitabine-refractory metastatic pancreatic cancer," J Clin Oncol 29: 2011 (suppl; abstr 4069) 2011 ASCO Annual Meeting.

Yoo, C., et al., "A randomised phased II study of modified FOLFIRI.3 vs modified FOLFOX as second-line therapy in patients with gemcitabine-rafractory advanced pancreatic cancer," British Journal of Cancer (2009) 101, pp. 1658-1663.

Zaniboni, A., et al. "FOLFIRI as second-line chemotherapy for advanced pancreatic cancer: a GISCAD multicenter phase II study," Cancer Chermother Pharmacol (2012) 69, pp. 1641-1645.

Grant, et al., Dose-ranging evaluation of the substituted benzamide dazopride when used as an antiemetic in patients receiving anticancer chemotherapy, 1993, Cancer Chemotherapy and Pharmacology, 31, pp. 442-444.

Kozuch, et al., Irinotecan combined with Gemcitabine, 5-Fluorouracil, Leucovorin, and Cisplatin (G-FLIP) is an effective and noncrossresistant treatment for chemotherapy refractory metastatic pancreatic cancer, 2001, The Oncologist, 6, pp. 488-495.

"Study of MM-398 Versus 5-Fluorouracil and Leucovorin in Patients With Metastatic Pancreatic Cancer", Dec. 11, 2011 (Dec. 11, 2011), pp. 1-3, XP055075223. URL:http://clinicaltrials.gov/archive/NCT01494506/2011_12_16.

"Study of MM-398 With or Without 5-Fluorouracil and Leucovorin, Versus 5-Fluorouracil and Leucovorin in Patients With Metastatic Pancreatic Cancer", Aug. 9, 2012, pp. 1-3, XP055075259, Retrieved from the Internet: URL:http://clinicaltrials.gov/archive/NCT01494506/2012_08_09.

Baker J. et al., Irinophore C, a Novel Nanoformulation of Irinotecan, Alters Tumor Vascular Function and Enhances the Distribution of 5-Fluorouracil and Doxorubicin, Clin Cancer Res 2008; 14(22), pp. 7260-7271.

Brixi-Benmansour, Hedia, et al, "Phase II study of first-line FOLFIRI for progressive metastatic well-differentiated pancreatic endocrine carcinoma", Digestive and Liver Disease, W.B. Saunders, GB, vol. 43, No. 11, Jul. 1, 2011, pp. 912-916.

Eisenhauer, E.A., et al., New response evaluation criteria in solid tumours: Revised RECIST guideline (version 1.1), European Journal of Cancer, 45, 2009, pp. 228-247.

Hoskins, J.M, et al., "UGTA1A1*28 Genotype and Irinotecan-Induced Neutropenia: Dose Matters", JNCI Journal of the National Cancer Institute, vol. 99, No. 17, Sep. 5, 2007, pp. 1290-1295.

Infante, Jeffrey R., et al, "Phase I and pharmacokinetic study of IHL-305.(PEGylated liposomal Irinotecan) in patients with advanced solid tumors", Cancer Chemotherapy and Pharmacology, Springer, Berlin, DE, vol. 70, No. 5, Sep. 2, 2012, pp. 699-705.

International Search Report and Written Opinion, PCT/US2013/045495, dated Aug. 22, 2013, pp. 11.

Tsai, Chang-Sung, et al., "Nanovector-based therapies in advanced pancreatic cancer", Journal of Gastrointestinal Oncology, Sep. 1, 2011, pp. 185-194.

Verreault et al., Vascular normalization in orthotopic glioblastoma following intravenous treatment with lipid-based nanoparticulate formulations of irinotecan (Irinophore C™), doxorubicin (Caelyx®) or vincristine. BMC Cancer 2011, 11:124, pp. 1-18.

Waterhouse DN et al., Lipid-based nanoformulation of irinotecan: dual mechanism of action allows for combination chemo/angiogenic therapy. Nanomedicine (2011) 6(9), pp. 1645-1654.

Wilson WR and Hay MP., Targeting hypoxia in cancer therapy. Nat Rev Cancer. <http://www.ncbi.nlm.nih.gov/pubmed/21606941> Jun. 2011; 11(6), pp. 393-410.

International Preliminary Report on Patentability, PCT/US2013/045495, dated Dec. 16, 2014, pp. 1-8.

Chen, L., et al., "Expanded analyses of NAPOLI-1: Phase 3 study of MM-398 (nal-IRI), with or without 5-fluorouracil and leucovorin, versus 5-fluorouracil and leucovorin, in metastatic pancreatic cancer (mPAC) previously treated with gemcitabine-based therapy", Poster presented at the ASCO meeting of May 29-Jun. 2, 2015, Chicago, Illinois.

Gebbia, V. et al., "Irinotecan Plus Bolus/Infusional 5-Fluorouracil and Leucovorin in Patients With Pretreated Advanced Pancreatic Carcinoma: A Multicenter Experience of the Gruppo Oncologico Italia Meridionale", American Journal of Clinical Oncology, vol. 33, 5, Oct. 2010, 461-464.

Munstedt, et al. "Role of dexamethasone dosage in combination with 5-HT3 antagonists for prophylaxis of acute chemotherapy-induced nausea and vomiting" 1999, British Journal of Cancer, 79(3/4), pp. 637-639.

Onivyde [MM-398] label (Oct. 22, 2015). Retrieved from the internet: http://www.accessdata.fda.gov/drugsatfda_docs/label/2015/207793lbl.pdf.

Wang-Gillam, A., et al., "Nanoliposomal irinotecan with flourouracil and folinic acid in metastatic pancreatic cancer after previous gemcitabine-based therapy (NAPOLI-1): a global, randomised, open-label, phase 3 trial", The Lancet, Published online Nov. 22, 2015; http://dx.doi.org/10.1016/S0140-6736(15)00986-1.

A Genotype-guided Dosing Study of mFOLFIRINOX in Previously Untreated Patients with Advanced Gastrointestinal Malignancies. Clinicaltrials.gov posting NCT01643499, updated on Jul. 17, 2012.

A Phase II Study Evaluating the Rate of R0 Resection (Microscopically Negative Margins) After Induction Therapy With 5-Fluorouracil, Leucovorin, Oxaliplatin, Irinotecan (FOLFIRINOX) in Patients With Borderline Resectable or Locally Advanced Inoperable Pancreatic Cancer. Clinicaltrials.gov posting NCT01359007, updated on May 23, 2011.

A Phase II Study Evaluating the Rate of R0 Resection (Microscopically Negative Margins) After Induction Therapy With 5-Fluorouracil, Leucovorin, Oxaliplatin, Irinotecan (FOLFIRINOX) in Patients With Borderline Resectable or Locally Advanced Inoperable Pancreatic Cancer. Clinicaltrials.gov posting NCT01359007, updated on May 28, 2015.

A Phase II Study of PEP02 as a Second Line Therapy for Patients with Metastatic Pancreatic Cancer. Clinicaltrials.gov posting NCT00813163, updated on Jan. 12, 2015.

A Phase II Trial of Bolus Fluorouracil and Oxaliplatin (mFLOX) as First-line Regimen for Patients with Unresectable or Metastatic Pancreatic Cancer Not Eligible for Infusional Fluorouracil, Irinotecan and Oxaliplatin. Clinicaltrials.gov posting NCT02896803, updated on Sep. 11, 2016.

A Pilot Study of Intravenous Ascorbic Acid and Folfirinox in the Treatment of Advanced Pancreatic Cancer. Clinicaltrials.gov posting NCT02896907, updated on Sep. 11, 2016.

A Prospective Evaluation of Neoadjuvant FOLFIRINOX Regimen in Patients with Non-metastatic Pancreas Cancer (Baylor University Medical Center and Texas Oncology Experience). Clinicaltrials.gov posting NCT01771146, updated on Jan. 17, 2013.

A Randomized, Open Label Phase 3 Study of MM-398, With or Without 5-Fluorouracil and Leucovorin, Versus 5. Fluorouracil and

(56) References Cited

OTHER PUBLICATIONS

Leucovorin in Patients with Metastatic Pancreatic Cancer Who Have Failed Prior Gemcitabine-based Therapy. Clinicaltrials.gov posting NCT1494506, updated on Aug. 1, 2013.
A Randomized, Open Label Phase 3 Study of MM-398, With or Without 5-Fluorouracil and Leucovorin, Versus 5 Fluorouracil and Leucovorin in Patients with Metastatic Pancreatic Cancer Who Have Failed Prior Gemcitabine-based Therapy. Clinicaltrials.gov posting NCT1494506, updated on Jun. 16, 2016.
Neoadjuvant FOLFIRINOX and Stereotactic Body Radiotherapy (SBRT) Followed by Definitive Surgery for Patients with Borderline Resectable Pancreatic Adenocarcinoma: A Single-Arm Pilot Study. Clincaltrials.gov posting NCT01992705, updated on Nov. 22, 2013.
A Randomized Phase III Study Evaluating Modified FOLFIRINOX (mFFX) with or without Stereotactic Body Radiotherapy (SBRT) in the Treatment of Locally Advanced Pancreatic Cancer. Clinicaltrials.gov posting NCT01926197, updated on Aug. 19, 2013.
Phase I Study of Stereotactic Body Radiation Therapy and 5-Fluorouracil, Oxaliplatin and Irinotecan (FOLFIRINOX) in the Neoadjuvant Therapy of Pancreatic Caner. Clinicaltrials.gov posting NCT01446458, updated on Oct. 4, 2011.
PhaseI/II Study to Evaluate Nab-paclitaxel in Substitution of CPT11 or Oxaliplatin in FOLFIRINOX Schedule as First Line Treatment on Metastatic Pancreatic Cancer. Clinicaltrials.gov posting NCT02109341, updated on Apr. 8, 2014.
Phase II Single Arm Clinical Trial of FOLFIRINOX for Unresectable Locally Advanced and Borderline Resectable Pancreatic Caner. Clinicaltrials.gov posting NCT01688336, updated on Sep. 18, 2012.
Phase II Study of Modified FOLFIRINOX in Advanced Pancreatic Cancer. Clinicaltrials.gov posting NCT01523457, updated on Jan. 31, 2012.
Phase II Study of Peri-Operative Modified Folfirinox in Localized Pancreatic Cancer. Clinicaltrials.gov posting NCT02047474, updated on Jan. 27, 2014.
Phase II Trial to Investigate the Efficacy and Safety of mFOLFIRINOX in Patients with Metastatic Pancreatic Cancer in China. Clinicaltrials.gov posting NCT02028806, updated on Jan. 6, 2014.
Phase-2 Study Evaluating Overall Response Rate (Efficacy) and Autonomy Daily Living Preservation (Tolerance) of "FOLFIRINOX" Pharmacogenic Dose Adjusted, in Elderly Patients (70 yo. or Older) with a Metastatic Pancreatic Adenocarcinoma. Clinicaltrials.gov posting NCT02143219, updated on May 20, 2014.
The Pilot Study of Neoadjuvant Chemotherapy of FIRINOX in Patients with Borderline Resectable Pancreatic Cancer. Clinicaltrials.gov posting NCT02148549, updated on May 27, 2014.

A Study of PEP02 in Combination With 5-fluorouracil (5-FU) and Leucovorin (LV) in Advanced Solid Tumors. ClinicalTrials.gov posting NCT02884128, last updated Aug. 25, 2016.
Pharmacokinetic Study of Biweekly PEP02 (Liposome Irinotecan) in Patients With Metastatic Colorectal Cancer Refractory to First-line Oxaliplatin-based Chemotherapy. ClinicalTrials.gov posting NCT00940758 on Jul. 16, 2009.
Phase I and Pharmacokinetic Study of Biweekly PEP02 in mCRC Refractory to 1st-line Oxaliplatin Base Therapy. ClinicalTrials.gov posting NCT00940758, last updated Mar. 1, 2012.
Phase I and Pharmacokinetic Study of Biweekly PEP02 (Liposome Irinotecan) in Patients With Metastatic Colorectal Cancer Refractory to First-line Oxaliplatin-based Chemotherapy. ClinicalTrials. gov posting NCT00940758 on Feb. 3, 2010.
Saltz LB, Cox JV, Blanke C, Rosen LS, Fehrenbacher L, Moore MJ, Maroun JA, Ackland SP, Locker PK, Pirotta N et al. Irinotecan plus fluorouracil and leucovorin for metastatic colorectal cancer. Irinotecan Study Group. N Engl J Med. 2000;343(13):905-14.
Douillard JY, Cunningham D, Roth AD, Navarro M, James RD, Karasek P, Jandik P, Iveson T, Carmichael J, Alakl M et al. Irinotecan combined with fluorouracil compared with fluorouracil alone as first-line treatment for metastatic colorectal cancer: a multicentre randomised trial. Lancet. 2000; 355(9209):1041-7.
Kambe M, Kikuchi H, Gamo M, Yoshioka T, Ohashi Y, Kanamaru R. Phase I study of irinotecan by 24-h intravenous infusion in combination with 5-fluorouracil in metastatic colorectal cancer. Int J Clin Oncol. 2012;17(2):150-4.
Fuchs CS, Moore MR, Harker G, Villa L, Rinaldi D, Hecht Jr. Phase III comparison of two irinotecan dosing regimens in second-line therapy of metastatic colorectal cancer. J Clin Oncol. 2003;21(5):807-14.
Kohne CH, Wils J, Lorenz M, Schoffski P, Voigtmann R, Bokemeyer C, Lutz M, Kleeberg C, Ridweiski K, Souchon R et al. Randomized phase III study of high-dose fluorouracil given as a weekly 24-h infusion with or without leucovorin versus bolus fluorouracil plus leucovorin in advanced colorectal cancer: European organization of Research and Treatment of Cancer Gastrointestinal Group Study 40952. J Clin Oncol. 2003;21(20):3721-8.
Rivory LP, Haaz MC, Canal P, Lokiec F, Armand JP, Robert J. Pharmacokinetic interrelationships of irinotecan (CPT-11) and its three major plasma metabolites in patients enrolled in phase I/II trials. Clin Cancer Res. 1997;3(8):1261-6.
Rothenberg ML, Kuhn JG, Burris 3rd HA, Nelson J, Eckardt JR, Tristan-Morales M, Hilsenbeck SG, Weiss GR, Smith LS, Rodriguez GI et al. Phase I and pharmacokinetic trial of weekly CPT-11. J Clin Oncol. 1993;11(11):2194-204.
Palomaki GE, Bradley LA, Douglas MP, Kolor K, Dotson WD. Can UGT1A1 genotyping reduce morbidity and mortality in patients with metastatic colorectal cancer treated with irinotecan? An evidence-based review. Genet Med. 2009;11 (1):21-34. doi:10.1097/GIM.1090b1013e31818efd31877.
Minami H, Sai K, Saeki M, Saito Y, Ozawa S, Suzuki K, Kaniwa N, Sawada J, Hamaguchi T, Yamamoto N et al. Irinotecan pharmacokinetics/pharmacodynamics and UGT1A genetic polymorphisms in Japanese: roles of UGT1A1 6 and 28. Pharmacogenet Genomics. 2007;17(7):497-504.

Activity of MM-398 (Ls-CPT11) in an Orthotopic Pancreas Tumor Model Expressing Luciferase (L3.6pl).

Accumulation of SN-38 in Tumors Following Treatment with Free Irinotecan or Nanoliposomal Irinotecan (MM-398).

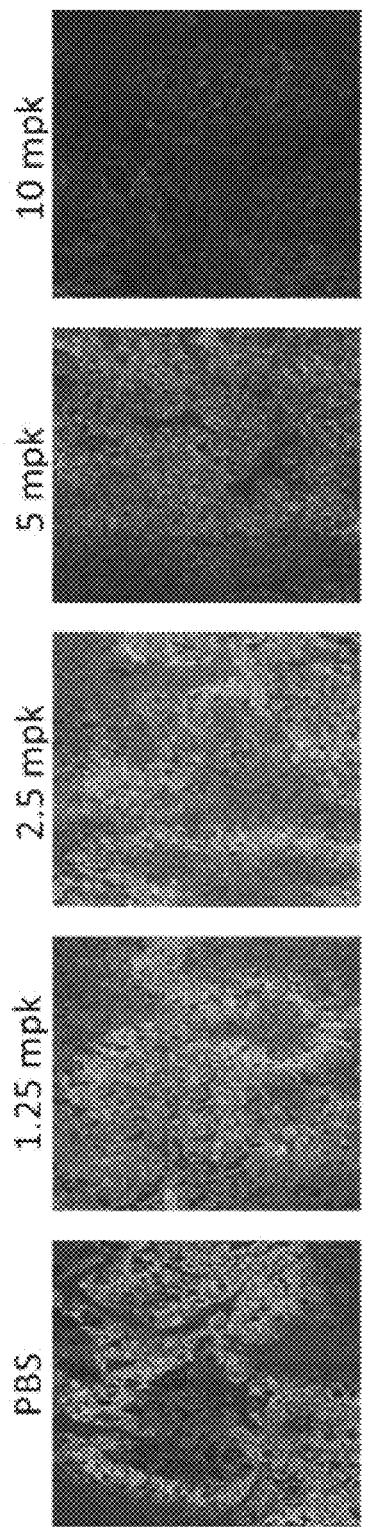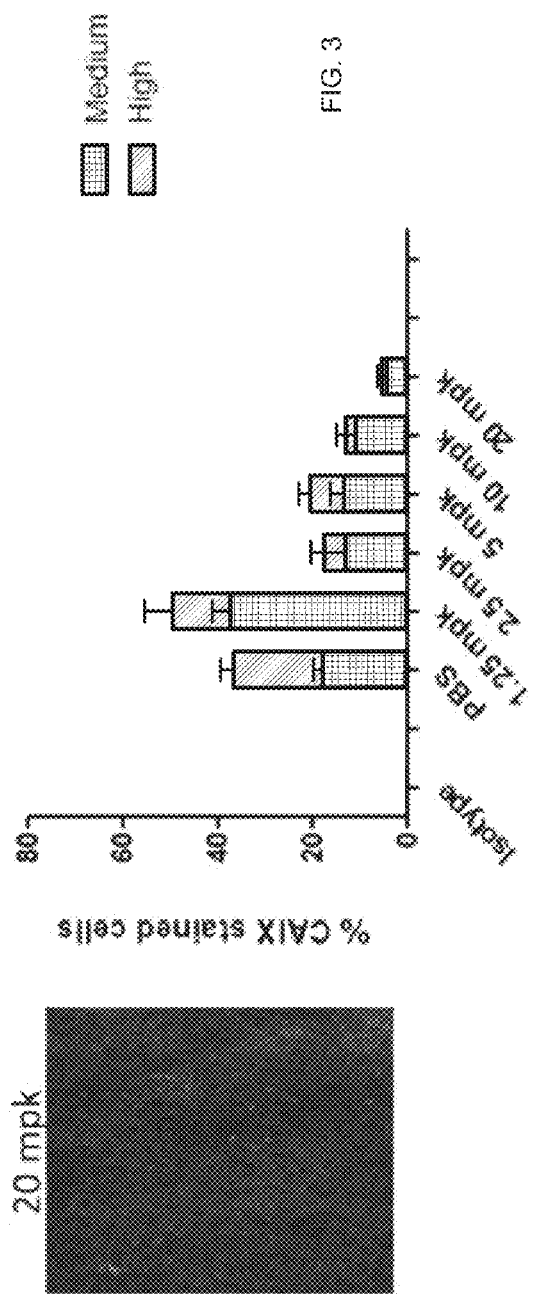
FIG. 3

MM-398 PK in q3w (irinotecan, liposomes + free drug)

| Dose (mg/m²) & Study | PEP0203 | | | | PEP0201 | | | PEP0206 | | Campto® Package insert | |
|---|---|---|---|---|---|---|---|---|---|---|---|
| | 60 | 80 | 100 | 120 | 120 | 180 | 120 | 300 | 125 | 340 | |
| | (n=3) | (n=6) | (n=4) | (n=2) | (n=6) | (n=4) | (n=37) | (n=27) | (N=64) | (N=6) | |
| Parameters | | | | | | | | | | | |
| $C_{max}$ (μg/mL) | 28.93 (±15.75) | 29.16 (±5.24) | 44.06 (±7.65) | 47.94 (±16.24) | 79.4 (±13.9) | 102 (±17.6) | 60.8 (±36.6) | 4.3 (±1.2) | 1.66 (±0.797) | 3.392 (±0.874) | mg/m² |
| $t_{1/2}$ (h) | 24.02 (±16.76) | 32.09 (±18.21) | 48.11 (±17.41) | 30.65 (±5.32) | 29.5 (±17.2) | 22.2 (±11.5) | 21.2 (±18.3) | 7.7 (±4.4) | 5.8 (±0.7) | 11.7 (±1.0) | |
| $AUC_{0-T}$ (μg·h/mL) | 1,047 (±1,156) | 1,116 (±810) | 2,193 (±1,017) | 1,117 (±308) | 2,835 (±1,817) | 1,945 (±1,029) | 1,651.5 (±1,412.0) | 24.2 (±7.7) | 10.2 (±3.27) | 20,604 (±6,027) | |
| $AUC_{0-\infty}$ (μg·h/mL) | 1,114 (±1,270) | 1,211 (±924) | 2,472 (±1261) | 1,261 (±500) | 2,963 (±1,947) | 1,963 (±1,035) | 1,812.2 (±1,601.9) | 26.2 (±9.0) | | | |
| Cl (L/h/m²) | 0.1249 (±0.1058) | 0.1164 (±0.0949) | 0.0547 (±0.0358) | 0.1033 (±0.0409) | 0.0591 (±0.0367) | 0.119 (±0.0703) | 0.191 (±0.260) | 12.9 (±4.7) | 13.3 (±6.01) | 13.9 (±4.0) | |
| $V_{ss}$ (L/m²) | 2.6 (±1.44) | 2.93 (±0.60) | 2.63 (±0.49) | 3.16 (±0.38) | 1.8 (±0.771) | 1.97 (±0.342) | 2.23 (±0.69) | 98.5 (±29.0) | 110 (±48.5) | 234 (±69.6) | |

Note: AUC 0-T is defined as T = 24 hours for Camptosar package insert, T = 49.5 hours for Camptosar in the PEP0206 study and T = 169.5 hours for MM-398.

FIG. 5

Note: AUC 0-T is defined as T = 24 hours for Camptosar package insert,
T = 49.5 hours for Camptosar in the PEP0206 study and
T = 169.5 hours for MM-398.

MM-398 PK in q3w (SN-38)

| Dose (mg/m²) & Study | PEP0203 | | | | PEP0201 | | PEP0206 | | Campto® Package insert | |
|---|---|---|---|---|---|---|---|---|---|---|
| | 60 (n=3) | 80 (n=6) | 100 (n=4) | 120 (n=2) | 120 (n=6) | 180 (n=4) | PEP02 120 (n=37) | Campto® 300 (n=27) | 125 mg/m² (N=64) | 340 mg/m² (N=6) |
| Parameters | | | | | | | | | | |
| $C_{max}$ (ng/mL) | 7.02 (±5.64) | 7.98 (±4.39) | 7.39 (±1.68) | 16.64 (±9.36) | 9.2 (±3.5) | 14.3 (±6.16) | 8.79 (±8.68) | 44.1 (±28.2) | 26.3 (±11.9) | 56.0 (±28.2) |
| $t_{1/2}$ (h) | 183.81 (±172.3) | 53.75 (±15.6) | 73.41 (±18.3) | 26.23 (±6.53) | 75.4 (±43.8) | 58.0 (±32.8) | 88.8 (±114.6) | 22.8 (±10.9) | 10.4 (±3.1) | 21.0 (±4.3) |
| $AUC_{0-T}$ (ng·h/mL) | 367.40 (±227) | 354.77 (±145) | 551.40 (±381.8) | 367.60 (±155.7) | 710 (±395) | 1,160 (±969) | 467 (±310) | 361 (±125) | 229 (±108) | 474 (±245) |
| $AUC_{0-\infty}$ (ng·h/mL) | 1,373.3 (±1,119) | 502.15 (±153) | 844.28 (±444) | 474.00 (±209) | 997 (±680) | 1,420 (±1,134) | 879 (±1,426) | 440 (±162) | -- | -- |

FIG. 6

| | | MM-398 + 5-FU/LV (N=117) | 5-FU/LV (N=119) | MM-398 (N=151) | 5-FU/LV (N=149) |
|---|---|---|---|---|---|
| Age | Median years (min, max) | 63 (41, 81) | 62 (34, 80) | 65 (31, 87) | 63 (34, 83) |
| Sex | Male, % | 59 | 56 | 58 | 54 |
| | Female, % | 41 | 44 | 42 | 46 |
| KPS | 90-100, % | 56 | 56 | 56 | 56 |
| | 70-80, % | 44 | 44 | 44 | 44 |
| Race | Caucasian, % | 64 | 63 | 60 | 60 |
| | East Asian, % | 29 | 30 | 35 | 34 |
| | Other, % | 7 | 7 | 5 | 6 |
| Pancreatic primary location | Head, % | 64 | 58 | 65 | 54 |
| | Other, % | 36 | 42 | 35 | 46 |
| CA19-9* | > 30 U/mL, % | 84 | 81 | 86 | 81 |

* CA19-9 at baseline was unknown in 3% of patients

FIG. 10

| Parameter | PP (N=66) | Non-PP (N=51) | PP (N=71) | Non-PP (N=48) |
|---|---|---|---|---|
| KPS 90 and 100, % | 62 | 49 | 61 | 50 |
| Albumin ≥ 4.0 g/dL, % | 48 | 41 | 48 | 42 |
| Race, (%) | | | | |
| Caucasian | 71 | 55 | 63 | 63 |
| East Asian | 21 | 39 | 31 | 29 |
| CA 19-9 ≥ 40, %* | 82 | 79 | 76 | 86 |
| Pancreatic head tumor, % | 61 | 71 | 68** | 44** |
| Liver Metastasis, % | 64 | 65 | 75 | 65 |
| Line of Treatment, % | | | | |
| First line | 14 | 12 | 13 | 13 |
| Second line | 53 | 53 | 59 | 52 |
| Post-second line | 33 | 35 | 28 | 35 |
| Time since last therapy, months*** | 1.4 (0.9, 2.1) | 1.4 (1.0, 2.8) | 1.2 (1.0, 2.3) | 1.2 (1.0, 2.1) |
| Time since diagnosis, months*** | 10.3 (5.2, 15.8) | 10.8 (6.6, 19.1) | 10.3 (6.5, 15.1) | 10.5 (5.6, 16.2) |
| Stage 4 at diagnosis, % | 53 | 51 | 51 | 54 |

FIG. 15

| | Safety Population | | | PP | |
|---|---|---|---|---|---|
| | MM-398 + 5-FU/LV (N=117) | 5-FU/LV (N=134) | | MM-398 + 5-FU/LV (N=66) | 5-FU/LV (N=71) |
| Number of patients with Treatment Emergent Adverse Events resulting in, n (%) | | | | | |
| Dose Reduction | 39 (33) | 5 (4) | | 22 (33) | 2 (3) |
| Dose Delays | 72 (62) | 43 (32) | | 40 (61) | 15 (21) |
| Treatment Discontinuation | 13 (11) | 10 (8) | | 3 (5) | 2 (3) |
| Average relative dose intensity (%) | | | | | |
| MM-398 | 83.2 | - | | 85.4 | - |
| 5-FU | 83.9 | 95.6 | | 86.4 | 97.9 |
| Average duration of exposure (weeks)* | 15 | 10 | | 21 | 13 |

FIG. 16

|  | Safety Population[1] | | PP | |
|---|---|---|---|---|
|  | MM-398 + 5-FU/LV (N=117) | 5-FU/LV (N=134) | MM-398 + 5-FU/LV (N=66) | 5-FU/LV (N=71) |
| Grade ≥ 3 nonhematologic AEs in > 5% patients, %[2] | | | | |
| Fatigue | 14 | 4 | 14 | 6 |
| Diarrhea | 13 | 5 | 12 | 7 |
| Vomiting | 11 | 3 | 8 | 3 |
| Nausea | 8 | 3 | 9 | 1 |
| Asthenia | 8 | 7 | 5 | 6 |
| Abdominal pain | 7 | 6 | 5 | 3 |
| Grade ≥ 3 hematologic AEs based on laboratory values, %[2,3] | | | | |
| Neutrophil count decreased | 20 | 2 | 15 | 3 |
| Hemoglobin decreased | 6 | 5 | 6 | 4 |
| Platelet count decreased | 2 | 0 | 2 | 0 |
| Patients with at least 1 AE leading to death (all causes), % | 2 | 7 | 0 | 6 |

[1] Patients receiving at least one dose of study drug; [2] Per CTCAE Version 4; [3] includes only patients who had at least one post-baseline assessment

FIG. 17

Demographics and Baseline Characteristics (PRO Population)

| Parameter | nal-IRI + 5-FU/LV<br>n = 71 | 5-FU/LV<br>n = 57 |
|---|---|---|
| Sex, n (%) | | |
| Male | 43 (60.6) | 31 (54.4) |
| Female | 28 (39.4) | 26 (45.6) |
| Age, median (range), years | 63.0 (41-81) | 63.0 (41-80) |
| Ethnicity, n (%) | | |
| White | 42 (59.2) | 39 (68.4) |
| East Asian | 22 (31.0) | 16 (28.1) |
| Other | 7 (9.9) | 2 (3.5) |
| KPS score, n (%) | | |
| 100 | 12 (16.9) | 8 (14.0) |
| 90 | 31 (43.7) | 23 (40.4) |
| 80 | 24 (33.8) | 22 (38.6) |
| 70 | 3 (4.2) | 4 (7.0) |
| 60 | 1 (1.4) | 0 |

FIG. 25

Treatment-Emergent Adverse Events From the Primary Analysis of the NAPOLI-1 Trial

| | nal-IRI + 5-FU/LV n = 117 | | | 5-FU/LV n = 134 | |
|---|---|---|---|---|---|
| | Any Grade | Grades 3/4 | | Any Grade | Grades 3/4 |
| Diarrhea | 69 (59) | 15 (13) | | 35 (26) | 6 (4) |
| Vomiting | 61 (52) | 13 (11) | | 35 (26) | 4 (3) |
| Nausea | 60 (51) | 9 (8) | | 46 (34) | 4 (3) |
| Decreased appetite | 52 (44) | 5 (4) | | 43 (32) | 3 (2) |
| Fatigue | 47 (40) | 16 (14) | | 37 (28) | 5 (4) |
| Neutropenia[a] | 46 (39) | 32 (27) | | 7 (5) | 2 (1) |
| Anemia | 44 (38) | 11 (9) | | 31 (23) | 9 (7) |

FIG. 30

Demographics and Baseline Characteristics (Safety Population)

| Parameter | nal-IRI + 5-FU/LV n = 117 | 5-FU/LV n = 134 |
|---|---|---|
| Sex, n (%) | | |
| Male | 67 (57.3) | 73 (54.5) |
| Female | 50 (42.7) | 61 (45.5) |
| Age, median (range), years | 63 (41-81) | 63 (39-83) |
| Ethnicity, n (%) | | |
| White | 73 (62.4) | 85 (63.4) |
| East Asian | 33 (28.2) | 44 (32.8) |
| Other | 11 (9.4) | 5 (3.7) |
| KPS score, n (%) | | |
| 100 | 19 (16.2) | 16 (11.9) |
| 90 | 50 (42.7) | 50 (37.3) |
| 80 | 39 (33.3) | 57 (42.5) |
| 70 | 7 (6.0) | 11 (8.2) |
| 60 | 2 (1.7) | 0 |
| Previous lines of metastatic therapy, n (%) | | |
| 0 | 15 (12.8) | 18 (13.4) |
| 1 | 63 (53.8) | 79 (59.0) |
| ≥2 | 39 (33.3) | 37 (27.6) |
| Previous anticancer therapy, n (%) | | |
| Gemcitabine alone | 54 (46.2) | 61 (45.5) |
| Gemcitabine combination | 63 (53.8) | 73 (54.5) |
| Fluorouracil | 50 (42.7) | 53 (39.6) |
| Irinotecan | 12 (10.3) | 14 (10.4) |
| Platinum | 37 (31.6) | 38 (28.4) |

FIG. 31

TEAEs by Age

| | nal-IRI + 5-FU/LV | | | | <65 Years n = 78 | | ≥65 Years n = 56 | |
|---|---|---|---|---|---|---|---|---|
| | <65 Years n = 63 | | ≥65 Years n = 54 | | 5-FU/LV | | | |
| | Any Grade | Grade ≥3 | Any Grade | Grade ≥3 | Any Grade | Grade ≥3 | Any Grade | Grade ≥3 |
| Any TEAE | 63 (100) | 9 (14.3) | 53 (98.1) | 4 (7.4) | 77 (98.7) | 2 (2.6) | 55 (98.2) | 2 (3.6) |
| Any TEAE grade ≥3 | 53 (84.1) | 9 (14.3) | 37 (68.5) | 6 (11.1) | 44 (56.4) | 5 (6.4) | 31 (55.4) | 1 (1.8) |
| Any TEAE resulting in dose modification[a] | 46 (73.0) | 3 (4.8) | 37 (68.5) | 6 (11.1) | 25 (32.1) | 1 (1.3) | 23 (41.1) | 3 (5.4) |
| TEAEs (reported in ≥30% of patients in any arm) | | | | | | | | |
| Vomiting | 41 (65.1) | 9 (14.3) | 20 (37.0) | 4 (7.4) | 22 (28.2) | 2 (2.6) | 13 (23.2) | 2 (3.6) |
| Diarrhea | 39 (61.9) | 9 (14.3) | 30 (55.6) | 6 (11.1) | 22 (28.2) | 5 (6.4) | 13 (23.2) | 1 (1.8) |
| Nausea | 38 (60.3) | 3 (4.8) | 22 (40.7) | 6 (11.1) | 29 (37.2) | 1 (1.3) | 17 (30.4) | 3 (5.4) |
| Decreased appetite | 30 (47.6) | 2 (3.2) | 22 (40.7) | 3 (5.6) | 22 (28.2) | 3 (3.8) | 21 (37.5) | 0 |
| Neutropenia[a] | 24 (38.1) | 17 (27.0) | 22 (40.7) | 15 (27.8) | 4 (5.1) | 2 (2.6) | 3 (5.4) | 0 |
| Fatigue | 23 (36.5) | 8 (12.7) | 24 (44.4) | 8 (14.8) | 21 (26.9) | 3 (3.8) | 16 (28.6) | 2 (3.6) |
| Anemia | 19 (30.2) | 5 (7.9) | 25 (46.3) | 6 (11.1) | 13 (16.7) | 5 (6.4) | 18 (32.1) | 4 (7.1) |
| Abdominal pain | 17 (27.0) | 5 (7.9) | 10 (18.5) | 3 (5.6) | 23 (29.5) | 6 (7.7) | 19 (33.9) | 2 (3.6) |

FIG. 32

TEAEs by Ethnicity

| | nal-IRI + 5-FU/LV | | | | 5-FU/LV | | | |
|---|---|---|---|---|---|---|---|---|
| | White n = 73 | | East Asian n = 33 | | White n = 85 | | East Asian n = 44 | |
| | Any Grade | Grade ≥3 | Any Grade | Grade ≥3 | Any Grade | Grade ≥3 | Any Grade | Grade ≥3 |
| Any TEAE | 72 (98.6) | 14 (19.2) | 33 (100) | 1 (3.0) | 84 (98.8) | 4 (4.7) | 43 (97.7) | 2 (4.5) |
| Any TEAE, grade ≥3 | 51 (69.9) | 6 (8.2) | 29 (87.9) | 2 (6.1) | 48 (56.5) | 3 (3.5) | 24 (54.5) | 1 (2.3) |
| Any TEAE resulting in dose modification[a] | 48 (65.8) | 14 (19.2) | 28 (84.8) | 0 | 33 (38.8) | 3 (3.5) | 13 (29.5) | 2 (4.5) |
| TEAEs (reported in ≥30% of patients in any arm) | | | | | | | | |
| Diarrhea | 45 (61.6) | 14 (19.2) | 16 (48.5) | 1 (3.0) | 24 (28.2) | 4 (4.7) | 11 (25.0) | 2 (4.5) |
| Nausea | 37 (50.7) | 6 (8.2) | 18 (54.5) | 2 (6.1) | 28 (32.9) | 3 (3.5) | 16 (36.4) | 1 (2.3) |
| Fatigue | 35 (47.9) | 14 (19.2) | 8 (24.2) | 0 | 25 (29.4) | 3 (3.5) | 10 (22.7) | 2 (4.5) |
| Vomiting | 34 (46.6) | 10 (13.7) | 22 (66.7) | 2 (6.1) | 23 (27.1) | 4 (4.7) | 12 (27.3) | 0 |
| Anemia | 29 (39.7) | 4 (5.5) | 13 (39.4) | 7 (21.2) | 16 (18.8) | 3 (3.5) | 15 (34.1) | 6 (13.6) |
| Decreased appetite | 24 (32.9) | 2 (2.7) | 22 (66.7) | 2 (6.1) | 24 (28.2) | 1 (1.2) | 18 (40.9) | 2 (4.5) |
| Neutropenia[a] | 21 (28.8) | 13 (17.8) | 22 (66.7) | 18 (54.5) | 4 (4.7) | 0 | 2 (4.5) | 1 (2.3) |
| Abdominal pain | 20 (27.4) | 6 (8.2) | 6 (18.2) | 2 (6.1) | 30 (35.3) | 7 (8.2) | 11 (25.0) | 1 (2.3) |
| White blood cell count decreased | 4 (5.5) | 2 (2.7) | 12 (36.4) | 7 (21.2) | 1 (1.2) | 0 | 0 | 0 |

FIG. 33

TEAEs by UGT1A1*28 Allele (TA7/TA7 Genotype)

| | nal-IRI + 5-FU/LV | | | | 5-FU/LV | | | |
|---|---|---|---|---|---|---|---|---|
| | TA7/TA7 Genotype n = 7 | | No TA7/TA7 Genotype n = 110 | | TA7/TA7 Genotype n = 13 | | No TA7/TA7 Genotype n = 121 | |
| | Any Grade | Grade ≥3 | Any Grade | Grade ≥3 | Any Grade | Grade ≥3 | Any Grade | Grade ≥3 |
| Any TEAE | 7 (100) | 0 | 109 (99.1) | 11 (10.0) | 13 (100) | 0 | 119 (98.3) | 9 (7.4) |
| Any TEAE, grade ≥3 | 5 (71.4) | 0 | 85 (77.3) | 9 (8.2) | 8 (61.5) | 1 (7.7) | 67 (55.4) | 3 (2.5) |
| Any TEAE resulting in dose modification* | 4 (57.1) | 1 (14.3) | 79 (71.8) | 12 (10.9) | 5 (38.5) | 1 (7.7) | 43 (35.5) | 3 (2.5) |
| TEAEs (reported in ≥20% of patients in any arm) | | | | | | | | |
| Anemia | 3 (42.9) | 0 | 39 (35.5) | 8 (7.3) | 1 (7.7) | 0 | 30 (24.8) | 3 (2.5) |
| Nausea | 3 (42.9) | 0 | 57 (51.8) | 5 (4.5) | 8 (61.5) | 1 (7.7) | 38 (31.4) | 3 (2.5) |
| Vomiting | 3 (42.9) | 1 (14.3) | 58 (52.7) | 14 (12.7) | 7 (53.8) | 1 (7.7) | 28 (23.1) | 3 (2.5) |
| Abdominal pain | 2 (28.6) | 0 | 25 (22.7) | 30 (27.3) | 6 (46.2) | 1 (7.7) | 36 (29.8) | 7 (5.8) |
| Decreased appetite | 2 (28.6) | 0 | 50 (45.5) | 0 | 7 (53.8) | 0 | 36 (29.8) | 3 (2.5) |
| Diarrhea | 2 (28.6) | 1 (14.3) | 67 (60.9) | 14 (12.7) | 4 (30.8) | 1 (7.7) | 31 (25.6) | 5 (4.1) |
| Neutropenia* | 2 (28.6) | 2 (28.6) | 44 (40.0) | 30 (27.3) | 0 | 0 | 7 (5.8) | 2 (1.7) |
| Constipation | 1 (14.3) | 0 | 25 (22.7) | 0 | 4 (30.8) | 1 (7.7) | 28 (23.1) | 1 (0.8) |
| Fatigue | 1 (14.3) | 0 | 46 (41.8) | 16 (14.5) | 4 (30.8) | 1 (7.7) | 33 (27.3) | 4 (3.3) |

FIG. 34

TEAEs by Albumin Level

| | nal-IRI + 5-FU/LV | | | | 5-FU/LV | | | |
|---|---|---|---|---|---|---|---|---|
| | Albumin ≥4.0 g/dL n = 68 | | Albumin <4.0 g/dL n = 47 | | Albumin ≥4.0 g/dL n = 70 | | Albumin <4.0 g/dL n = 62 | |
| | Any Grade | Grade ≥3 | Any Grade | Grade ≥3 | Any Grade | Grade ≥3 | Any Grade | Grade ≥3 |
| Any TEAE | 68 (100) | | 46 (97.9) | | 70 (100) | | 60 (96.8) | |
| Any TEAE grade ≥3 | 55 (80.9) | | 33 (70.2) | | 32 (45.7) | | 42 (67.7) | |
| Any TEAE resulting in dose modification | 48 (70.6) | | 33 (70.2) | | 21 (30.0) | | 26 (41.9) | |
| TEAEs (reported in ≥30% of patients in any arm) | | | | | | | | |
| Diarrhea | 41 (60.3) | 12 (17.6) | 27 (57.4) | 3 (6.4) | 12 (17.1) | 1 (1.4) | 23 (37.1) | 5 (8.1) |
| Nausea | 38 (55.9) | 4 (5.9) | 20 (42.6) | 4 (8.5) | 24 (34.3) | 3 (4.3) | 21 (33.9) | 1 (1.6) |
| Vomiting | 38 (55.9) | 8 (11.8) | 23 (48.9) | 5 (10.6) | 17 (24.3) | 2 (2.9) | 17 (27.4) | 2 (3.2) |
| Decreased appetite | 33 (48.5) | 2 (2.9) | 19 (40.4) | 3 (6.4) | 22 (31.4) | 1 (1.4) | 20 (32.3) | 2 (3.2) |
| Fatigue | 31 (45.6) | 11 (16.2) | 16 (34.0) | 5 (10.6) | 21 (30.0) | 3 (4.3) | 15 (24.2) | 2 (3.2) |
| Neutropenia | 29 (42.6) | 20 (29.4) | 17 (36.2) | 12 (25.5) | 4 (5.7) | 1 (1.4) | 3 (4.8) | 1 (1.6) |
| Anemia | 24 (35.3) | 6 (8.8) | 20 (42.6) | 5 (10.6) | 14 (20.0) | 4 (5.7) | 16 (25.8) | 5 (8.1) |
| Abdominal pain | 19 (27.9) | 6 (8.8) | 7 (14.9) | 2 (4.3) | 24 (34.3) | 4 (5.7) | 17 (27.4) | 4 (6.5) |
| Constipation | 16 (23.5) | 0 | 9 (19.1) | 0 | 22 (31.4) | 2 (2.9) | 10 (16.1) | 0 |

FIG. 35

TEAEs by KPS Score

| | nal-IRI + 5-FU/LV | | | | 5-FU/LV | | | |
|---|---|---|---|---|---|---|---|---|
| | KPS Score ≥90 n = 69 | | KPS Score <90 n = 48 | | KPS Score ≥90 n = 66 | | KPS Score <90 n = 68 | |
| | Any Grade | Grade ≥3 | Any Grade | Grade ≥3 | Any Grade | Grade ≥3 | Any Grade | Grade ≥3 |
| Any TEAE | 69 (100) | 8 (11.6) | 47 (97.9) | 7 (14.6) | 65 (98.5) | 3 (4.5) | 67 (98.5) | 3 (4.4) |
| Any TEAE, grade ≥3 | 52 (75.4) | 4 (5.8) | 38 (79.2) | 5 (10.4) | 27 (40.9) | 1 (1.5) | 48 (70.6) | 3 (4.4) |
| Any TEAE resulting in dose modification* | 48 (69.6) | 8 (11.6) | 35 (72.9) | 5 (10.4) | 19 (28.8) | 2 (3.0) | 29 (42.6) | 2 (2.9) |
| TEAEs (reported in ≥30% of patients in any arm) | | | | | | | | |
| Diarrhea | 40 (58.0) | 8 (11.6) | 29 (60.4) | 7 (14.6) | 22 (33.3) | 3 (4.5) | 13 (19.1) | 3 (4.4) |
| Nausea | 37 (53.6) | 4 (5.8) | 23 (47.9) | 5 (10.4) | 19 (28.8) | 1 (1.5) | 27 (39.7) | 3 (4.4) |
| Vomiting | 36 (52.2) | 8 (11.6) | 25 (52.1) | 5 (10.4) | 16 (24.2) | 2 (3.0) | 19 (27.9) | 2 (2.9) |
| Fatigue | 29 (42.0) | 8 (11.6) | 18 (37.5) | 8 (16.7) | 18 (27.3) | 1 (1.5) | 19 (27.9) | 4 (5.9) |
| Neutropenia* | 29 (42.0) | 20 (29.0) | 17 (35.4) | 12 (25.0) | 4 (6.1) | 1 (1.5) | 3 (4.4) | 1 (1.5) |
| Decreased appetite | 28 (40.6) | 1 (1.4) | 24 (50.0) | 4 (8.3) | 21 (31.8) | 0 | 22 (32.4) | 3 (4.4) |
| Anemia | 25 (36.2) | 6 (8.7) | 19 (39.6) | 5 (10.4) | 18 (27.3) | 4 (6.1) | 13 (19.1) | 5 (7.4) |
| Abdominal pain | 16 (23.2) | 3 (4.3) | 11 (22.9) | 5 (10.4) | 18 (27.3) | 2 (3.0) | 24 (35.3) | 6 (8.8) |
| Constipation | 11 (15.9) | 0 | 15 (31.3) | 0 | 12 (18.2) | 0 | 20 (29.4) | 2 (2.9) |

FIG. 36

METHODS FOR TREATING PANCREATIC CANCER USING COMBINATION THERAPIES

CROSS-REFERENCE TO RELATED APPLICATIONS

This application is a continuation-in-part of U.S. patent application Ser. No. 14/406,776 (filed Dec. 10, 2014), which is incorporated by reference herein in its entirety, and which in turn is a 371 of international application number PCT/US2013/045495 which claims the benefit of priority of U.S. Provisional Application No. 61/659,211 (filed Jun. 13, 2012) and U.S. Provisional Application No. 61/784,382 (filed Mar. 14, 2013), all of which are incorporated herein by reference.

BACKGROUND

Despite improvements in cancer treatments, there remains a critical need to further improve therapies so as to prolong patients' lives while maintaining quality of life, particularly in the case of advanced cancers such as pancreatic cancers that often are, or become, resistant to current therapeutic modalities.

Incidence of pancreatic cancer has markedly increased during the past several decades. It now ranks as the fourth leading cause of cancer death in the United States. Pancreatic cancer's high mortality rate is due to a dearth of effective therapies and a complete absence of reliably durable therapies. Because of the location of the pancreas, pancreatic cancer is typically not diagnosed until a tumor has become large enough to produce systemic symptoms. This, coupled with the absence of good screening tools and a limited understanding of risk factors, results in patients usually having advanced disease, often advanced metastatic disease, at the time of diagnosis. Metastatic pancreatic cancer has a dismal prognosis and is almost uniformly fatal, with an overall survival rate of less than 4% at 5 years.

Chemotherapy with one or more of 5-fluorouracil (5-FU) and gemcitabine has been shown to prolong survival in pancreatic cancer. Combination therapies including folinic acid (leucovorin or levoleucovorin (LV)), 5-fluorouracil, and irinotecan (FOLFIRI), folinic acid, 5-fluorouracil, irinotecan and oxaliplatin (FOLFIRINOX), or, less commonly, a combination of folinic acid, 5-fluorouracil, and oxaliplatin (FOLFOX) are also used to treat some pancreatic cancers. Irinotecan is 7-ethyl-10-[4-(1-piperidino)-1-piperidino]carbonyloxycampothecin, IUPAC name (S)-4,11-diethyl-3,4,12,14-tetrahydro-4-hydroxy-3,14-dioxolH-pyrano[3',4':6,7]-indolizino[1,2-b]quinolin-9-yl-[1,4'bipiperidine]-1'-carboxylate. Irinotecan is a member of the topoisomerase I inhibitor class of drugs and is a semi-synthetic and water soluble analog of the naturally-occurring alkaloid, camptothecin. Also known as CPT-11, irinotecan is currently marketed formulated as an aqueous solution as Camptosar® (irinotecan hydrochloride injection). Topoisomerase I inhibitors such as irinotecan work to arrest uncontrolled cell growth by inhibiting the unwinding of DNA and thereby preventing DNA replication.

The pharmacology of irinotecan is complex, with extensive metabolic conversions involved in the activation, inactivation, and elimination of the drug. Irinotecan is a prodrug that is converted by nonspecific carboxylesterases into a 100-1000 fold more active metabolite, SN-38. SN-38 is not recognized by P-glycoprotein, a drug transporter that plays an important role in acquired drug resistance by pumping certain drugs out of cells, so irinotecan is likely to be active in tumors resistant to other standard chemotherapies. In the body, SN-38 is cleared via glucuronidation, for which major pharmacogenetic variability has been described, and biliary excretion. These drug properties contribute to the marked heterogeneities in efficacy and toxicity observed clinically with irinotecan. Irinotecan hydrochloride injection is approved in the United States for treatment of metastatic colon or renal cancer and is also used to treat colorectal, gastric, lung, uterine cervical and ovarian cancers.

There are few approved treatment options for advanced or metastatic pancreatic cancers, particularly for those of exocrine origin. Single-agent gemcitabine is the current standard of care in first-line treatment of advanced and metastatic pancreatic adenocarcinoma. In clinical trials, single-agent gemcitabine has consistently demonstrated a median prolongation of survival of 5 to 6 months and a 1-year survival rate of about 20%. Single agent gemcitabine was also approved as second line treatment for patients previously treated with but no longer responsive to 5-fluorouracil, with a median overall prolongation of survival of 3.9 months.

Based upon what is known of the biology of pancreatic cancer, a variety of targeted agents have been evaluated, but only erlotinib, a protein tyrosine kinase inhibitor targeted to EGFR, has been approved for first-line use in advanced pancreatic cancer, and the approval is only for use in combination with gemcitabine. The co-administration of erlotinib with gemcitabine resulted in a statistically significant benefit in survival, and improvements in median survival (6.4 months vs. 5.9 months), and 1-year survival rate (24% vs. 17%) compared to gemcitabine alone. Clinical trials evaluating other targeted agents, including studies testing the antibodies bevacizumab and cetuximab, have been disappointingly negative. Thus, there is an urgent need for improvements in, and effective alternatives to, current therapies for pancreatic cancer. The disclosed invention addresses this need and provides other benefits.

SUMMARY

Provided are methods for treating pancreatic cancer in a patient (i.e., a human patient) comprising administering to the patient liposomal irinotecan (e.g., irinotecan sucrose octasulfate salt liposome injection, also referred to as MM-398) alone or in combination with 5-fluorouracil (5-FU) and leucovorin (together, 5-FU/LV), according to a particular clinical dosage regimen. Compositions adapted for use in such methods are also provided.

Preferably, the liposomal irinotecan is irinotecan sucrose octasulfate salt liposome injection. MM-398 irinotecan liposome injection contains the topoisomerase 1 inhibitor irinotecan encapsulated with sucrose octasulfate in a lipid bilayer vesicle or liposome and formulated for intravenous administration. MM-398 is indicated in combination with 5-fluorouracil and leucovorin for the treatment of patients with metastatic adenocarcinoma of the pancreas whose disease has progressed following gemcitabine-based therapy.

In one aspect, a method for treatment (e.g., effective treatment) of pancreatic cancer in a patient is provided, the method comprising: administering to the patient, and affective amount of liposomal irinotecan, wherein the method comprises at least one cycle, wherein the cycle is a period of 3 weeks, and wherein for each cycle the liposomal irinotecan is administered on day 1 of the cycle at a dose of 120 mg/m$^2$, except if the patient is homozygous for the UGT1A1*28 allele, wherein liposomal irinotecan is administered on day 1 of cycle 1 at a dose of 80 mg/m$^2$. In one embodiment, the dose of liposomal irinotecan administered to the patient homozygous for the UGT1A1*28 allele is increased after one cycle in increments of 20 mg/m², up to a maximum of 120 mg/m².

In another aspect, a method for treatment of pancreatic cancer in a patient is provided, the method comprising co-administering to the patient an effective amount each of liposomal irinotecan, 5-fluorouracil (5-FU), and leucovorin, wherein the method comprises at least one cycle of administration, wherein the cycle is a period of 2 weeks, and wherein for each cycle:

(a) liposomal irinotecan is administered to patients not homozygous for the UGT1A1*28 allele on day 1 of each cycle at a dose of 80 mg/m², and to patients homozygous for the UGT1A1*28 allele on day 1 of cycle 1 at a dose of 60 mg/m² and on day 1 of each subsequent cycle at a dose of ranging from 60 mg/m² to 80 mg/m² (e.g., 60 mg/m² or 70 mg/m² or 80 mg/m²);

(b) 5-FU is administered at a dose of 2400 mg/m²; and (c) leucovorin is administered at a dose of 200 mg/m² (l form, or levoleucovorin) or 400 mg/m² (l+d racemic form).

In one embodiment, the dose of liposomal irinotecan administered to the patient homozygous for the UGT1A1*28 allele is increased after one cycle to 80 mg/m². In one embodiment, in each cycle, the liposomal irinotecan is administered prior to the leucovorin and the leucovorin is administered prior to the 5-FU.

In another embodiment, the liposomal irinotecan is administered intravenously over 90 minutes.

In another embodiment, the 5-FU is administered intravenously over 46 hours.

In another embodiment, leucovorin is administered intravenously over 30 minutes.

In another embodiment, prior to each administration of liposomal irinotecan, the patient is pre-medicated with dexamethasone and/or a 5-HT3 antagonist or another antiemetic.

In another embodiment, the pancreatic cancer is an exocrine pancreatic cancer selected from the group consisting of acinar cell carcinoma, adenocarcinoma, adenosquamous carcinoma, giant cell tumor, intraductal papillary-mucinous neoplasm (IPMN), mucinous cystadenocarcinoma, pancreatoblastoma, serous cystadenocarcinoma, and solid and pseudopapillary tumors. Metastatic Pancreatic Cancer (mPAC) represents a significant unmet need, with approximately 80% of patients with mPAC succumbing to disease within 12 months.

In one embodiment, treating the patient results in a positive outcome, wherein the positive outcome is pathologic complete response (pCR), complete response (CR), partial response (PR) or stable disease (SD). In another embodiment, the combination therapy with liposomal irinotecan, 5-FU and leucovorin results in therapeutic synergy.

In another embodiment, the liposomal irinotecan is formulated as irinotecan sucrose octasulfate salt liposome injection (MM-398). Irinotecan sucrose octasulfate salt liposome injection may also be referred to as irinotecan HCl liposome injection because irinotecan HCl is the active pharmaceutical ingredient that is used to load irinotecan into liposomes containing triethylammonium sucrose octasulfate to prepare MM-398 liposomes. This nomenclature may be used even though the hydrochloride ion of the irinotecan HCl reacts with the triethylammonium ion of the triethylammonium sucrose octasulfate to yield triethylammonium chloride (triethylamine hydrochloride), leaving irinotecan sucrose octasulfate salt as the entrapped pharmaceutical agent within the MM-398 liposomes. In another aspect, kits for treating pancreatic cancer in a patient are provided, the kit comprising a dose of liposomal irinotecan and instructions for using liposomal irinotecan as described herein.

In another aspect, kits for treating pancreatic cancer in a patient are provided, the kit comprising a dose of each liposomal irinotecan, 5-fluorouracil (5-FU), and leucovorin, and instructions for using liposomal irinotecan, 5-FU, and leucovorin as described herein.

In one embodiment, the kit encompasses treating an exocrine pancreatic cancer selected from the group consisting of acinar cell carcinoma, adenocarcinoma, adenosquamous carcinoma, giant cell tumor, intraductal papillary-mucinous neoplasm (IPMN), mucinous cystadenocarcinoma, pancreatoblastoma, serous cystadenocarcinoma, and solid and pseudopapillary tumors.

In one embodiment, the liposomal irinotecan is liposomal irinotecan sucrose octasulfate salt injection (MM-398).

In another aspect, a formulation of liposomal irinotecan for co-administration with 5-fluorouracil (5-FU) and leucovorin in at least one cycle is provided, wherein the cycle is a period of 2 weeks, the formulation of irinotecan is a liposomal formulation of irinotecan, and wherein:

(a) liposomal irinotecan is administered to patients not homozygous for the UGT1A1*28 allele on day 1 of each cycle at a dose of 80 mg/m² and to patients homozygous for the UGT1A1*28 allele on day 1 of cycle 1 at a dose of 60 mg/m² and on day 1 of each subsequent cycle at a dose of 60 m g/m² or 80 mg/m²;

(b) 5-FU is administered at a dose of 2400 mg/m²; and (c) leucovorin is administered at a dose of 200 mg/m² (l form, or levoleucovorin) or 400 mg/m² (l+d racemic form).

In one embodiment, after cycle 1 the dose of liposomal irinotecan administered to the patient homozygous for the UGT1A1*28 allele is increased to 80 mg/m². In another embodiment, the liposomal irinotecan is administered intravenously over 90 minutes.

In another embodiment, the 5-FU is administered intravenously over 46 hours.

In another embodiment, leucovorin is administered intravenously over 30 minutes.

In another embodiment, prior to each administration of liposomal irinotecan, the patient is pre-medicated with dexamethasone and/or a 5-HT3 antagonist or another antiemetic.

In another embodiment, the pancreatic cancer is an exocrine pancreatic cancer selected from the group consisting of acinar cell carcinoma, adenocarcinoma, adenosquamous carcinoma, giant cell tumor, intraductal papillary-mucinous neoplasm (IPMN), mucinous cystadenocarcinoma, pancreatoblastoma, serous cystadenocarcinoma, and solid and pseudopapillary tumors.

In another embodiment, the liposomal formulation of irinotecan is irinotecan sucrose octasulfate salt liposome injection.

In another aspect is provided a method of improving chemotherapy outcomes by increasing tumor vascularity, the method comprising administering to a patient having a tumor an amount of irinotecan sucrose octasulfate salt liposome injection effective to increase tumor vascularity and concomitantly administering an effective amount of a chemotherapy agent other than irinotecan to the patient.

In another aspect is provided irinotecan sucrose octasulfate salt liposome injection for concomitant administration to a patient having a tumor of 1) an amount of irinotecan sucrose octasulfate salt liposome injection effective to increase tumor vascularity and 2) an effective amount of a chemotherapy agent other than irinotecan.

The therapy can be safely and effectively administered to patients diagnosed with metastatic adenocarcinoma of the pancreas after disease progression following gemcitabine-based therapy. The amount of leucovorin administered can be selected to provide a desired effect of the 5-fluorouracil (e.g., an amount of leucovorin comprising 200 mg/m$^2$ of levoleucovorin, such as 400 mg/m$^2$ of the (l+d) racemic form of leucovirin). For example, the patient can be treated with an antineoplastic therapy (referred to herein as "MM-398+5-FU/LV (MM-398 80 mg/m$^2$ q2w regimen)") comprising: 80 mg/m$^2$ of irinotecan encapsulated in a MM-398 irinotecan liposome (e.g., as a 90 minute intravenous infusion) followed by 400 mg/m$^2$ of the antineoplastic agent (l+d) racemic leucovorin (e.g., as a 30 minute intravenous infusion) followed by 2,400 mg/m$^2$ of the antineoplastic agent 5-fluorouracil (e.g., as an intravenous infusion over 46 hours), without administering any other antineoplastic agents for the treatment of the pancreatic cancer (e.g., without administering gemcitabine).

Unless otherwise indicated, recitation of the amount of the irinotecan in liposomal irinotecan is expressed herein as the amount of irinotecan hydrochloride trihydrate (molecular weight of about 677 g/mol) providing a given amount of irinotecan free base: for example, 80 mg/m$^2$ of irinotecan hydrochloride trihydrate (e.g., as approved under the non-liposomal irinotecan product CAMPTOSAR®) contains about the equivalent amount of irinotecan free base as a dose of 70 mg/m$^2$ of irinotecan in the MM-398 liposome formulation.

BRIEF DESCRIPTION OF THE DRAWINGS

FIG. 3 is a graph showing the effect of MM-398 on Carbonic Anhydrase IX Staining in a HT29 Xenograft Model.

FIG. 5 summarizes the pharmacokinetics of MM-398 in q3w (irinotecan, liposome+free drug).

FIG. 6 summarizes the pharmacokinetics of MM-398 in q3w.

FIG. 10 is a table providing the baseline characteristics of the Intent to Treat (ITT) (all randomized patients) population. In the table, CA19-9 at baseline was unknown in 3% of the patients.

FIG. 13 represents the PP population and FIG. 14 represents the Non-PP population.

FIG. 15 is a table providing the demographic characteristics for the Per Protocol (PP) patient population vs. the Non-Per Protocol (Non-PP) patient population. CA19-9 includes only patients who had a measured CA19-9 prior to treatment. "" denotes results that showed a statistically significant difference (p value≤0.01). "*" denotes the median (1st quartile, 3rd quartile).

FIG. 16 is a table providing the dose modifications and treatment exposure. Duration of exposure is the time from (the date of the last administration of the study drug+the projected days to the next dose of the study drug administration–the date of the first study drug administration).

FIG. 17 is a table providing the safety data (adverse events) for the study. In the table, (1) the safety population refers to those patients receiving at least one dose of the study drug; (2) percentages of the populations having adverse events (AE's) were provided per CTCAE Version 4; and (3) hematologic adverse events include only those patients who had at least one post-baseline assessment.

FIG. 25 is a table providing demographics and baseline characteristics (PRO Population).

FIG. 30 is a table providing Treatment-Emergent Adverse Events From the Primary Analysis of the NAPOLI-1 Trial. 5-FU is 5-flourouracil; LC is leucovorin; nal-IRI is liposomal irinotecan. Data are number of patients (%). The table shows grade 3 and 4 adverse events reported in ≥5% of patients with ≥2% incidence versus 5-FU/LV. $^a$Includes agranulocytosis, febrile neutropenia, granulocytopenia, neutropenia, neutropenic sepsis, decreased neutrophil count, and pancytopenia.

FIG. 31 is a table providing Demographics and Baseline Characteristics (Safety Population). 5-FU is 5-fluorouracil; KPS is Karnofsky performance status, LV is leucovorin, nal-IRI is liposomal irinotecan. $^a$Patients received neoadjuvant, adjuvant, or locally advanced treatment, but no previous therapy for metastatic disease. $^b$Columns add to >100% because some patients received more than 1 line of therapy, and regimens may include multiple drug classes.

FIG. 32 is a table providing TEAEs by Age. 5-FU is 5-fluorouracil; LV is leucovorin; nal-IRI is nanoliposomal irinotecan; TEAE is treatment-emergent adverse event. $^a$Dose modification included dose reduction, dose delay, and dose discontinuation. $^b$Includes agranulocytosis, febrile neutropenia, granulocytopenia, neutropenia, neutrophil sepsis, neutrophil count decreased, and pancytopenia.

FIG. 33 is a table providing TEAEs by Ethnicity. 5-FU is 5-fluorouracil; LV is leucovorin; nal-IRI is nanoliposomal irinotecan; TEAE is treatment-emergent adverse event. $^a$Dose modification included dose reduction, dose delay, and dose discontinuation. $^b$Includes agranulocytosis, febrile neutropenia, granulocytopenia, neutropenia, neutrophil sepsis, neutrophil count decreased, and pancytopenia.

FIG. 34 is a table providing TEAEs by UGT1A1*28 Allele (TA7/TA7 Genotype). 5-FU is 5-fluorouracil; LV is leucovorin; nal-IRI is nanoliposomal irinotecan; TEAE is treatment-emergent adverse event. $^a$Dose modification included dose reduction, dose delay, and dose discontinuation. $^b$Includes agranulocytosis, febrile neutropenia, granulocytopenia, neutropenia, neutrophil sepsis, neutrophil count decreased, and pancytopenia.

FIG. 35 is a table providing TEAEs by Albumin Level. 5-FU is 5-fluorouracil; LV is leucovorin; nal-IRI is nanoliposomal irinotecan; TEAE is treatment-emergent adverse event. $^a$Dose modification included dose reduction, dose delay, and dose discontinuation. $^b$Includes agranulocytosis, febrile neutropenia, granulocytopenia, neutropenia, neutrophil sepsis, neutrophil count decreased, and pancytopenia.

FIG. 36 is a table providing TEAEs by KPS Score. 5-FU is 5-fluorouracil; KPS is Karnofsky performance status; LV is leucovorin; nal-IRI is nanoliposomal irinotecan; TEAE is treatment-emergent adverse event. $^a$Dose modification included dose reduction, dose delay, and dose discontinuation. $^b$Includes agranulocytosis, febrile neutropenia, granulocytopenia, neutropenia, neutrophil sepsis, neutrophil count decreased, and pancytopenia.

DETAILED DESCRIPTION

I. Definitions

Figure 1:
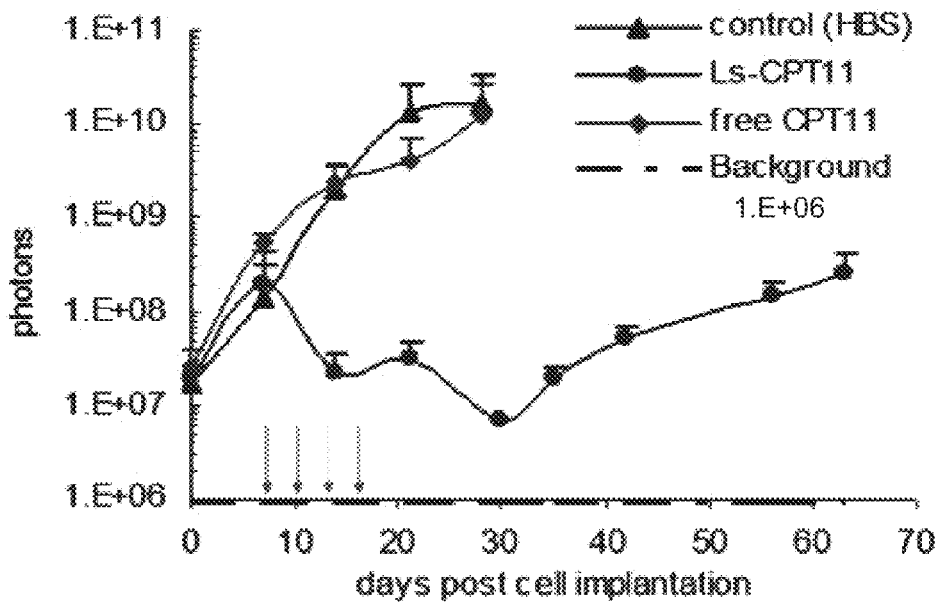
FIG. 1 is a graph showing the anti-tumor activity of MM-398 in an orthotopic pancreatic tumor model expressing luciferase (L3.6pl).

As used herein, the term "subject" or "patient" is a human cancer patient.

As used herein, "effective treatment" refers to treatment producing a beneficial effect, e.g., amelioration of at least one symptom of a disease or disorder. A beneficial effect can take the form of an improvement over baseline, i.e., an improvement over a measurement or observation made prior to initiation of therapy according to the method. A beneficial effect can also take the form of arresting, slowing, retarding, or stabilizing of a deleterious progression of a marker of a cancer. Effective treatment may refer to alleviation of at least one symptom of a cancer. Such effective treatment may, e.g., reduce patient pain, reduce the size and/or number of lesions, may reduce or prevent metastasis of a cancer tumor, and/or may slow growth of a cancer tumor.

The term "effective amount" refers to an amount of an agent that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In reference to cancers, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay tumor development. In some embodiments, an effective amount is an amount sufficient to prevent or delay tumor recurrence. An effective amount can be administered in one or more administrations. The effective amount of the drug or composition may: (i) reduce the number of cancer cells; (ii) reduce tumor size; (iii) inhibit, retard, slow to some extent and may stop cancer cell infiltration into peripheral organs; (iv) inhibit (i.e., slow to some extent and may stop) tumor metastasis; (v) inhibit tumor growth; (vi) prevent or delay occurrence and/or recurrence of tumor; and/or (vii) relieve to some extent one or more of the symptoms associated with the cancer.

The terms "combination therapy," "co-administration," "co-administered" or "concurrent administration" (or minor variations of these terms) include simultaneous administration of at least two therapeutic agents to a patient or their sequential administration within a time period during which the first administered therapeutic agent is still present in the patient when the second administered therapeutic agent is administered.

The term "monotherapy" refers to administering a single drug to treat a disease or disorder in the absence of co-administration of any other therapeutic agent that is being administered to treat the same disease or disorder.

"Dosage" refers to parameters for administering a drug in defined quantities per unit time (e.g., per hour, per day, per week, per month, etc.) to a patient. Such parameters include, e.g., the size of each dose. Such parameters also include the configuration of each dose, which may be administered as one or more units, e.g., taken at a single administration, e.g., orally (e.g., as one, two, three or more pills, capsules, etc.) or injected (e.g., as a bolus). Dosage sizes may also relate to doses that are administered continuously (e.g., as an intravenous infusion over a period of minutes or hours). Such parameters further include frequency of administration of separate doses, which frequency may change over time.

"Dose" refers to an amount of a drug given in a single administration.

As used herein, "cancer" refers to a condition characterized by abnormal, unregulated, malignant cell growth. In one embodiment, the cancer is an exocrine pancreatic cancer. In another embodiment, the exocrine pancreatic cancer selected from the group consisting of acinar cell carcinoma, adenocarcinoma, adenosquamous carcinoma, giant cell tumor, intraductal papillary-mucinous neoplasm (IPMN), mucinous cystadenocarcinoma, pancreatoblastoma, serous cystadenocarcinoma, and solid and pseudopapillary tumors.

The terms "resistant" and "refractory" refer to tumor cells that survive treatment with a therapeutic agent. Such cells may have responded to a therapeutic agent initially, but subsequently exhibited a reduction of responsiveness during treatment, or did not exhibit an adequate response to the therapeutic agent in that the cells continued to proliferate in the course of treatment with the agent.

II. Irinotecan Nanoparticle Formulations

As provided herein, irinotecan is administered in a composition of irinotecan nanoparticles with a diameter of about 80-140 nm formulated to provide an irinotecan terminal elimination half-life in the human patient of at least about 2-fold higher than that of 125 mg/m² free irinotecan as CPT-11 irinotecan hydrochloride injection, and preferably also include a $C_{max}$ and AUC within the ranges specified in Table 4. Preferably, the irinotecan is contained within a lipid matrix, for example as described in PCT publication WO2005/107712 (see, e.g., Example 11 describing CPT-11 liposome formulations prepared with TEA-Pn and TEA-SOS, incorporated herein by reference). The lipid matrix composition can comprise entrapped irinotecan in a pharmaceutically acceptable salt form, in 1,2-Distearoyl-SN-phosphatidylcholine (DSPC) (Mol. wt. 790) 3 molar parts (59.8 mol. %); Cholesterol (Chol) (Mol. weight 387) 2 molar parts (39.9 mol. %); and N-(omega-methoxy-poly(ethylene glycol)-oxycarbonyl)-1,2-distearoylphosphatidyl ethanolamine (Mol. weight 2787) (PEG-DSPE) 0.015 molar parts (approx. 0.3 mol. %).

Figure 18:
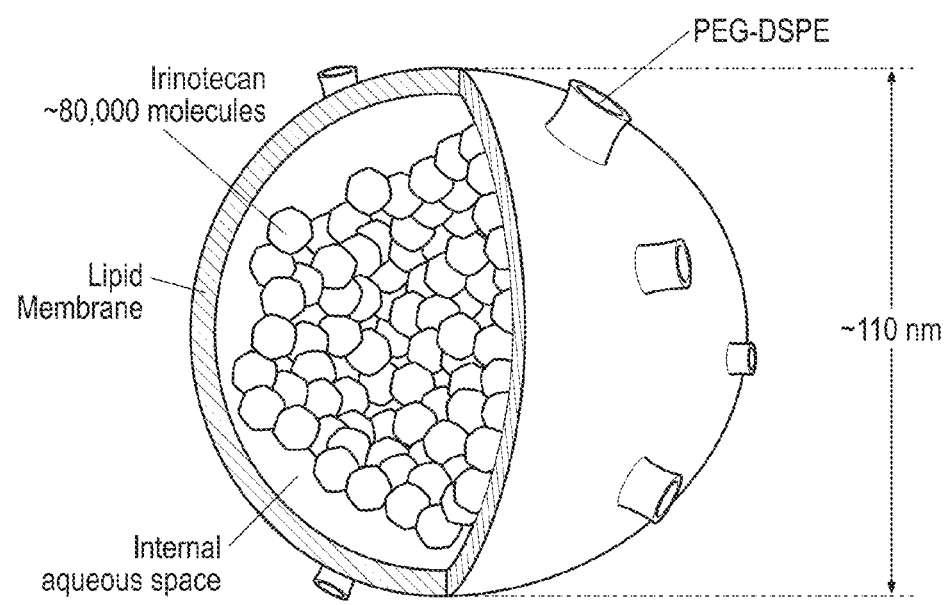
FIG. 18 is a pictorial representation of nanoliposomal irinotecan (MM-398).
Figure 19:
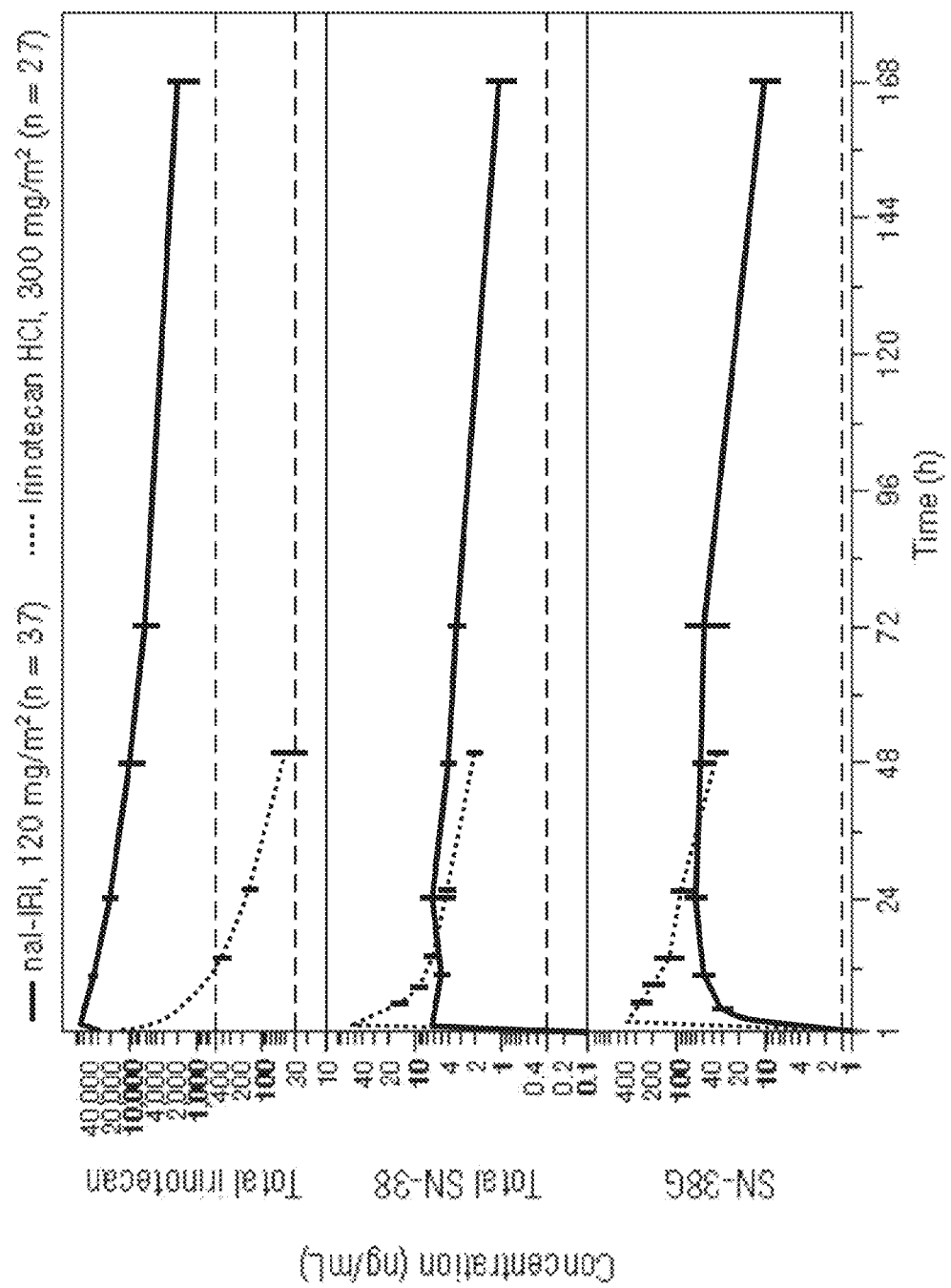
FIG. 19 provides a pharmacokinetic analysis of the extended circulation of irinotecan and the SN38 metabolite after administration of irinotecan within the liposome vs. irinotecan HCl, in patients with gastric cancer. Nal-IRI is nanoliposomal Irinotecan; AUC is area under the curve; $C_{max}$ is maximal concentration. Comparing nal-IRI with irinotecan HCl, total irinotecan AUC was 46 times greater and total irinotecan $C_{max}$ was 13.4 times greater, SN-38 AUC was 1.4 times greater, and SN-38 $C_{max}$ was 0.19 times greater. The peak of SN-38 metabolite was lower with nal-IRI versus irinotecan HCl, without an increase in SN-38 plasma AUC.
Figure 20:
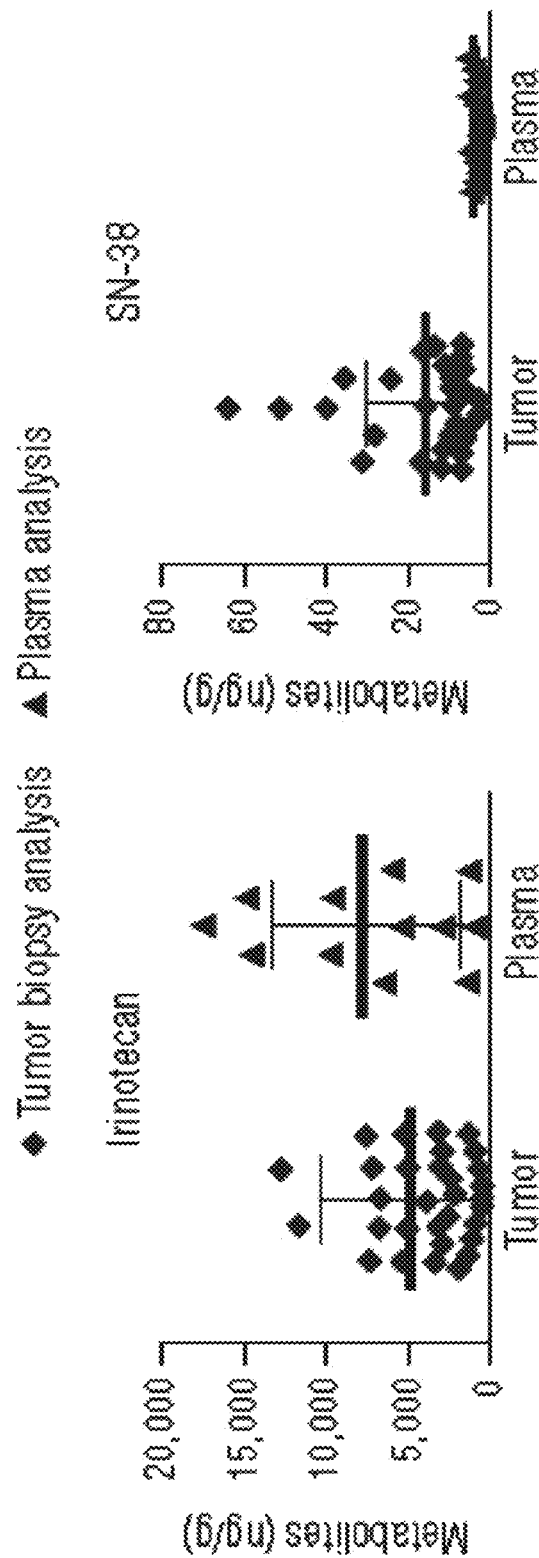
FIG. 20 provides irinotecan and SN38 levels in tumor tissue and plasma 72 hours after treatment with MM-398. Nal-IRI is nanoliposomal irinotecan; LLoQ is lower limit of quantitation. Drug metabolite quantitation in tumor biopsies and plasma from patients in a study of patients (N=14) with advanced solid tumors. Tumor biopsy material averaged 10.5 mg (range, 3.3-21.9 mg); metabolite detection was in an LC/MS/MS TSQ Vantage instrument, with LLoQ of 50 pg/mL for irinotecan and 100 pg/mL for SN-38. Plasma analysis was performed at QPS according to validated procedures, with LLoQ of 140 ng/mL for irinotecan and 600 pg/mL for SN-38.

In some embodiments, the irinotecan is administered in a lipid matrix as a liposomal formulation encapsulating irinotecan sucrose sulfate liposome. The liposome can have the structure shown in FIG. 18. For example, the irinotecan nanoparticle can be an "irinotecan sucrose octasulfate salt liposome injection" or "irinotecan sucrosofate liposome injection" product, including the formulation referred to herein as "MM-398" (also known as PEPO2 or nanoliposomal irinotecan or liposomal irinotecan or "nal-IRI").

For example, an MM-398 liposome is a unilamellar lipid bilayer vesicle of approximately 80-140 nm in diameter that encapsulates an aqueous space which contains irinotecan complexed in a gelated or precipitated state as a salt with sucrose octasulfate. The lipid membrane of the liposome is composed of phosphatidylcholine, cholesterol, and a polyethyleneglycol-derivatized phosphatidyl-ethanolamine in the amount of approximately one polyethyleneglycol (PEG) molecule for 200 phospholipid molecules.

This stable liposomal formulation of irinotecan has several attributes that may provide an improved therapeutic index. The controlled and sustained release improves activity of this schedule-dependent drug by increasing duration of exposure of tumor tissue to drug, an attribute that allows it to be present in a higher proportion of cells during the S-phase of the cell cycle, when DNA unwinding is required as a preliminary step in the DNA replication process. The long circulating pharmacokinetics and high intravascular drug retention in the liposomes can promote an enhanced permeability and retention (EPR) effect. EPR allows for deposition of the liposomes at sites, such as malignant tumors, where the normal integrity of the vasculature (capillaries in particular) is compromised resulting in leakage out of the capillary lumen of particulates such as liposomes. EPR may thus promote site-specific drug delivery of liposomes to solid tumors. EPR of MM-398 may result in a subsequent depot effect, where liposomes accumulate in tumor associated macrophages (TAMs), which metabolize irinotecan, converting it locally to the substantially more cytotoxic SN-38. This local bioactivation is believed to result in reduced drug exposure at potential sites of toxicity and increased exposure at cancer cells within the tumor.

The chemical name of irinotecan hydrochloride trihydrate is (S) 4,11-diethyl-3,4,12,14-tetrahydro-4-hydroxy-3,14-dioxolH-pyrano[3',4':6,7]-indolizino[1,2b]quinolin-9-yl-[1, 4'bipiperidine]-1'-carboxylate, monohydrochloride, trihydrate. The empirical formula is $C_{33}H_{38}N_4O_6 \cdot HCl \cdot 3H_2O$ and the molecular weight is 677.19 g/mole. The molecular structure is:

Structural Formula:

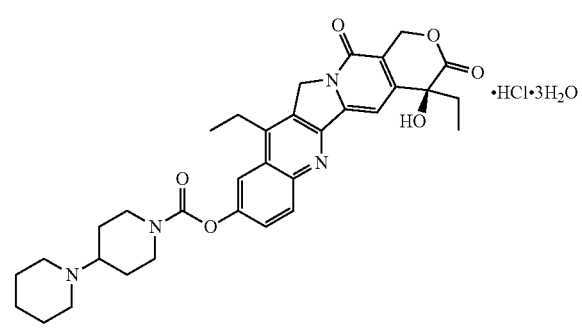 [SMILES: CCc1c2c(nc3ccc(OC(=O)N4CCC(N5CCCCC5)CC4)cc13)-c1cc3c(c(=O)n1C2)COC(=O)[C@]3(O)CC]

The chemical name of irinotecan is (S) 4,11-diethyl-3,4, 12,14-tetrahydro-4-hydroxy-3,14-dioxolH-pyrano[3',4':

6,7]-indolizino[1,2b]quinolin-9-yl-[1,4'bipiperidine]-1'-carboxylate. The empirical formula is $C_{33}H_{38}N_4O_6$ and the molecular weight is 586.68 g/mole. The molecular structure of irinotecan free base is:

structural Formula:

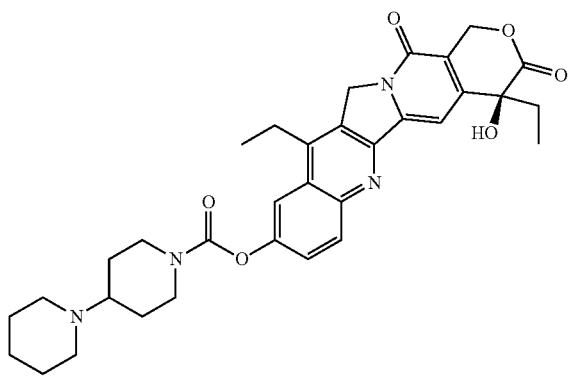 [SMILES: CCc1c2c(nc3ccc(OC(=O)N4CCC(N5CCCCC5)CC4)cc13)-c1cc3c(c(=O)n1C2)COC(=O)[C@]3(O)CC]

MM-398 is a topoisomerase I inhibitor indicated for the treatment of metastatic adenocarcinoma of the pancreas after disease progression following gemcitabine-based therapy. MM-398 (irinotecan liposome injection), in combination with 5-fluorouracil and leucovorin, is indicated for the treatment of patients with metastatic adenocarcinoma of the pancreas whose disease has progressed following gemcitabine-based therapy. Administer MM-398 prior to leucovorin and 5-fluorouracil. MM-398 is not indicated as a single agent for the treatment of metastatic adenocarcinoma of the pancreas. MM-398 is not substituted for other drugs containing non-liposome formulations of irinotecan hydrochloride or irinotecan hydrochloride trihydrate.

Converting a dose based on irinotecan hydrochloride trihydrate to a dose based on irinotecan free base is accomplished by multiplying the dose based on irinotecan hydrochloride trihydrate with the ratio of the molecular weight of irinotecan free base (586.68 g/mol) and the molecular weight of irinotecan hydrochloride trihydrate (677.19 g/mol). This ratio is 0.87 which can be used as a conversion factor. For example, an 80 mg/m² dose based on irinotecan hydrochloride trihydrate is equivalent to a 69.60 mg/m² dose based on irinotecan free base (80×0.87). In the clinic this is rounded to 70 mg/m².

Alternatively, the dose of irinotecan liposome can be expressed as the amount of irinotecan free base encapsulated in the irinotecan liposome where indicated ("free base dose"). Unless otherwise indicated, the irinotecan liposome dose free base dose recited in MM-398 is expressed in terms of the amount of irinotecan hydrochloride trihydrate salt (herein referred to as a "(salt)" dose) containing the same amount of irinotecan free base. Examples of equivalent MM-398 doses are provided in table 1 below based on both free base dose and salt based dose.

TABLE 1

| Irinotecan liposome free base dose in MM-398 (mg/m²) ("free base") | Corresponding MM-398 irinotecan liposome hydrochloride trihydrate salt dose (mg/m²) ("salt") |
| --- | --- |
| 100 | 120 |
| 70 | 80 |
| 60 | 70 |
| 50 | 60 |

TABLE 1-continued

| Irinotecan liposome free base dose in MM-398 (mg/m²) ("free base") | Corresponding MM-398 irinotecan liposome hydrochloride trihydrate salt dose (mg/m²) ("salt") |
| --- | --- |
| 43 | 50 |
| 35 | 40 |

The recommended dose of MM-398 is 80 mg/m² (salt) (70 mg/m² free base) intravenous infusion over 90 minutes (i.e., 70 mg irinotecan free base in the irinotecan liposome per m² patient body surface area, containing about the same amount of irinotecan that would be in 80 mg/m² of irinotecan hydrochloride trihydrate). Preferably, the recommended dose of MM-398 is 80 mg/m² administered by intravenous infusion over 90 minutes every 2 weeks. A corticosteroid and an anti-emetic is preferably administered to the patient 30 minutes prior to MM-398.

Pharmacogenetics of Irinotecan Glucuronidation

The enzyme produced by the UGT1A1 gene, UDP-glucuronosyltransferase 1, is responsible for bilirubin metabolism and also mediates SN-38 glucuronidation, which is the initial step in the predominant metabolic clearance pathway of this active metabolite of irinotecan. Besides its anti-tumor activity, SN-38 is also responsible for the severe toxicity sometimes associated with irinotecan therapy. Therefore, the glucuronidation of SN-38 to the inactive form, SN-38 glucuronide, is an important step in the modulation of irinotecan toxicity.

Mutational polymorphisms in the promoter of the UGT1A1 gene have been described in which there is a variable number of thymine adenine (ta) repeats. Promoters containing seven thymine adenine (ta) repeats (found in the UGT1A1*28 allele) have been found to be less active than the wild-type six repeats, resulting in reduced expression of UDP-glucuronosyltransferase 1. Patients who carry two deficient alleles of UGT1A1 exhibit reduced glucuronidation of SN-38. Some case reports have suggested that individuals who are homozygous for UGT1A1*28 alleles (referred to as having the UGT1A1 7/7 genotype, because both alleles are UGT1A1*28 alleles that contain 7 ta repeats, as opposed to the wild-type UGT1A1 6/6 genotype in which both alleles contain 6 ta repeats) and who have fluctuating elevation in serum bilirubin, (e.g., Gilbert's Syndrome patients), may be at greater risk of toxicity upon receiving standard doses of irinotecan. This suggests that there is a link between homozygosity of the UGT1A1*28 allele, bilirubin levels and irinotecan toxicity.

The metabolic transformation of MM-398 to SN-38 (e.g., in plasma) includes two critical steps: (1) the release of irinotecan from the liposome and (2) the conversion of free irinotecan to SN-38. While not intending to be limited by theory, it is believed that once irinotecan leaves the liposomes, it is catabolized by the same metabolic pathways as conventional (free) irinotecan. Therefore the genetic polymorphisms in humans predictive for the toxicity and efficacy of irinotecan and those of MM-398 can be considered similar. Nonetheless, due to the smaller tissue distribution, lower clearance, higher systemic exposure and longer elimination half-life of SN-38 of the MM-398 formulation compared to free irinotecan, the deficient genetic polymorphisms may show more association with severe adverse events and/or efficacy.

Patients with Reduced UGT1A1 Activity

Individuals who are homozygous for the UGT1A1*28 allele (UGT1A1 7/7 genotype) have been shown to be at increased risk for neutropenia following initiation of irinotecan treatment. According to the prescribing information for irinotecan (Camptosar®), in a study of 66 patients who received single-agent irinotecan (350 mg/m$^2$ once every-3-weeks), the incidence of grade 4 neutropenia in patients homozygous for the UGT1A1*28 allele was as high as 50%, and in patients heterozygous for this allele (UGT1A1 6/7 genotype) the incidence was 12.5%. Importantly, no grade 4 neutropenia was observed in patients homozygous for the wild-type allele (UGT1A1 6/6 genotype). In other studies, a lower prevalence of life threatening neutropenia is described. For this reason, patients who are enrolled in the phase 3 study described in the Examples herein and are homozygous for the UGT1A1*28 allele (UGT1A1 7/7 genotype) will have MM-398 treatment initiated at a lower dose than patients with one (e.g., UGT1A1 6/7) or two (UGT1A1 6/6) wild-type alleles.

The recommended starting dose of MM-398 in patients known to be homozygous for the UGT1A1*28 allele is 60 mg/m$^2$ (salt) (equivalent to a dose of 50 mg/m$^2$ (base)) administered by intravenous infusion over 90 minutes. Increase the dose of MM-398 to 80 mg/m$^2$ (salt) as tolerated in subsequent cycles.

In some embodiments, methods of administering MM-398 to patients having one or more characteristics can include reducing or otherwise modifying the dose of MM-398 administered according to the embodiments herein. In some embodiments, the dose of MM-398 is modified according to Table 2.

TABLE 2

Recommended Dose Modifications for MM-398 (salt)

| Toxicity NCI CTCAE v4.0 | | MM-398 adjustment in patients receiving 80 mg/m$^{2\ddagger}$ (salt) | Patients homozygous for UGT1A1*28 without previous increase to 80 mg/m$^2$ (salt) |
|---|---|---|---|
| Grade 3 or 4 adverse reactions | Occurrence | Withhold MM-398. Initiate loperamide for late onset diarrhea of any severity. Administer intravenous or subcutaneous atropine 0.25 to 1 mg (unless clinically contraindicated) for early onset diarrhea of any severity. Upon recovery to ≤Grade 1 or baseline grade resume MM-398 at: | |
| | First | 60 mg/m$^2$ | 50 mg/m$^2$ |
| | Second | 50 mg/m$^2$ | 40 mg/m$^2$ |
| | Third | Discontinue MM-398 | Discontinue MM-398 |
| Interstitial Lung Disease | First | Discontinue MM-398 | Discontinue MM-398 |
| Anaphylactic Reaction | First | Discontinue MM-398 | Discontinue MM-398 |

Additional Genotypic Modifiers of Irinotecan Metabolism

Although the UGT1A1*28 allele is relatively common in Caucasians (estimates 10%), the prevalence is varied in other ethnic groups. Furthermore, additional UGT1A1 genotypes are found with higher prevalence for example in Asian populations and these could be important for the metabolism of irinotecan in these populations. For example, the UGT1A1*6 allele is more prevalent in Asians. This allele is not associated with a to repeat, but with a Gly71Arg mutation that reduces enzyme activity. In previous and ongoing studies of MM-398, pharmacogenetic information has been collected on patients being enrolled. In a study referred to as the PEP0203 study, the relationship of genetic polymorphism of UGT1A family and of DPYD (dihydropyrimidine dehydrogenase, an enzyme associated with catabolism of 5-FU) with pharmacokinetic parameters of MM-398 and toxicity did not provide a clear correlation with the small sample size of subjects evaluated. However, it was observed that patients with UGT1A1*6/*28 combined polymorphism had higher dose-normalized AUCs of SN-38 and experienced DLT.

III. 5-Fluorouracil (5-FU) and Leucovorin

5-Fluorouracil is a pyrimidine antagonist that interferes with nucleic acid biosynthesis. The deoxyribonucleotide of the drug inhibits thymidylate synthetase, thus inhibiting the formation of thymidylic acid from deoxyuridylic acid, thus interfering in the synthesis of DNA. It also interferes with RNA synthesis.

Leucovorin (also called folinic acid) acts as a biochemical cofactor for 1-carbon transfer reactions in the synthesis of purines and pyrimidines. Leucovorin does not require the enzyme dihydrofolate reductase (DHFR) for conversion to tetrahydrofolic acid. The effects of methotrexate and other DHFR-antagonists are inhibited by leucovorin. Leucovorin can potentiate the cytotoxic effects of fluorinated pyrimidines (i.e., 5-fluorouracil and floxuridine). After 5-FU is activated within the cell, it is accompanied by a folate cofactor, and inhibits the enzyme thymidylate synthetase, thus inhibiting pyrimidine synthesis. Leucovorin increases the folate pool, thereby increasing the binding of folate cofactor and active 5-FU with thymidylate synthetase.

Leucovorin has dextro- and levo-isomers, only the latter one being pharmacologically useful. As such, the bioactive levo-isomer ("levoleucovorin") has also been approved by the FDA for treatment of cancer. The dosage of levoleucovorin is typically half that of the racemic mixture containing both dextro (d) and levo (l) isomers. Unless otherwise indicated, doses requiring 200 mg/m$^2$ leucovorin are to be understood to require 200 mg/m$^2$ of the (1) enantiomer of leucovorin, and doses requiring 400 mg/m$^2$ leucovorin are to be understood to require 400 mg/m$^2$ of the (l+d) racemate of leucovorin. Unless otherwise indicated, a dose having 200 mg/m$^2$ of the (l) enantiomer of leucovorin, and a dose having 400 mg/m$^2$ of the (l+d) racemate of leucovorin contain equivalent amounts of the pharmaceutically active (l) form of leucovorin.

FU and leucovorin will be stored and handled according to the country specific package inserts.

IV. Administration

Liposomal irinotecan is administered intravenously, either alone or in combination with 5-fluorouracil (5-FU) and/or leucovorin. In one embodiment, liposomal irinotecan is administered prior to 5-FU and leucovorin. In another embodiment, leucovorin is administered prior to 5-FU. In another embodiment, liposomal irinotecan is administered intravenously over 90 minutes. In another embodiment, 5-FU is administered intravenously over 46 hours. In another embodiment, leucovorin is administered intravenously over 30 minutes. In various embodiments the liposomal irinotecan is MM-398.

V. Patient Populations

In one embodiment, a patient treated using the methods and compositions disclosed herein exhibits evidence of recurrent or persistent pancreatic cancer following primary chemotherapy.

In another embodiment, the patient has had and failed at least one prior platinum based chemotherapy regimen for management of primary or recurrent disease, e.g., a chemotherapy regimen comprising carboplatin, cisplatin, or another organoplatinum compound.

In an additional embodiment, the patient has failed prior treatment with gemcitabine or become resistant to gemcitabine.

In one embodiment a resistant or refractory tumor is one where the treatment-free interval following completion of a course of therapy for a patient having the tumor is less than 6 months (e.g., owing to recurrence of the cancer) or where there is tumor progression during the course of therapy.

In another embodiment, the pancreatic cancer of the patient undergoing treatment is advanced pancreatic cancer, which is a pancreatic tumor that exhibits either or both of distant metastasis or peripancreatic extension of the tumor.

The compositions and methods disclosed herein are useful for the treatment of all pancreatic cancers, including pancreatic cancers that are refractory or resistant to other anti-cancer treatments.

VI. Combination Therapy

In one embodiment, liposomal irinotecan is co-administered to patients having pancreatic cancer in combination with 5-fluorouracil (5-FU) and leucovorin, according to a particular clinical dosage regimen, such as those described herein. In one embodiment, the liposomal irinotecan is MM-398.

As used herein, adjunctive or combined administration (coadministration) includes simultaneous administration of the compounds in the same or different dosage form, or separate administration of the compounds (e.g., sequential administration). For example, liposomal irinotecan can be simultaneously administered with 5-FU and leucovorin. Alternatively, liposomal irinotecan can be administered in combination with 5-FU and leucovorin, wherein liposomal irinotecan, 5-FU and leucovorin are formulated for separate administration and are administered concurrently or sequentially. For example, liposomal irinotecan can be administered first followed by (e.g., immediately followed by) the administration of the 5-FU and leucovorin. Such concurrent or sequential administration preferably results in liposomal irinotecan, 5-FU, and leucovorin being simultaneously present in treated patients. In a particular embodiment, liposomal irinotecan is administered prior to 5-FU and leucovorin. In another particular embodiment, leucovorin is administered prior to 5-FU.

In another embodiment, liposomal irinotecan, 5-FU, and leucovorin are formulated for intravenous administration. In a particular embodiment, the patient is administered an effective amount each of liposomal irinotecan, 5-fluorouracil (5-FU), and leucovorin, wherein the treatment comprises at least one cycle, wherein the cycle is a period of 2 weeks, and wherein for each cycle: (a) liposomal irinotecan is administered on day 1 of the cycle at a dose of 80 mg/m$^2$, except if the patient is homozygous for the UGT1A1*28 allele, wherein liposomal irinotecan is administered on day 1 of cycle 1 at a dose of 60 mg/m$^2$; (b) 5-FU is administered at a dose of 2400 mg/m$^2$; and (c) leucovorin is administered at a dose of 200 mg/m$^2$ (1 form) or 400 mg/m$^2$ (l+d racemic form) In a particular embodiment, the dose of liposomal irinotecan administered to the patient homozygous for the UGT1A1*28 allele is increased after one cycle to 80 mg/m$^2$.

In one embodiment, liposomal irinotecan may be initially administered at a high dose and may be lowered over time. In another embodiment, liposomal irinotecan is initially administered at a low dose and increased over time. In one embodiment, liposomal irinotecan is administered as a monotherapy.

In another embodiment, the dose of 5-FU is varied over time. For example, 5-FU may be initially administered at a high dose and may be lowered over time. In another embodiment, 5-FU is initially administered at a low dose and increased over time.

In another embodiment, the dose of leucovorin is varied over time. For example, leucovorin may be initially administered at a high dose and may be lowered over time. In another embodiment, leucovorin is initially administered at a low dose and increased over time.

VII. Treatment Protocols

Other treatment protocols include, for example, those wherein the patient is administered an effective amount of liposomal irinotecan, wherein the treatment comprises at least one cycle, wherein the cycle is a period of 3 weeks, and wherein for each cycle the liposomal irinotecan is administered on day 1 of the cycle at a dose of 120 mg/m$^2$, except if the patient is homozygous for the UGT1A1*28 allele, wherein liposomal irinotecan is administered on day 1 of cycle 1 at a dose of 80 mg/m$^2$. In one embodiment, the dose of liposomal irinotecan administered to the patient homozygous for the UGT1A1*28 allele is increased after one cycle in increments of 20 mg/m$^2$, up to a maximum of 120 mg/m$^2$.

In another embodiment, the treatment protocol includes administering to the patient an effective amount each of liposomal irinotecan, 5-fluorouracil (5-FU), and leucovorin, wherein the treatment comprises at least one cycle, wherein the cycle is a period of 2 weeks, and wherein for each cycle: (a) liposomal irinotecan is administered on day 1 of the cycle at a dose of 80 mg/m$^2$, except if the patient is homozygous for the UGT1A1*28 allele, wherein liposomal irinotecan is administered on day 1 of cycle 1 at a dose of 60 mg/m$^2$; (b) 5-FU is administered at a dose of 2400 mg/m$^2$; and (c) leucovorin is administered at a dose of 200 mg/m$^2$ (1 form) or 400 mg/m$^2$ (1+d racemic form). In a particular embodiment, the dose of liposomal irinotecan administered to the patient homozygous for the UGT1A1*28 allele is increased after one cycle to 80 mg/m$^2$.

VIII. Outcomes

Provided herein are methods for treating pancreatic cancer in a patient comprising administering to the patient liposomal irinotecan (MM-398), alone or in combination with 5-fluorouracil (5-FU) and leucovorin, according to a particular clinical dosage regimen. Preferably, the combination therapy with liposomal irinotecan with 5-FU and leucovorin exhibits therapeutic synergy.

"Therapeutic synergy" refers to a phenomenon where treatment of patients with a combination of therapeutic agents manifests a therapeutically superior outcome to the outcome achieved by each individual constituent of the combination used at its optimum dose (T. H. Corbett et al., 1982, Cancer Treatment Reports, 66, 1187). In this context a therapeutically superior outcome is one in which the patients either a) exhibit fewer incidences of adverse events while receiving a therapeutic benefit that is equal to or greater than that where individual constituents of the combination are each administered as monotherapy at the same dose as in the combination, or b) do not exhibit dose-limiting toxicities while receiving a therapeutic benefit that is greater than that of treatment with each individual constituent of the combination when each constituent is administered in at the same doses in the combination(s) as is administered as individual components. In xenograft models, a combination, used at its maximum tolerated dose, in which each of the constituents will be present at a dose generally not exceeding its individual maximum tolerated dose, manifests therapeutic synergy when decrease in tumor growth achieved by administration of the combination is greater than the value of the decrease in tumor growth of the best constituent when the constituent is administered alone.

Thus, in combination, the components of such combinations have an additive or superaddictive effect on suppressing pancreatic tumor growth, as compared to monotherapy with liposome-encapsulated irinotecan alone or treatment with the chemotherapeutic(s) in the absence of liposomal irinotecan therapy. By "additive" is meant a result that is greater in extent (e.g., in the degree of reduction of tumor mitotic index or of tumor growth or in the degree of tumor shrinkage or the frequency and/or duration of symptom-free or symptom-reduced periods) than the best separate result achieved by monotherapy with each individual component, while "superaddictive" is used to indicate a result that exceeds in extent the sum of such separate results. In one embodiment, the additive effect is measured as slowing or stopping of pancreatic tumor growth. The additive effect can also be measured as, e.g., reduction in size of a pancreatic tumor, reduction of tumor mitotic index, reduction in number of metastatic lesions over time, increase in overall response rate, or increase in median or overall survival.

One non-limiting example of a measure by which effectiveness of a therapeutic treatment can be quantified is by calculating the log 10 cell kill, which is determined according to the following equation:

$$\log 10 \text{ cell kill} = TC(\text{days})/3.32 \times Td$$

in which T C represents the delay in growth of the cells, which is the average time, in days, for the tumors of the treated group (T) and the tumors of the control group (C) to have reached a predetermined value (1 g, or 10 mL, for example), and Td represents the time, in days necessary for the volume of the tumor to double in the control animals. When applying this measure, a product is considered to be active if log 10 cell kill is greater than or equal to 0.7 and a product is considered to be very active if log 10 cell kill is greater than 2.8. Using this measure, a combination, used at its own maximum tolerated dose, in which each of the constituents is present at a dose generally less than or equal to its maximum tolerated dose, exhibits therapeutic synergy when the log 10 cell kill is greater than the value of the log 10 cell kill of the best constituent when it is administered alone. In an exemplary case, the log 10 cell kill of the combination exceeds the value of the log 10 cell kill of the best constituent of the combination by at least 0.1 log cell kill, at least 0.5 log cell kill, or at least 1.0 log cell kill.

Responses to therapy may include:
Pathologic complete response (pCR): absence of invasive cancer in the breast and lymph nodes following primary systemic treatment.
Complete Response (CR): Disappearance of all target lesions. Any pathological lymph nodes (whether target or non-target) which has reduction in short axis to <10 mm;
Partial Response (PR): At least a 30% decrease in the sum of dimensions of target lesions, taking as reference the baseline sum diameters;
Stable Disease (SD): Neither sufficient shrinkage to qualify for partial response, nor sufficient increase to qualify for progressive disease, taking as reference the smallest sum diameters while on study; or
Meanwhile, non-CR/Non-PD denotes a persistence of one or more non-target lesion(s) and/or maintenance of tumor marker level above the normal limits.
Progressive Disease (PD) denotes at least a 20% increase in the sum of dimensions of target lesions, taking as reference the smallest sum on study (this includes the baseline sum if that is the smallest on study). In addition to the relative increase of 20%, the sum must also demonstrate an absolute increase of 5 mm. The appearance of one or more new lesions is also considered progression.

In exemplary outcomes, patients treated according to the methods disclosed herein may experience improvement in at least one sign of pancreatic cancer.

In one embodiment the patient so treated exhibits pCR, CR, PR, or SD.

In another embodiment, the patient so treated experiences tumor shrinkage and/or decrease in growth rate, i.e., suppression of tumor growth. In another embodiment, unwanted cell proliferation is reduced or inhibited. In yet another embodiment, one or more of the following can occur: the number of cancer cells can be reduced; tumor size can be reduced; cancer cell infiltration into peripheral organs can be inhibited, retarded, slowed, or stopped; tumor metastasis can be slowed or inhibited; tumor growth can be inhibited; recurrence of tumor can be prevented or delayed; one or more of the symptoms associated with cancer can be relieved to some extent.

In other embodiments, such improvement is measured by a reduction in the quantity and/or size of measurable tumor lesions. Measurable lesions are defined as those that can be accurately measured in at least one dimension (longest diameter is to be recorded) as ≥10 mm by CT scan (CT scan slice thickness no greater than 5 mm), 10 mm caliper measurement by clinical exam or >20 mm by chest X-ray. The size of non-target lesions, e.g., pathological lymph nodes can also be measured for improvement. In one embodiment, lesions can be measured on chest x-rays or CT or MM films.

In other embodiments, cytology or histology can be used to evaluate responsiveness to a therapy. The cytological confirmation of the neoplastic origin of any effusion that appears or worsens during treatment when the measurable tumor has met criteria for response or stable disease can be considered to differentiate between response or stable disease (an effusion may be a side effect of the treatment) and progressive disease.

In some embodiments, administration of effective amounts of liposomal irinotecan, 5-FU and leucovorin according to any of the methods provided herein produce at least one therapeutic effect selected from the group consisting of reduction in size of a breast tumor, reduction in number of metastatic lesions appearing over time, complete remission, partial remission, stable disease, increase in overall response rate, or a pathologic complete response. In some embodiments, the provided methods of treatment produce a comparable clinical benefit rate (CBR=CR+PR+SD≥6 months) better than that achieved by the same combinations of anti-cancer agents administered without concomitant MM-398 administration. In other embodiments, the improvement of clinical benefit rate is about 20%, 30%, 40%, 50%, 60%, 70%, 80% or more compared to the same combinations of anti-cancer agents administered without concomitant MM-398 administration.

The following examples are illustrative and should not be construed as limiting the scope of this disclosure in any way; many variations and equivalents will become apparent to those skilled in the art upon reading the present disclosure.

EXAMPLES

Example 1: Activity of MM-398 in an Orthotopic Pancreas Tumor Model Expressing Luciferase (L3.6pl)

The anti-tumor activity of MM-398 was assessed in an orthotopic pancreatic cancer model (L3.6pl), a highly hypoxic preclinical tumor model. Approximately $2.5 \times 10^{-5}$ L3.6pl pancreatic tumor cells were implanted by direct injection into the pancreas. The bioluminescence images (BLI) were followed over time for tumor burden detection/quantitation. MM-398 and free irinotecan were dosed at a dose of 20 mg/kg/dose weekly for three weeks. As shown in FIG. 1, MM-398 (liposomal CPT11) had significant anti-tumor activity, as compared to a control (HBS) and free CPT11.

Example 2: Accumulation of SN-38 in Tumors Following Treatment with Free Irinotecan or Liposomal Irinotecan (MM-398)

It was hypothesized that the anti-tumor activity observed in the orthotopic pancreatic cancer model is due to the effect of macrophages in converting irinotecan to the more active SN-38 locally. To test this hypothesis, human colon cancer cells (HT-29) were injected subcutaneously into SCID mice, 40 mg/kg of free irinotecan or MM-398 was injected intravenously when the tumors reached 1000 mm$^3$ in size. Tumor-bearing mice were sacrificed at different time points, tumors from both groups were extracted and the concentrations of SN-38 were measured.

Figure 2:
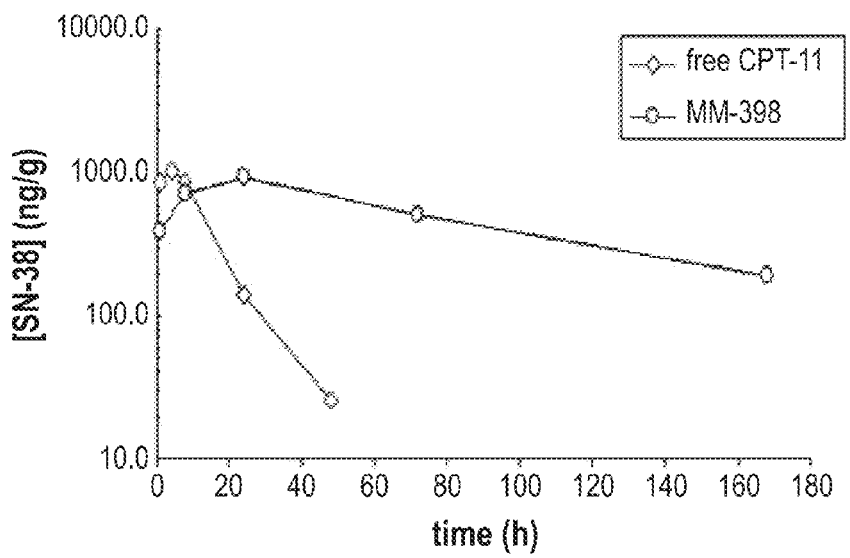
FIG. 2 is a graph showing accumulation of SN-38 in tumors following treatment with free irinotecan or liposomal irinotecan (MM-398).

As shown in FIG. 2, there was a 20-fold increase in the tumor $AUC_{SN-38}$ for MM-398 as compared to free irinotecan. The long duration of exposure allows for prolonged exposure of the slow proliferating cancer cells to the active metabolite as they progress through the cell cycle. In addition, this activity was also hypothesized to result from a reduction in intra-tumoral hypoxia, and the subsequent downstream effects on angiogenesis, metastasis, and the immunosuppressive environment in tumors.

Example 3: Effect of MM-398 on Carbonic Anhydrase IX Staining in a HT29 Xenograft Model To test whether MM-398 reduces markers of hypoxia, experiments were conducted in a human colon cancer cell (HT-29) model. Specifically, HT-29 cells were injected subcutaneously into nude mice, on day 13 either PBS control or 1.25, 2.5, 5, 10 or 20 mg/kg MM-398 was injected intravenously. MM-398 was dosed once a week for 4 weeks at the indicated doses. Tumors from both groups (n=5) were extracted 24 hours after the last dose. Frozen tumor sections were used for immunohistochemical staining of Carbonic Anhydrase IX (CAIX). Quantification of CAIX staining was performed using Definiens® (Definiens AG, Munich) software.

As shown in FIG. 3, MM-398 reduced markers of hypoxia. Specifically, the graphs in FIG. 3 show the percentage of cells that stained with medium (middle third) or high (top third) intensity for CAIX. Representative samples from each group are shown as well as the group average (mean+/−stdev). MM-398 treatment modifies the tumor microenvironment by decreasing the percentage of both medium and high CAIX positive cells in a dose-dependent manner. As hypoxia is a hallmark of resistant and aggressive disease, a reduction in hypoxia is expected to make tumor cells more sensitive to chemotherapies.

Example 4: MM-398 Increases Perfusion of Hoechst Stain

Figure 4:
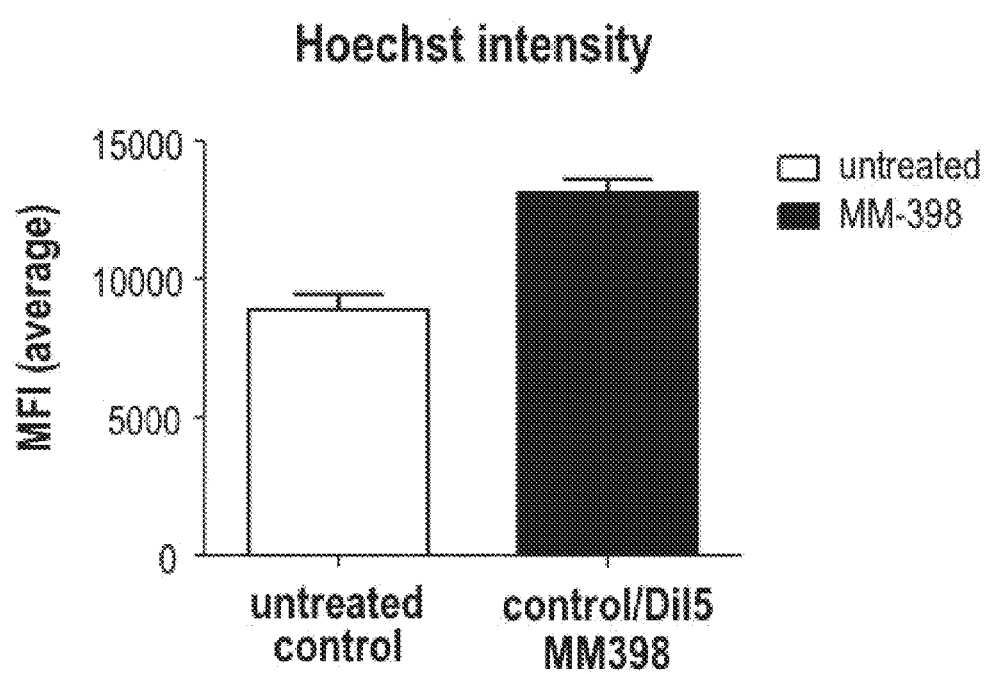
FIG. 4 shows the effect of MM-398 on perfusion of small molecule Hoechst stain.
Figure 7:
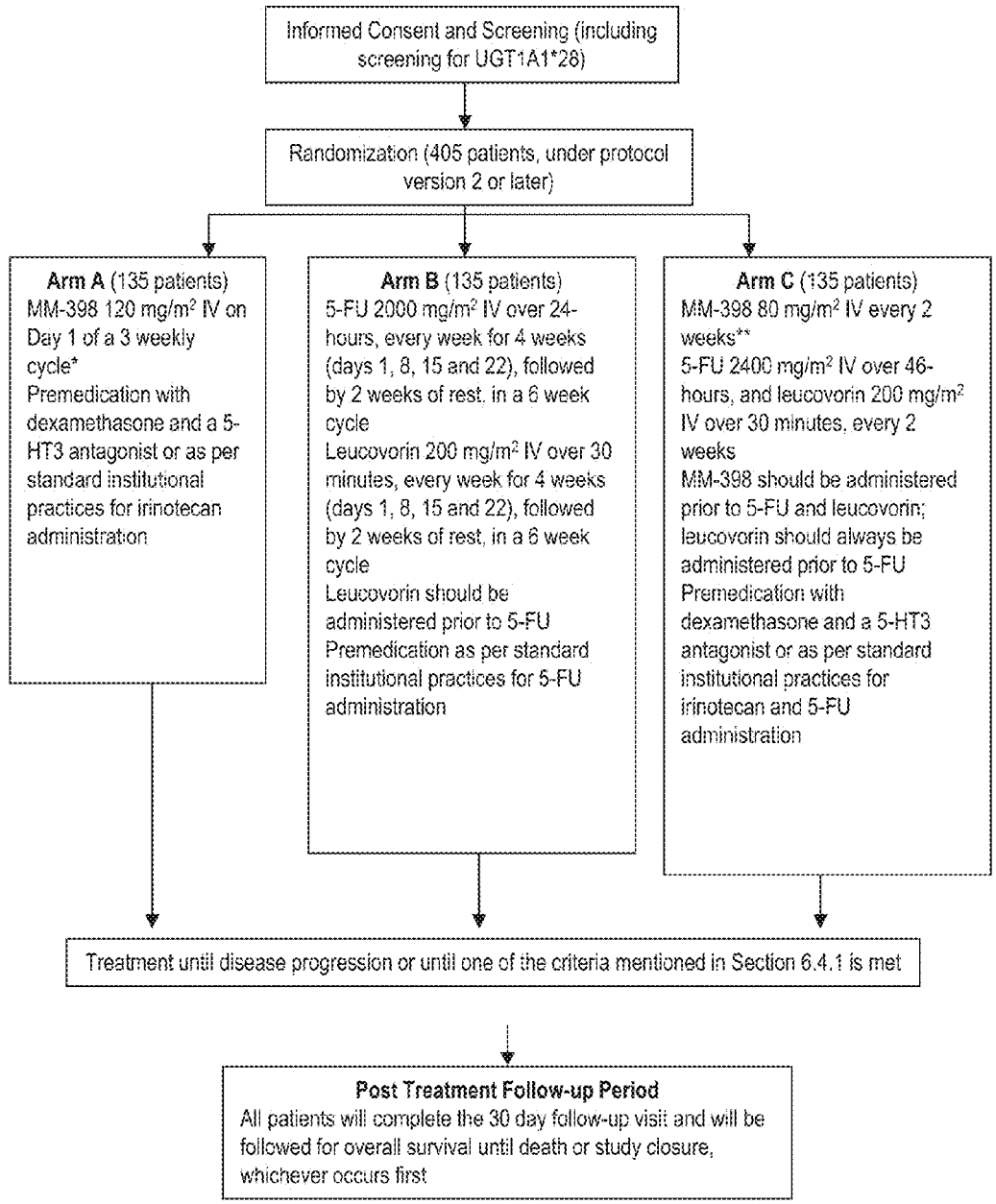
FIG. 7 is a schematic illustration of a Phase 3 study design. Patients who are homozygous for UGT1A1*28 allele and are randomized to Arm A, will receive the first cycle of therapy at a reduced dose of 80 mg/m$^2$. If the patient does not experience any drug related toxicity after the first administration of MM-398, from cycle 2 onwards, the dose may be increased in increments of 20 mg/m$^2$, up to a maximum of 120 mg/m$^2$. Patients who are homozygous for UGT1A1*28 allele and are randomized to Arm C, will receive the first cycle therapy at a reduced dose of 60 mg/m$^2$. If the patient does not experience any drug related toxicity after the first administration of MM-398, from cycle 2 onwards, the dose may be increased to 80 mg/m$^2$.

In addition to changing the chemosensitivity of tumor cells through modification of the tumor microenvironment, lowering hypoxia can indicate improved tumor vascularization, which can facilitate delivery of small molecule therapies. MM-398 treatment led to increased microvessel density 6 days after treatment as measured by CD31 (platelet endothelial cell adhesion molecule) staining in an HT29 xenograft study. To further assess the effect of MM-398 on small molecule tumor vascularization, a Hoechst 33342 perfusion experiment was conducted. Specifically, a primary pancreatic tumor was grown in NOD-SCID mice and given one dose of MM-398 (20 mg/kg). After 24 hours, Hoechst 33342 stain was administered 20 minutes prior to sacrificing the animal. As shown in FIG. 4, the increase in stain intensity in treated mice was statistically significant, p<0.001. These data indicate that MM-398 modifies the tumor microenvironment in a manner that should make tumors more susceptible to agents such as 5-FU/LV, through decreasing tumor hypoxia and increasing small molecule perfusion.

Example 5A: MM-398 (q3w) Pharmacokinetics in Humans (Phase I)

The pharmacokinetic profile of MM-398 single agent was investigated in a phase I clinical study (PEP0201) in patients at 60, 120 or 180 mg/m$^2$ dose levels and in a phase II clinical trial in gastric cancer patients (PEP0206) at 120 mg/m$^2$. Plasma levels of total irinotecan, SN-38 and encapsulated irinotecan were measured in these studies.

The peak serum concentrations of total irinotecan ($C_{max}$) ranged from 48-79 µg/ml for 120 mg/m$^2$ of MM-398, which was approximately 50 fold higher than 125 mg/m$^2$ free irinotecan. The total irinotecan half-life ($t_{1/2}$) for MM-398 ranged from 21 to 48 hours, which was approximately 2-3 fold higher than 125 mg/m$^2$ of free irinotecan. Overall, total irinotecan exposure at one week (AUC 0-T) ranged from 1200-3000 (µg*h/ml) at a dose of 120 mg/m$^2$ of MM-398, approximately 50-100 fold higher than 300 mg/m$^2$ of free irinotecan. In contrast, SN38 $C_{max}$ levels at 120 mg/m$^2$ of MM-398 ranged from 9 to 17 ng/ml, which was approximately 50% less than free irinotecan at 125 mg/m$^2$. Overall, exposure of SN38 at one week (AUC 0-T) ranged from 474 to 997 ng*/ml and was only 1-2 fold higher than achieved by free irinotecan at 300 mg/m$^2$. For both SN38 and total irinotecan, AUC increased less than proportionally with dose of MM-398. The PK parameters of encapsulated irinotecan almost matched that of total irinotecan indicates that most of irinotecan remained encapsulated in the liposomes during circulation. The MM-398 PK parameters were not significantly changed when combined with 5-FU/LV. FIGS. 5 and 6 summarize the PK findings in previous studies of MM 398.

Example 5B: MM-398 (q2w) Pharmacokinetics in Humans (Phase III)

The plasma pharmacokinetics of total irinotecan and total SN-38 were evaluated in patients with cancer who received MM-398, as a single agent or as part of combination chemotherapy, at doses between 50 and 150 mg/m$^2$ (free base) and 353 patients with cancer using population pharmacokinetic analysis. The pharmacokinetic parameters of total irinotecan and total SN-38 following the administration of MM-398 80 mg/m$^2$ (salt) as a single agent or part of combination chemotherapy are presented in Table 3. Summary of Mean (±Standard Deviation)

TABLE 3

Total Irinotecan and Total SN-38 Pharmacokinetic Parameters in Patients with Solid Tumors.

| Dose (mg/m$^2$) (salt) | Total Irinotecan | | | | | Total SN-38 | | |
|---|---|---|---|---|---|---|---|---|
| | $C_{max}$ [µg/mL] (n = 25) | $AUC_{0-\infty}$ [h · µg/mL] (n = 23) | $t_{1/2}$ [h] (n = 23) | CL [L/h] (n = 23) | $V_d$ [L] (n = 23) | $C_{max}$ [ng/mL] (n = 25) | $AUC_{0-\infty}$ [h · ng/mL] (n = 13) | $t_{1/2}$ [h] (n = 13) |
| 80 | 37.2 (8.8) | 1364 (1048) | 25.8 (15.7) | 0.20 (0.17) | 4.1 (1.5) | 5.4 (3.4) | 620 (329) | 67.8 (44.5) |

$C_{max}$: Maximum plasma concentration
$AUC_{0-\infty}$: Area under the plasma concentration curve extrapolated to time infinity
$t_{1/2}$: Terminal elimination half-life
$V_d$: Volume of distribution The pharmacokinetic parameters of total irinotecan and total SN-38 following the administration of MM-398 80 mg/m$^2$ (salt) as a single agent or part of combination chemotherapy are presented in Table 3.

Over the dose range of 50 to 150 mg/m$^2$ (free base), the $C_{max}$ and AUC of total irinotecan increases with dose. Additionally, the $C_{max}$ of total SN-38 increases proportionally with dose; however, the AUC of total SN-38 increases less than proportionally with dose. The correlation of SN-38 $C_{max}$ with liposomal irinotecan dose had not previously been established. Higher plasma SN-38 $C_{max}$ was associated with increased likelihood of experiencing neutropenia.

The $C_{max}$ of SN-38 increases proportionally with liposomal irinotecan dose but the AUC of SN-38 increases less than proportionally with dose, enabling new methods of dosage adjustment. For example, the value of the parameter associated with adverse effects ($C_{max}$) decreases by a relatively greater extent than the value of the parameter associated with the effectiveness of treatment (AUC). Accordingly, when an adverse effect is seen, a reduction in the dosing of the liposomal irinotecan can be implemented that maximizes the difference between the reduction in $C_{max}$ and in AUC. The discovery means that in treatment regimens, a given SN-38 AUC can be achieved with a surprisingly low SN-38 $C_{max}$. Likewise, a given SN-38 $C_{max}$ can be achieved with a surprisingly high SN-38 AUC.

Direct measurement of irinotecan liposome showed that 95% of irinotecan remains liposome encapsulated, and the ratios between total and encapsulated forms did not change with time from 0 to 169.5 hours post-dose. The mean volume of distribution is summarized in Table 3.

In some embodiments, the liposomal irinotecan can be MM-398 or a product that is bioequivalent to MM-398. In some embodiments, the liposomal irinotecan can be characterized by the parameters in Table 4, including a $C_{max}$ and/or AUC value that is 80-125% of the corresponding value in Table 3. The pharmacokinetic parameters of total irinotecan for various alternative liposomal irinotecan formulations administering 70 mg/m$^2$ irinotecan free base once every two weeks is provided in Table 4.

TABLE 4

Total Irinotecan Pharmacokinetic Parameters in Alternative Liposomal Irinotecan Formulations

| | Total Irinotecan | |
|---|---|---|
| Dose (mg/m$^2$) (salt) | $C_{max}$ [µg/mL] (n = 25) | $AUC_{0-\infty}$ [h · µg/mL] (n = 23) |
| 80 | 29.8-46.5 | 1091-1705 |

$C_{max}$: Maximum plasma concentration
$AUC_{0-\infty}$: Area under the plasma concentration curve extrapolated to time infinity
$t_{1/2}$: Terminal elimination half-life Plasma protein binding is <0.44% of the total irinotecan in MM-398.

The plasma clearance of total irinotecan from MM-398 80 mg/m$^2$ (salt) (equivalent to 70 mg/m$^2$ free base dose) is 0.077 L/h/m$^2$ with a terminal half live of 26.8 h. Following administration of irinotecan HCl 125 mg/m$^2$, the plasma clearance of irinotecan is 13.3 L/h/m$^2$ with a terminal half live of 10.4 h.

Example 6: Phase 1 Dose Escalation Study

A regimen combining 5-fluorouracil, leucovorin, and MM-398 was studied in a phase 1 trial of solid tumors in 16 subjects, of whom 5 were patients with pancreatic cancer. The objective tumor response rate, duration of response, and disease control rate were efficacy endpoints of the study. Among the 15 efficacy-evaluable patients, 2 (13.3%) had confirmed PR, 9 (60.0%) had SD, and 4 (26.7%) had PD. The overall disease control rate was 73.3%. Partial response was observed in one gastric cancer patient (at 80 mg/m$^2$ dose level) and one breast cancer patient (at 100 mg/m$^2$ dose level), with the duration of response of 142 and 76 days, respectively. Among the 6 patients who received the MTD dose of 80 mg/m$^2$, there were 1 PR, 4 SD and 1 PD. The tumor response rate and disease control rate were 16.7% and 83.3%, respectively. The main DLTs were grade 3 diarrhea, leucopenia, neutropenia and febrile neutropenia. The MTD for MM-398 was 80 mg/m$^2$.

In the phase 1 dose-escalation study of MM-398 in combination with 5-FU/LV in advanced solid tumors (PEP0203), a total of 401 episodes of AE were reported from the 16 treated subjects (safety population), of which 74 (18.4%) were of CTC grade 3 or above. Among all AEs, 231 (57.6%) were considered by the investigators to be treatment-related. The most common treatment-related AEs, included nausea (81.3%), diarrhea (75.0%), vomiting (68.8%), fatigue (43.8%), mucositis (43.8%), leucopenia (37.5%), neutropenia (37.5%), weight loss (37.5%), anemia (31.3%), and alopecia (31.3%). Acute cholinergic diarrhea was rarely observed. Table 5 provides the incidence of treatment-emergent adverse events by maximum CTC grade and by causality (incidence ≥20%), as seen in the PEP0203 study. Table 6 provides the incidence of grade 3 or higher treatment-emergent adverse events seen in the 5 pancreatic cancer patients treated in the PEP0203 study.

TABLE 5

Incidence of treatment-emergent adverse events by maximum CTC grade and by causality (incidence ≥20%) in the PEP0203 Study

| System organ class Preferred Term | Total (N = 16) | Severity (Grade)[1] | | | | Causality[2] | |
|---|---|---|---|---|---|---|---|
| | | I | II | III | IV | Yes | No |
| Blood and lymphatic system disorders | | | | | | | |
| Anemia | 7 (43.8%) | 3 | 2 | 2 | 0 | 5 | 2 |
| Leucopenia | 6 (37.5%) | 0 | 3 | 2 | 1 | 6 | 0 |
| Neutropenia | 6 (37.5%) | 0 | 2 | 3 | 1 | 6 | 0 |
| Gastrointestinal disorders | | | | | | | |
| Abdominal pain | 7 (43.8%) | 3 | 2 | 2 | 0 | 3 | 4 |
| Constipation | 6 (37.5%) | 3 | 3 | 0 | 0 | 0 | 6 |
| Diarrhea | 12 (75.0%) | 3 | 4 | 5 | 0 | 12 | 0 |
| Nausea | 13 (81.3%) | 6 | 6 | 1 | 0 | 13 | 0 |
| Vomiting | 12 (75.0%) | 3 | 8 | 1 | 0 | 11 | 1 |
| General disorders and administration site conditions | | | | | | | |
| Fatigue | 8 (50.0%) | 4 | 3 | 1 | 0 | 7 | 1 |
| Mucosal inflammation | 7 (43.8%) | 4 | 3 | 0 | 0 | 7 | 0 |
| Pyrexia | 7 (43.8%) | 3 | 4 | 0 | 0 | 2 | 5 |
| Infections and infestations | | | | | | | |
| Infection | 6 (37.5%) | 0 | 3 | 3 | 0 | 2 | 4 |
| Investigations | | | | | | | |
| ALT increased | 5 (31.3%) | 3 | 2 | 0 | 0 | 4 | 1 |
| AST increased | 4 (25.0%) | 3 | 1 | 0 | 0 | 1 | 3 |
| Weight decreased | 8 (50.0%) | 4 | 4 | 0 | 0 | 6 | 2 |
| Metabolism and nutrition disorders | | | | | | | |
| Anorexia | 4 (25.0%) | 1 | 2 | 1 | 0 | 3 | 1 |
| Hypoalbuminaemia | 4 (25.0%) | 0 | 3 | 1 | 0 | 0 | 4 |
| Hypocalcaemia | 5 (31.3%) | 1 | 4 | 0 | 0 | 0 | 5 |
| Hypokalaemia | 8 (50.0%) | 2 | 0 | 5 | 1 | 2 | 6 |
| Hyponatraemia | 4 (25.0%) | 2 | 0 | 0 | 2 | 0 | 4 |
| Nervous system disorders | | | | | | | |
| Dizziness | 4 (25.0%) | 4 | 0 | 0 | 0 | 1 | 3 |
| Psychiatric disorders | | | | | | | |
| Insomnia | 4 (25.0%) | 4 | 0 | 0 | 0 | 1 | 3 |
| Respiratory, thoracic and mediastinal disorders | | | | | | | |
| Cough | 5 (31.3%) | 3 | 1 | 1 | 0 | 0 | 5 |
| Skin and subcutaneous tissue disorders | | | | | | | |
| Alopecia | 5 (31.3%) | 5 | 0 | 0 | 0 | 5 | 0 |

[1]Severity grading used the highest grading ever rated for each subject if the subject had such adverse event reported
[2]Defined as subject ever experienced AE related to the study drug in causality or not

TABLE 6

Incidence of Grade 3 or higher treatment-emergent adverse events in pancreatic cancer patients in the PEP0203 Study

| Primary system organ class Preferred term | Overall N = 5 n (%) | 60 mg/m2 N = 1 n (%) | 80 mg/m2 N = 3 n (%) | 120 mg/m2 N = 1 n (%) |
|---|---|---|---|---|
| Any primary system organ class | | | | |
| Total | 3 (60.0) | 0 | 2 (66.7) | 1 (100.0) |
| Infections and infestations | | | | |
| Total | 3 (60.0) | 0 | 2 (66.7) | 1 (100.0) |
| Hepatitis viral | 1 (20.0) | 0 | 1 (33.3) | 0 |
| Infection | 1 (20.0) | 0 | 0 | 1 (100.0) |
| Pneumonia | 1 (20.0) | 0 | 1 (33.3) | 0 |
| Septic shock | 1 (20.0) | 0 | 1 (33.3) | 0 |
| Blood and lymphatic system disorders | | | | |
| Total | 2 (40.0) | 0 | 1 (33.3) | 1 (100.0) |
| Lymphopenia | 1 (20.0) | 0 | 0 | 1 (100.0) |
| Neutropenia | 1 (20.0) | 0 | 1 (33.3) | 0 |
| White blood cell disorder | 1 (20.0) | 0 | 0 | 1 (100.0) |
| Gastrointestinal disorders | | | | |
| Total | 2 (40.0) | 0 | 1 (33.3) | 1 (100.0) |
| Diarrhoea | 2 (40.0) | 0 | 1 (33.3) | 1 (100.0) |
| Abdominal pain | 1 (20.0) | 0 | 0 | 1 (100.0) |
| Gastrointestinal haemorrhage | 1 (20.0) | 0 | 1 (33.3) | 0 |
| Investigations | | | | |
| Total | 2 (40.0) | 0 | 1 (33.3) | 1 (100.0) |
| Blood bilirubin increased | 1 (20.0) | 0 | 1 (33.3) | 0 |
| Lipase increased | 1 (20.0) | 0 | 0 | 1 (100.0) |
| Neutrophil count decreased | 1 (20.0) | 0 | 0 | 1 (100.0) |
| White blood cell count decreased | 1 (20.0) | 0 | 0 | 1 (100.0) |
| Metabolism and nutrition disorders | | | | |
| Total | 2 (40.0) | 0 | 1 (33.3) | 1 (100.0) |
| Hypoalbuminaemia | 1 (20.0) | 0 | 1 (33.3) | 0 |
| Hypokalaemia | 1 (20.0) | 0 | 1 (33.3) | 0 |
| Hyponatraemia | 1 (20.0) | 0 | 0 | 1 (100.0) |
| Hypophosphataemia | 1 (20.0) | 0 | 0 | 1 (100.0) |
| Respiratory, thoracic and mediastinal disorders | | | | |
| Total | 2 (40.0) | 0 | 1 (33.3) | 1 (100.0) |
| Dyspnoea | 1 (20.0) | 0 | 0 | 1 (100.0) |
| Pleural effusion | 1 (20.0) | 0 | 1 (33.3) | 0 |
| General disorders and administration site conditions | | | | |
| Total | 1 (20.0) | 0 | 0 | 1 (100.0) |
| Death | 1 (20.0) | 0 | 0 | 1 (100.0) |

Example 7: Phase 3 NAPOLI-1 Clinical Trial

The efficacy of MM-398 was evaluated in NAPOLI-1 (also "Study 1"), a three-arm, randomized, open-label trial in patients with metastatic pancreatic adenocarcinoma with documented disease progression, after gemcitabine or gemcitabine-based therapy. NAPOLI-1 was an international randomized human Phase 3 clinical trial evaluating the use of the irinotecan liposome MM-398 in patients with a diagnosis of metastatic pancreatic cancer previously treated with a gemcitabine based therapy. The NAPOLI-1 trial is summarized below.

NAPOLI-1 was an open label, randomized, stratified by albumin (<4.0 g/dL vs ≥4.0 g/dL), Karnofsky Performance Status (KPS) (70 & 80 vs ≥90), and ethnicity (Caucasian vs East Asian vs others). The primary analysis compared each treatment arm to its corresponding 5-FU/LV control for OS by unstratified log-rank test; family-wise type I error rate was controlled at the 2-sided 0.05 level using the Bonferroni-Holm method. Primary analysis planned when at least 305 death events occurred to have 85% power to detect HR=0.67 in the MM-398 arm and 98% power to detect HR=0.50 in the MM-398+5-FU/LV arm. A supportive stratified analysis, accounting for the randomization strata, was performed.

Key eligibility criteria included Karnofsky Performance Status (KPS)≥70, serum bilirubin within institution limits of normal, and albumin≥3.0 g/dL. Patients were randomized to receive MM-398 plus 5-fluorouracil/leucovorin (MM-398/5-FU/LV), MM-398, or 5-fluorouracil/leucovorin (5-FU/LV). Randomization was stratified by ethnicity (White vs. East Asian vs. other), KPS (70-80 vs. 90-100), and baseline albumin level (≥4 g/dL vs. 3.0-3.9 g/dL). Patients randomized to MM-398/5-FU/LV received MM-398 80 mg/m$^2$ (salt) as an intravenous infusion over 90 minutes, followed by leucovorin 400 mg/m$^2$ intravenously over 30 minutes, followed by 5-fluorouracil 2400 mg/m$^2$ intravenously over 46 hours, every 2 weeks.

Patients randomized to MM-398 as a single agent received MM-398 120 mg/m$^2$ (salt) as an intravenous infusion over 90 minutes every 3 weeks. Patients randomized to 5-FU/LV received leucovorin 200 mg/m$^2$ intravenously over 30 minutes, followed by 5-fluorouracil 2000 mg/m$^2$ intravenously over 24 hours, administered on Days 1, 8, 15 and 22 of a 6-week cycle. Patients homozygous for the UGT1A1*28 allele initiated MM-398 at a reduced dose (60 mg/m$^2$ (salt) MM-398, if given with 5-FU/LV or 80 mg/m$^2$ (salt) MM-398 as a single agent). When MM-398 was withheld or discontinued for adverse reactions, 5-FU was also withheld or discontinued. When the dose of MM-398 was reduced for adverse reactions, the dose of 5-FU was reduced by 25%. Treatment continued until disease progression or unacceptable toxicity. The major efficacy outcome measure was overall survival (OS) with two pair-wise comparisons: MM-398 versus 5-FU/LV and MM-398/5-FU/LV versus 5-FU/LV. Additional efficacy outcome measures were progression-free survival (PFS) and objective response rate (ORR). Tumor status assessments were conducted at baseline and every 6 weeks thereafter. The trial was initiated as a two-arm study and amended after initiation to include a third arm (MM-398/5-FU/LV). The comparisons between the MM-398/5-FU/LV and the 5-FU/LV arms are limited to patients enrolled in the 5-FU/LV arm after this protocol amendment.

Four hundred seventeen patients were randomized to: MM-398/5-FU/LV (N=117), MM-398 (N=151), or 5-FU/LV (N=149). Baseline demographics and tumor characteristics for the 236 patients randomized to MM-398/5-FU/LV or 5-FU/LV (N=119) after the addition of the third arm to the study were a median age of 63 years (range 34-81 years) and with 41%≥65 years of age; 58% were men; 63% were White, 30% were Asian, 3% were Black or African American, and 5% were other. Mean baseline albumin level was 3.97 g/dL, and baseline KPS was 90-100 in 53% of patients. Disease characteristics included liver metastasis (67%) and lung metastasis (31%). A total of 13% of patients received gemcitabine in the neoadjuvant/adjuvant setting only, 55% of patients had 1 prior line of therapy for metastatic disease, and 33% of patients had 2 or more prior lines of therapy for metastatic disease. All patients received prior gemcitabine (alone or in combination with another agent); 54% received prior gemcitabine in combination with another agent, and 13% received prior gemcitabine in combination with nab-paclitaxel.

Figure 8:
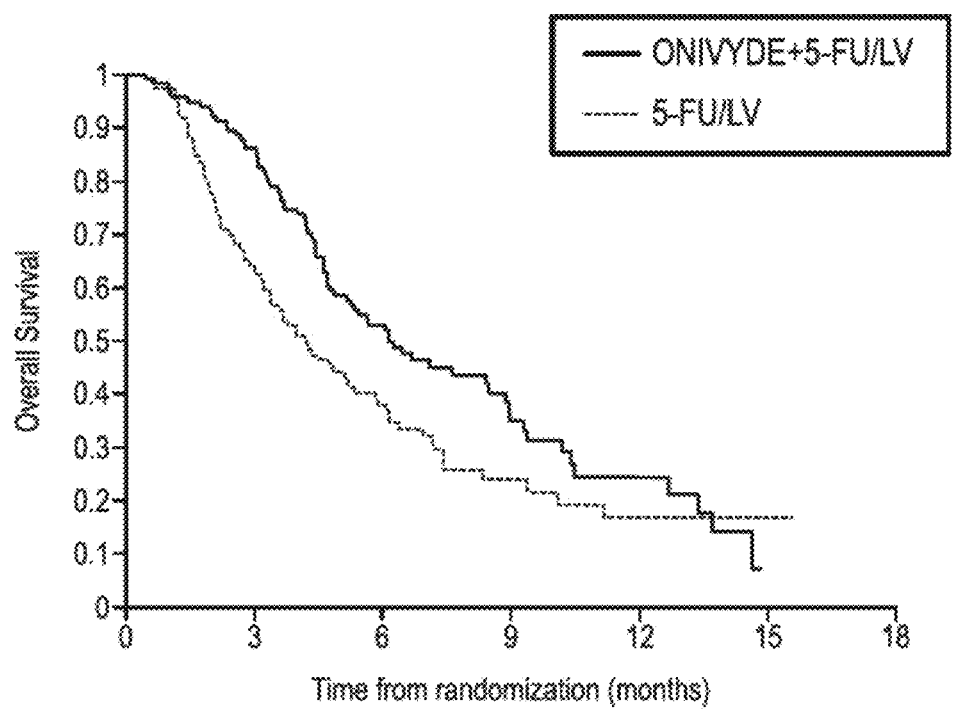
FIG. 8 is a graph providing the overall survival of patients in an assessment of the clinical efficacy and safety of the irinotecan liposome injection monotherapy or the irinotecan liposome injection in combination with 5-fluorouracil and leucovorin (the irinotecan liposome injection+5-FU/LV), compared to an active control arm of 5-FU/LV.
Figure 9:
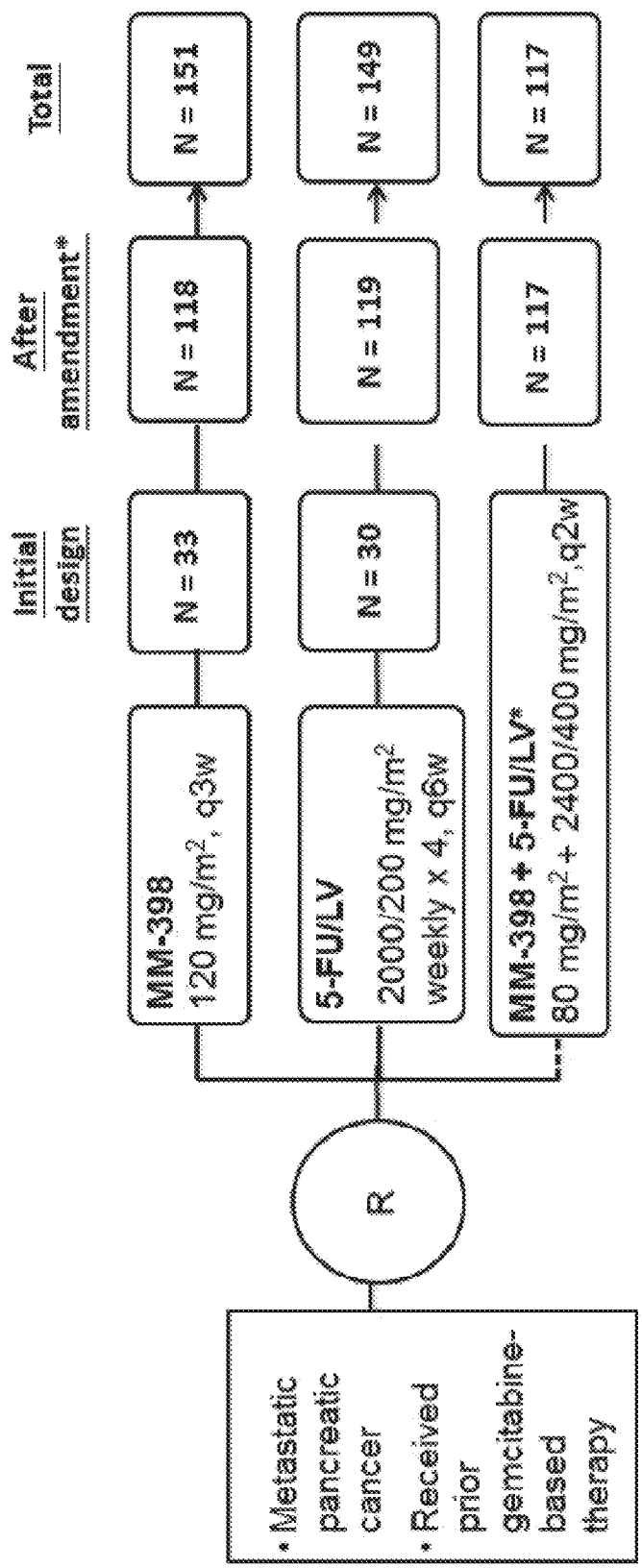
FIG. 9 is a flow-chart representation of the NAPOLI-1 study design.

NAPOLI-1 demonstrated a statistically significant improvement in overall survival for the MM-398/5-FU/LV arm over the 5-FU/LV arm as summarized in Table 7 and shown graphically in FIG. 8. There was no improvement in overall survival for the MM-398 arm over the 5-FU/LV arm (hazard ratio=1.00, p-value=0.97 (two-sided log-rank test)).

The OS and PFS benefits were maintained for MM-398+5-FU/LV compared with 5-FU/LV alone. Convergence of the OS curves at 20 months (with 19 [16%] patients surviving beyond 20 months) is likely a reason for the observed attenuation of the OS HR estimate and unstratified log-rank P value.

TABLE 7

Efficacy Results from Study 1†‡

|  | MM-398/5-FU/LV (N = 117) | 5-FU/LV (N = 119) |
|---|---|---|
| Overall Survival |  |  |
| Number of Deaths, n (%) | 77 (66) | 86 (72) |
| Median Overall Survival (months) | 6.1 | 4.2 |
| (95% CI) | (4.8, 8.5) | (3.3, 5.3) |
| Hazard Ratio (95% CI) | 0.68 (0.50, 0.93) | |
| p-value (log-rank test) | 0.014 | |
| Progression-Free Survival |  |  |
| Death or Progression, n (%) | 83 (71) | 94 (79) |
| Median Progression-Free Survival (months) | 3.1 | 1.5 |
| (95% CI) | (2.7, 4.2) | (1.4, 1.8) |
| Hazard Ratio (95% CI) | 0.55 (0.41, 0.75) | |
| p-value (log rank test) | p < 0.001 | |
| Objective Response Rate |  |  |
| Confirmed complete or partial response n (%) | 9 (7.7) | 1 (0.8) |
| (95% CI) | (2.9, 12.5) | (0, 2.5) |

†5-FU/LV = 5-fluorouracil/leucovorin; CI = confidence interval
‡The MM-398 dose in Study 1, 70 mg/m$^2$, is based on irinotecan as the free base (equivalent to 80 mg/m$^2$ of irinotecan as a hydrochloride trihydrate).

Table 7 sets out that the median overall survival of the MM-398/5-FU/LV is 6.1 months. Median overall survival is used to express survival rates. It is the amount of time after which, in the MM-398/5-FU/LV of Study 1 described herein (presented in table 7), 50% of the patients have died and 50% have survived in a study population. The expected lifetime in months from commencement of treatment with the MM-398/5-FU/LV treatment regimen as disclosed herein is defined by the parameter, $t_{surv}$. In some embodiments, the $t_{surv}$ of an individual being treated is at least ⅔ of the median overall survival rate (≥4.1 months (to one decimal place (dp))), such as at least ⅚ of the median overall survival (≥5.1 months (1 dp)) or at least the median overall survival (≥6.1 months). In some embodiments, the $t_{surv}$ of an individual being treated is less than 2 times the median overall survival rate (<12.2 months (1 dp)), such as less than 1.5 times the median overall survival (<9.15 months (2 dp)) or less than 1.2 times the median overall survival (<7.32 months (1 dp)). In some embodiments, the $t_{surv}$ of an individual being treated is at least ⅔ of the median overall survival rate and less than 2 times the median overall survival rate, such as less than 1.5 times the median overall survival or less than 1.2 times the median overall survival. In some embodiments, the $t_{surv}$ of an individual being treated is at least ⅚ of the median overall survival rate and less than 2 times the median overall survival rate, such as less than 1.5 times the median overall survival or less than 1.2 times the median overall survival. In some embodiments, the $t_{surv}$ of an individual being treated is at least the median overall survival rate and less than 2 times the median overall survival rate, such as less than 1.5 times the median overall survival or less than 1.2 times the median overall survival.

Figure 12:
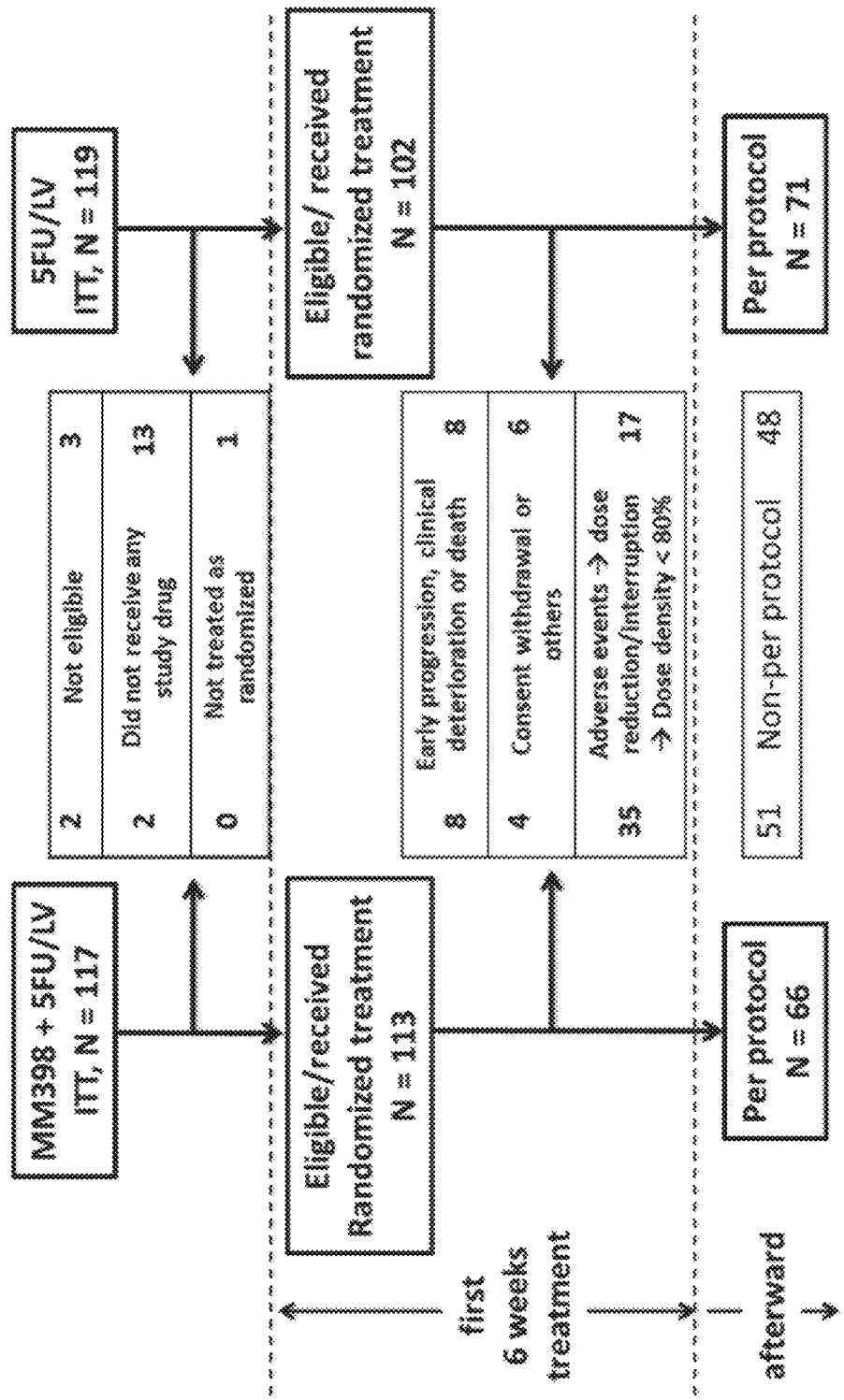
FIG. 12 is a flow chart explaining the ITT (all randomized patients) and PP (Per Protocol) populations. The Per Protocol population comprises eligible patients who received ≥80% dose density of the protocol defined treatment during the first 6 weeks of treatment.
Figure 13:
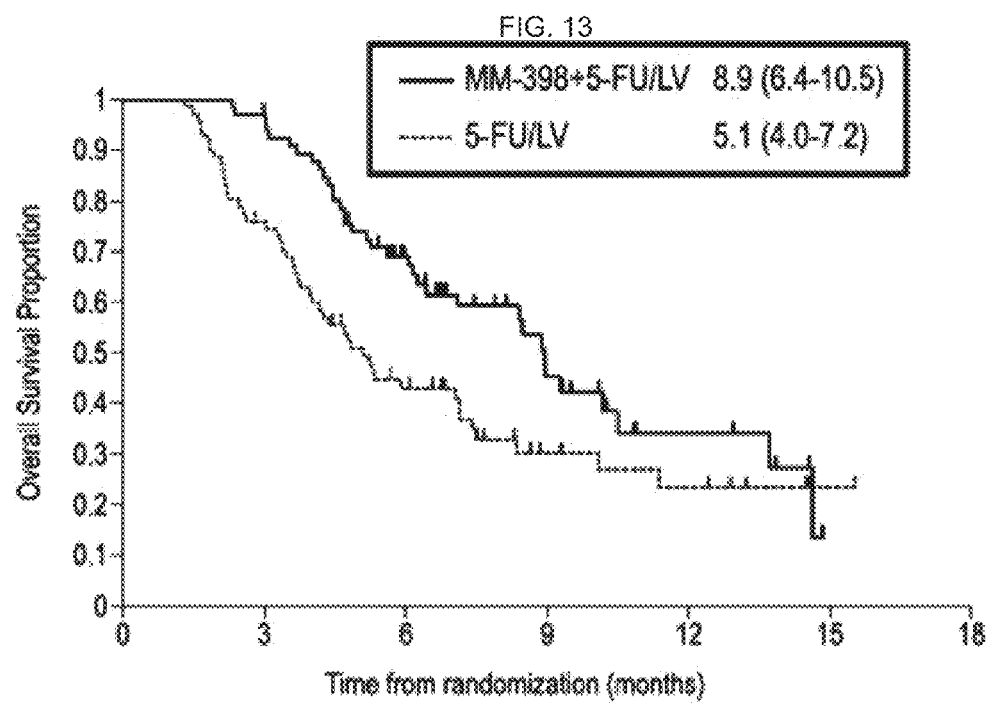
FIGS. 13 and 14 are graphical representations of overall survival (OS) for the Per Protocol (PP) patient population vs. the Non-Per Protocol (Non-PP) patient population. The results presented in the figures are a data cut from a protocol-defined primary analysis. Per protocol population was defined as patients who received at least 80% of the protocol defined treatment during the first 6 weeks of treatment and did not have protocol deviations related to inclusion/exclusion criteria, receiving prohibited therapies or not receiving treatment as randomized.
Figure 14:
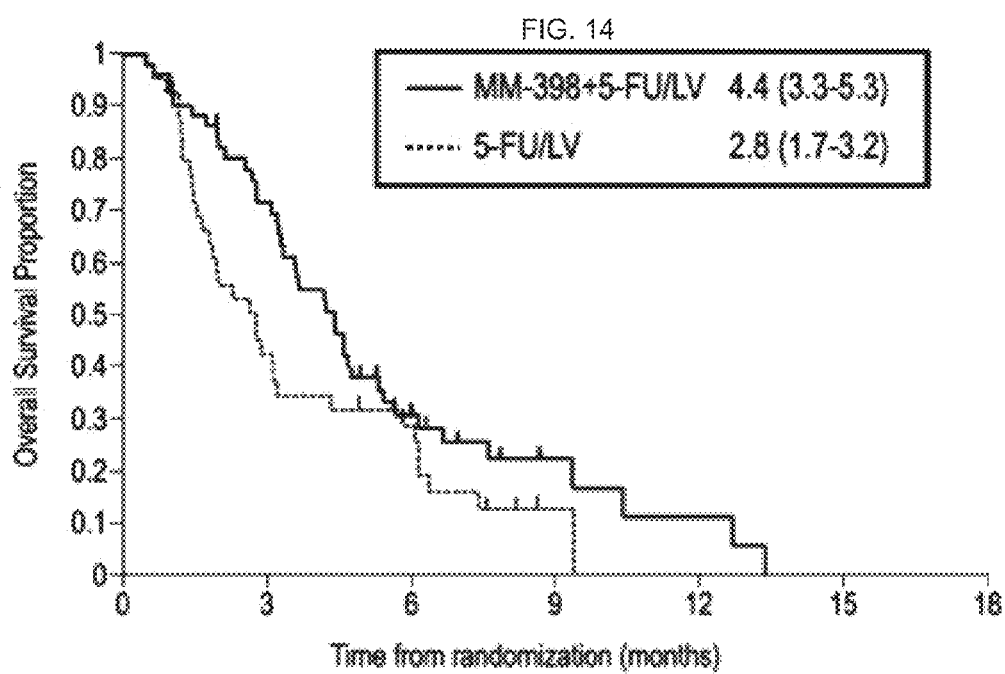

In NAPOLI-1, analysis of the ITT (intent to treat) patient group demonstrated statistically significant increase in overall survival (OS) of MM-398+5-FU/LV (MM-398 80 mg/m$^2$ (salt) q2w regimen) over 5-FU/LV alone (FIGS. 11A and 11B) of 6.1 months versus 4.2 months respectively. In comparison, MM-398, as a single agent (120 mg/m$^2$ q3w regimen), did not show a significant difference in OS. In the Per Protocol (PP) population (described in FIG. 12) of patients in the NAPOLI-1 human clinical trial (patients receiving 6 weeks of treatment), the MM-398+5-FU/LV combination regimen achieved a median OS of 8.9 months versus 5.1 months in the 5-FU/LV arm (stratified Hazard Ratio (HR): 0.47, p=0.0018; FIGS. 13 and 14). The observed patient safety profile was manageable, with most frequent being grade≥3 adverse events including neutropenia, fatigue and GI effects, such as diarrhea and vomiting (FIG. 17).

The primary endpoint of the NAPOLI-1 study was overall survival; and the key secondary endpoints were Progression Free Survival (PFS), Objective Response Rate (ORR), Tumor Marker Response (CA19-9) and Safety. The study was amended to add the MM-398+5-FU/LV arm once safety data on the combination became available. Only those patients enrolled in the 5FU/LV arm after the amendment (N=119), were used as the control for the combination arm.

Key Inclusion Criteria for the NAPOLI-1 trial were: Adenocarcinoma of the exocrine pancreas; Metastatic disease, measurable or non-measurable; Progressed after prior gemcitabine or gemcitabine-containing therapy; KPS≥70; Adequate bone marrow, hepatic (bilirubin within normal range for the institution and albumin≥3 g/dL), and renal function.

Sixty six PP patients were in the MM398+5-FU/LV arm and 71 PP patients were in the 5-FU/LV arm of NAPOLI-1. The NAPOLI-1 study was well balanced. Patients in the MM-398+5FU/LV and 5FU/LV arms were consistent across the following patient characteristics: prognostic factors, demographics (age, sex, race), tumor and pre and post treatment characteristics. Post-study anticancer therapy was 31% in the MM-398+5-FU/LV arm and 38% in the 5-FU/LV arm.

Efficacy Analysis of NAPOLI-1 Clinical Trial (Phase III)

Figure 11A:
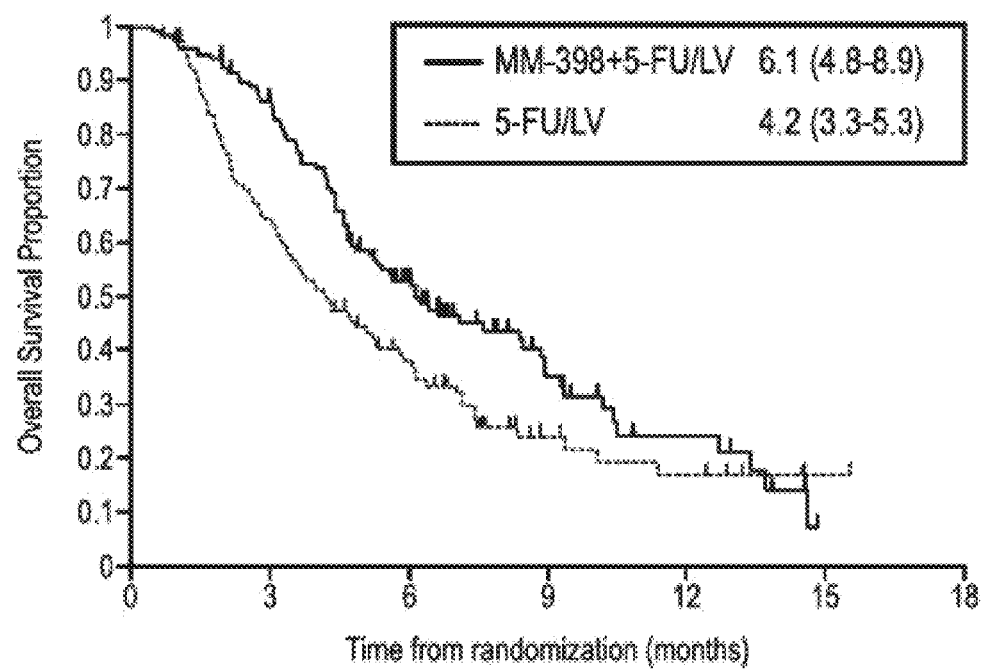
FIGS. 11A and 11B are graphical representations of overall survival (ITT population) in MM-398+5-FU/LV vs. MM-398 or 5-FU/LV alone. The data presented is the protocol-defined primary analysis data cut after 305 events. "" denotes un-stratified HR: 0.67 (0.49-0.92), p=0.0122; "*" denotes un-stratified HR: 0.99 (0.77-1.28), p=0.9416.
Figure 11B:
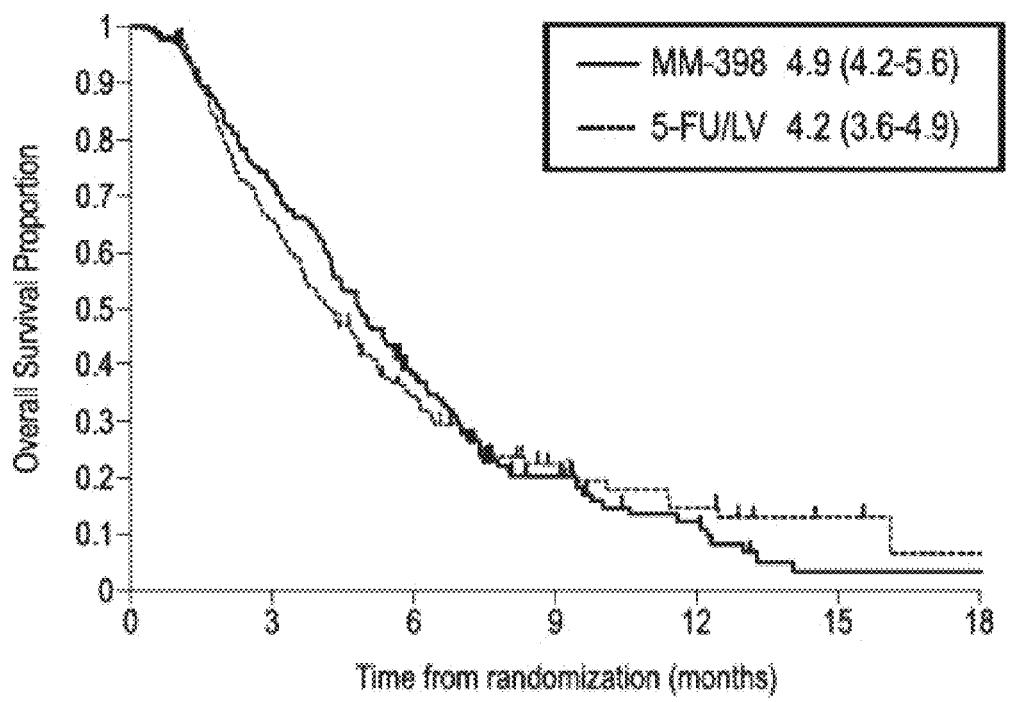

Overall Survival Results from the ITT patient group in the NAPOLI-1 clinical trial are shown in FIGS. 11A and 11B. FIG. 11A shows the median overall survival rate for the MM-398+5-FU/LV arm was 6.1 months (95% CI 4.8-8.9) and the 5-Fu/LV arm overall survival rate was 4.2 months (95% CI 3.3-5.3) and the stratified HR was 0.57 (95 CI 0.41-0.8), p=0.0009. FIG. 11B shows the median overall survival rate for the MM-398 arm was 4.9 months (95% CI 4.2-5.6) and the 5-FU/LV arm median OS was 4.2 months (95% CI 3.6-4.9) and the stratified HR was 0.93 (95 CI 0.71-1.21), p=035545.

The Per Protocol population comprises eligible patients who received ≥80% dose density of the protocol defined treatment during the first 6 weeks of treatment and did not have the following protocol violations: receipt of any prohibited therapies as defined in the protocol, not receiving treatment as randomized, or inclusion/exclusion criteria deviations.

Overall Survival Results for the PP and Non-PP populations are shown in FIGS. 13 and 14 respectively. FIG. 13 shows the median overall survival rate for the PP population; the median OS for the MM-398+5-FU/LV arm was 8.9 months (95% CI 6.4-10.5) and the median OS rate for the 5-Fu/LV arm was 5.1 months (95% CI 4.0-7.2) and the stratified HR was 0.47 (95 CI 0.29-0.77), p=0.0018. FIG. 14 shows the median overall survival rate for the Non-PP population; the median OS for the MM-398+5-FU/LV arm was 4.4 months (95% CI 3.3-5.3) and the median OS rate for the 5-Fu/LV arm was 2.8 months (95% CI 1.7-3.2) and the stratified HR was 0.56 (95 CI 0.33-0.97), p=0.365.

After 378 OS events, MM-398+5-FU/LV (n=117) retained an OS advantage relative to 5-FU/LV (n=119): 6.2 mo (95% confidence interval [CI], 4.8-8.4) vs 4.2 mo (95% CI, 3.3-5.3) with an unstratified HR of 0.75 (P=0.0417). In contrast, there was no OS advantage with MM-398 monotherapy (n=151) vs 5-FU/LV (n=149): 4.9 mo [95% CI, 4.2-5.6] vs 4.2 mo [95% CI, 3.6-4.9], HR=1.08; P=0.5. Six-month survival estimates were 53% (95% CI, 44-62%) for MM-398+5-FU/LV vs 38% (95% CI, 29-47%) for 5-FU/LV; 12-month survival estimates were 26% (95% CI, 18-35%) for MM-398+5-FU/LV vs 16% (95% CI, 10-24%) for 5-FU/LV. With events in nearly all patients, the OS curves converge at about 20 months with 19 patients (16.2%) surviving beyond 20 months. This is a reason for attenuation of the HR estimate and unstratified log rank p-value. The most common grade 3+ adverse events occurring at a ≥2% incidence in the MM-398-containing arms were neutropenia, diarrhea, vomiting, and fatigue.

The median OS benefit for MM-398+5FU/LV over 5-FU/LV was maintained, with a similar safety profile. MM-398+5-FU/LV may be a new standard of care for patients with mPAC previously treated with gemcitabine-based therapy. The median overall survival (OS) increased significantly with MM-398+5-FU/LV relative to 5-FU/LV (6.1 vs 4.2 months; unstratified hazard ratio [HR]=0.67 [95% confidence interval (CI), 0.49-0.92]; P=0.012). The median OS did not differ between patients assigned MM-398 monotherapy and those allocated to 5-FU/LV (4.9 vs 4.2 months; unstratified HR=0.99 [95% CI, 0.77-1.28]; P=0.94). The median progression-free survival (PFS; 3.1 vs 1.5 months; unstratified HR=0.56 [95% CI, 0.41-0.75]; P=0.0001) and objective response rate (ORR; 16% vs 1%; P<0.0001) were also improved with MM-398+5-FU/LV compared with 5-FU/LV alone.

The objectives of the current descriptive analysis of the NAPOLI-1 trial are to evaluate the robustness of the previously observed OS treatment effect for MM-398+5-FU/LV versus 5-FU/LV control using data from longer follow-up, and to assess the long-term safety and tolerability of MM-398. A total of 76 sites in 14 countries enrolled 417 patients between January 2012 and September 2013. Patient demographics and baseline clinical characteristics were well balanced across treatment arms (Table 8).

Treatment Exposure

The mean duration of treatment exposure was 18.5 weeks (median, 8.7 weeks; range, 2-115 weeks) in the MM-398+5-FU/LV arm, 12.3 weeks (median, 8.9 weeks; range, 3-69 weeks) in the MM-398 arm, and 10.8 weeks (median, 6.0 weeks; range, 1-68 weeks) in the 5-FU/LV control arm. The mean relative dose intensity of MM-398 was 83% in the combination arm and 90% in the monotherapy arm.

TABLE 8

Patient Demographic and Baseline Clinical Characteristics

| Parameter | naI-IRI + 5-FU/LV (n = 117) | 5-FU/LV combination control (n = 119) | naI-IRI monotherapy (n = 151) | 5-FU/LV monotherapy control (n = 149) |
|---|---|---|---|---|
| Median age (IQR), y | 63 (57-70) | 62 (55-69) | 65 (58-70) | 63 (55-69) |
| KPS, % | | | | |
| 100 | 15 | 14 | 15 | 15 |
| 90 | 44 | 34 | 42 | 36 |
| 80 | 32 | 43 | 33 | 41 |
| 70 | 6 | 8 | 10 | 7 |
| 50-60 | 3 | 0 | 0 | 0 |
| Race, % | | | | |
| Caucasian | 62 | 64 | 59 | 62 |
| East Asian | 29 | 30 | 34 | 34 |
| Other | 9 | 6 | 7 | 5 |
| CA19-9 ≥40 U/mL, %[a] | 81 | 80 | 86 | 81 |
| Pancreatic head tumor, % | 65 | 58 | 66 | 54 |
| Prior lines of metatstatic therapy, % | | | | |
| 0[b] | 13 | 13 | 11 | 13 |
| 1 | 53 | 56 | 57 | 58 |
| 2 | 34 | 31 | 32 | 30 | naI-IRI, nanoliposomal irinotecan; 5-FU, 5-flurouracil; LV, leucovorin; IQR, interquartile range; KPS, Karnofsky performance status; CA19-9, carbohydrate antigen 19-9.
[a]Includes only patients who had a measured CA19-9 value prior to treatment. Data were missing for 3 patients in the MM-398 + 5-FU/LV group and 5 patients each in the nal-IRI monotherapy and 5-FU/LV groups.
[b]Patients received neoadjuvant, adjuvant, or locally advanced treatment, but had no previous therapy for metatstatic disease.

Figure 21B:
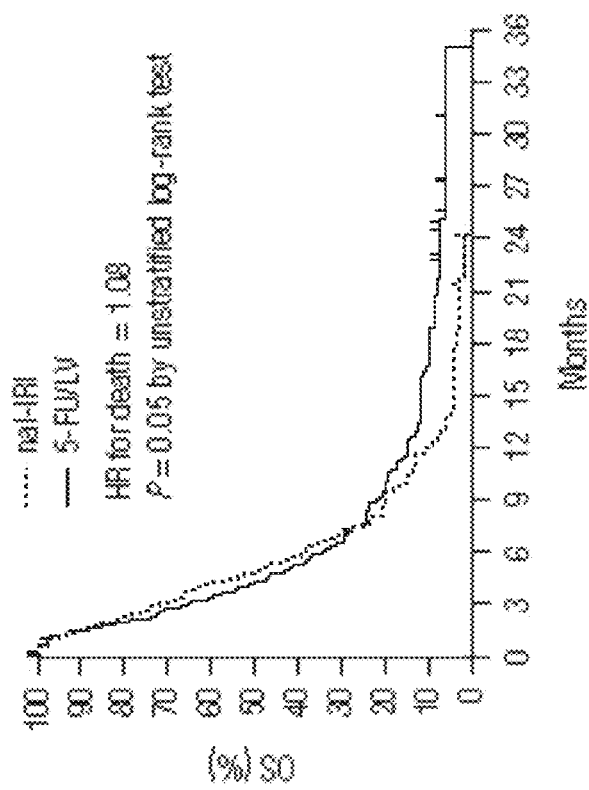
FIG. 21B is a graphical representation of the Overall Survival Rate (OS) corresponding to treatment with MM-398 vs. 5-FU/LV alone.
Figure 21A:
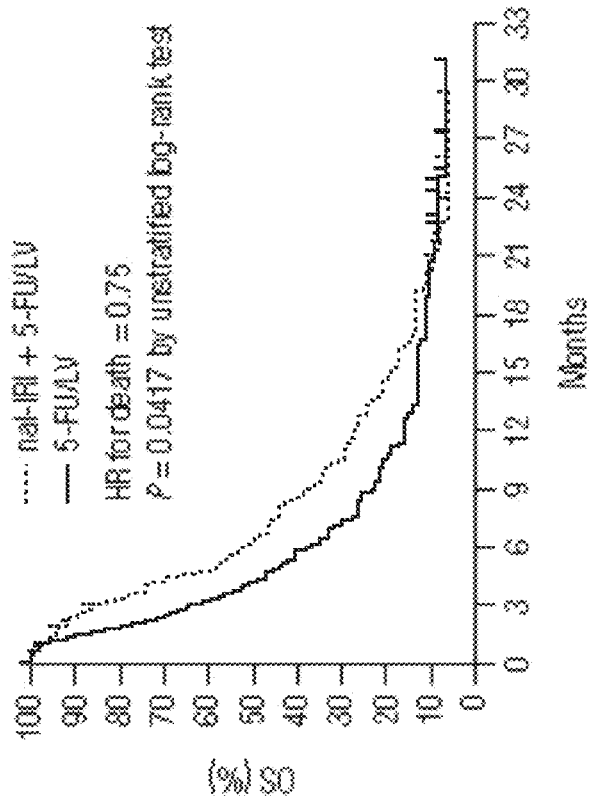
FIG. 21A is a graphical representation of the Overall Survival Rate (OS) corresponding to treatment with MM-398+5-FU/LV vs. 5-FU/LV alone.
Figure 22A:
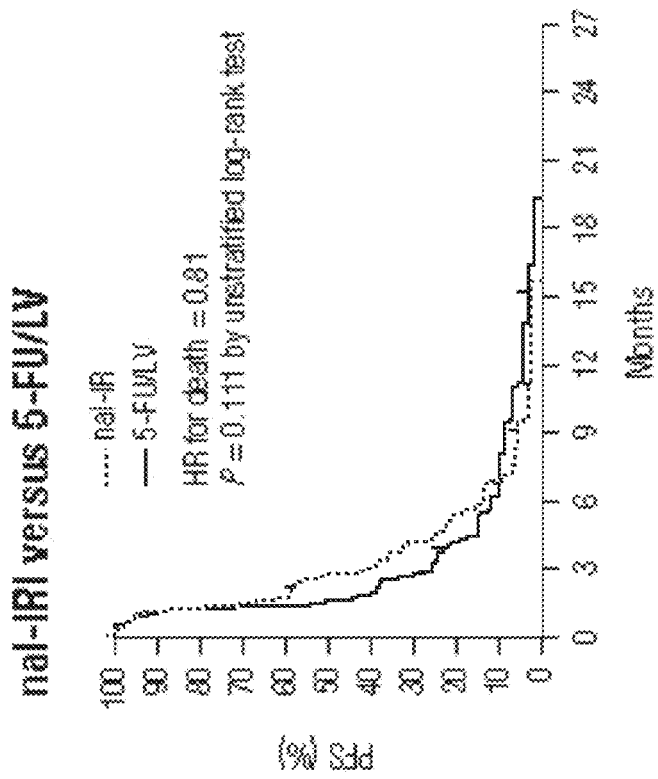
FIG. 22A is a graphical representation of the Progression Free Survival Rate (PFS) corresponding to treatment with MM-398+5-FU/LV vs. 5-FU/LV alone.
Figure 22B:
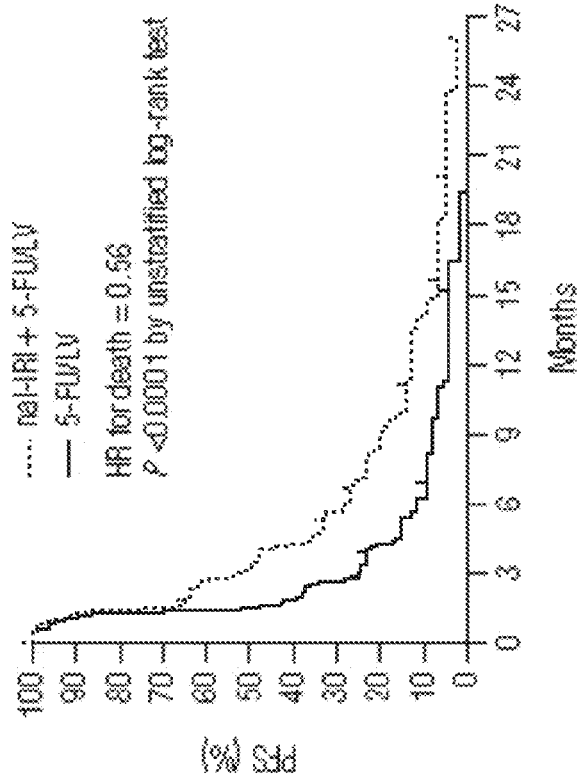
FIG. 22B is a graphical representation of the Progression Free Survival Rate (PFS) corresponding to treatment with MM-398 vs. 5-FU/LV alone.
Figure 23:
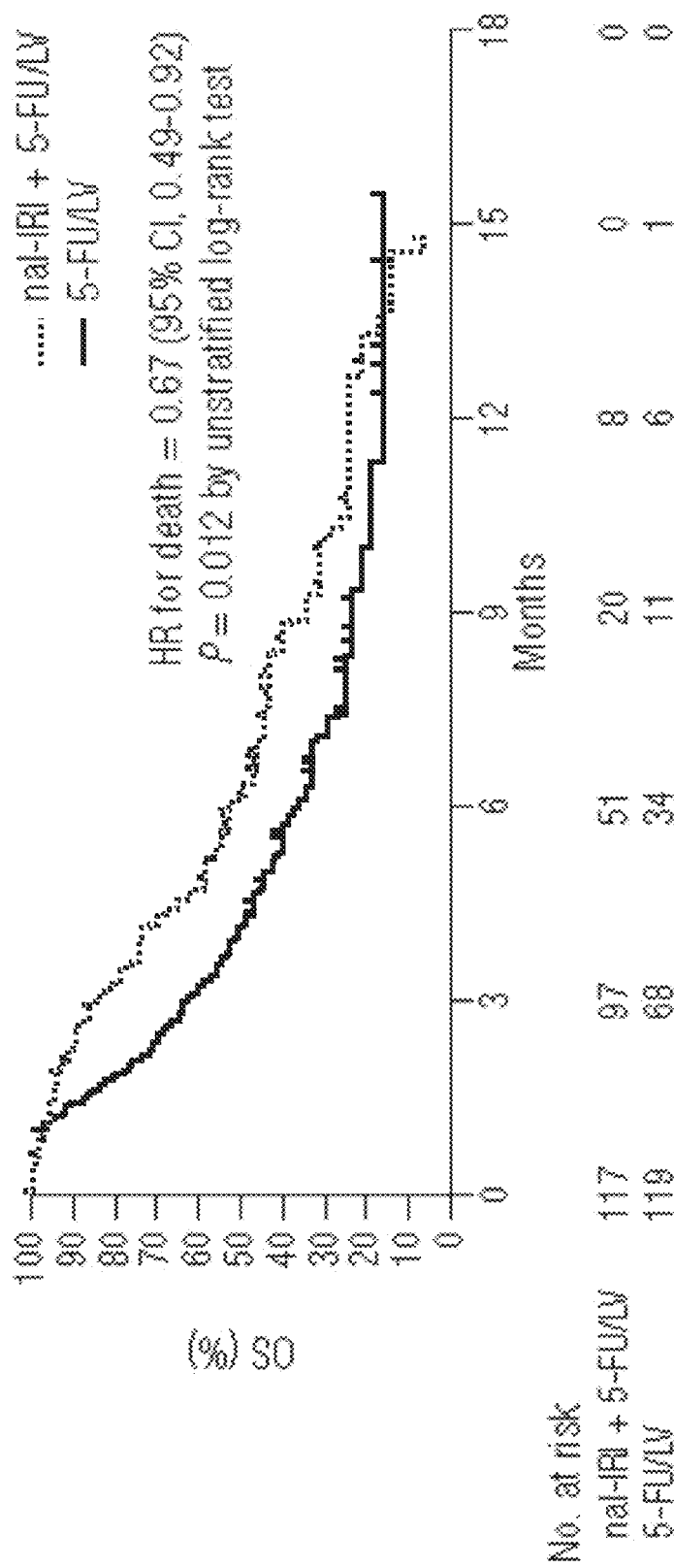
FIG. 23 is a Kaplan-Meier graph of Overall Survival (OS) in the NAPOLI-1 trial.
Figure 24:
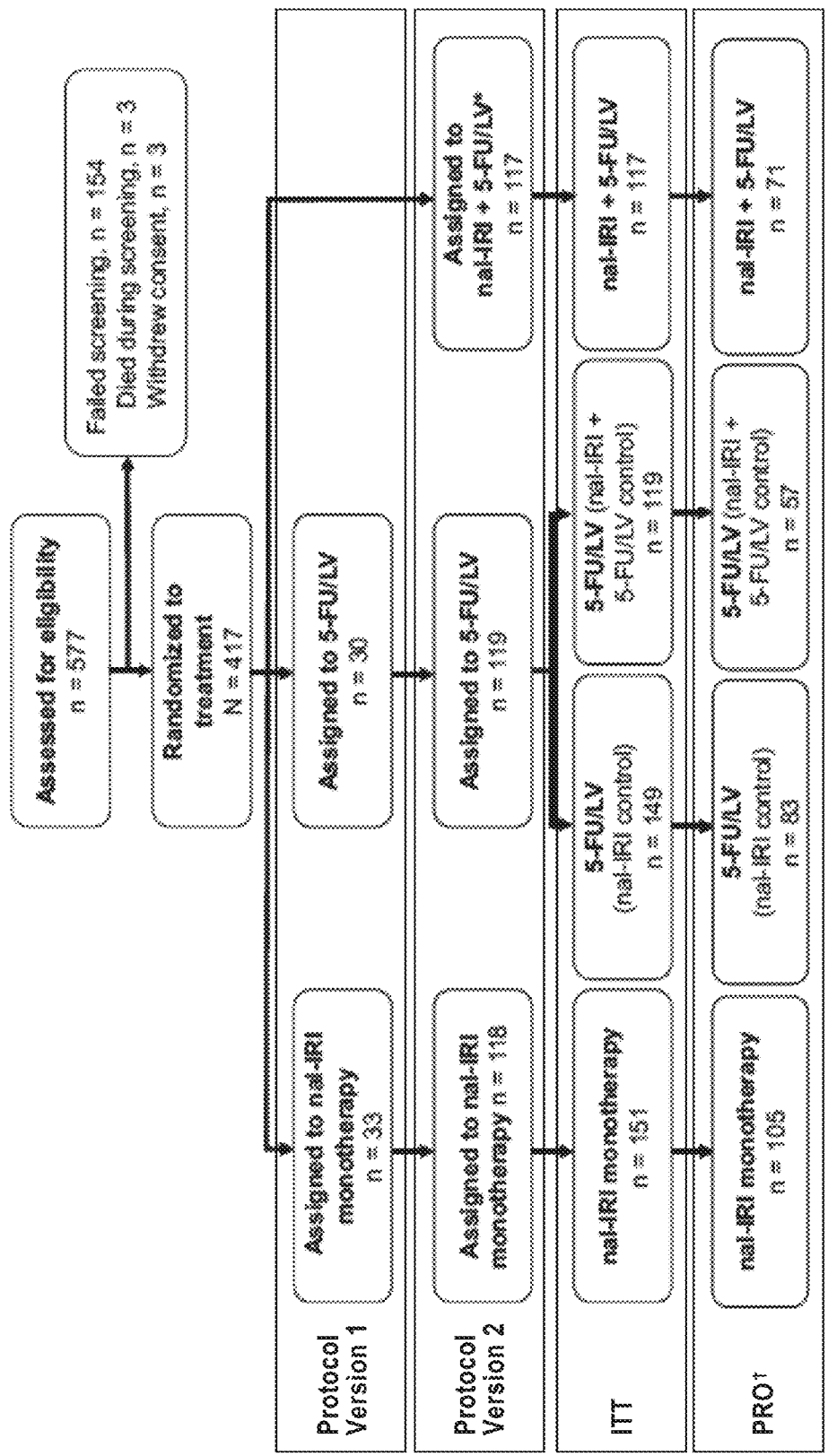
FIG. 24 is a trial profile.
Figure 26:
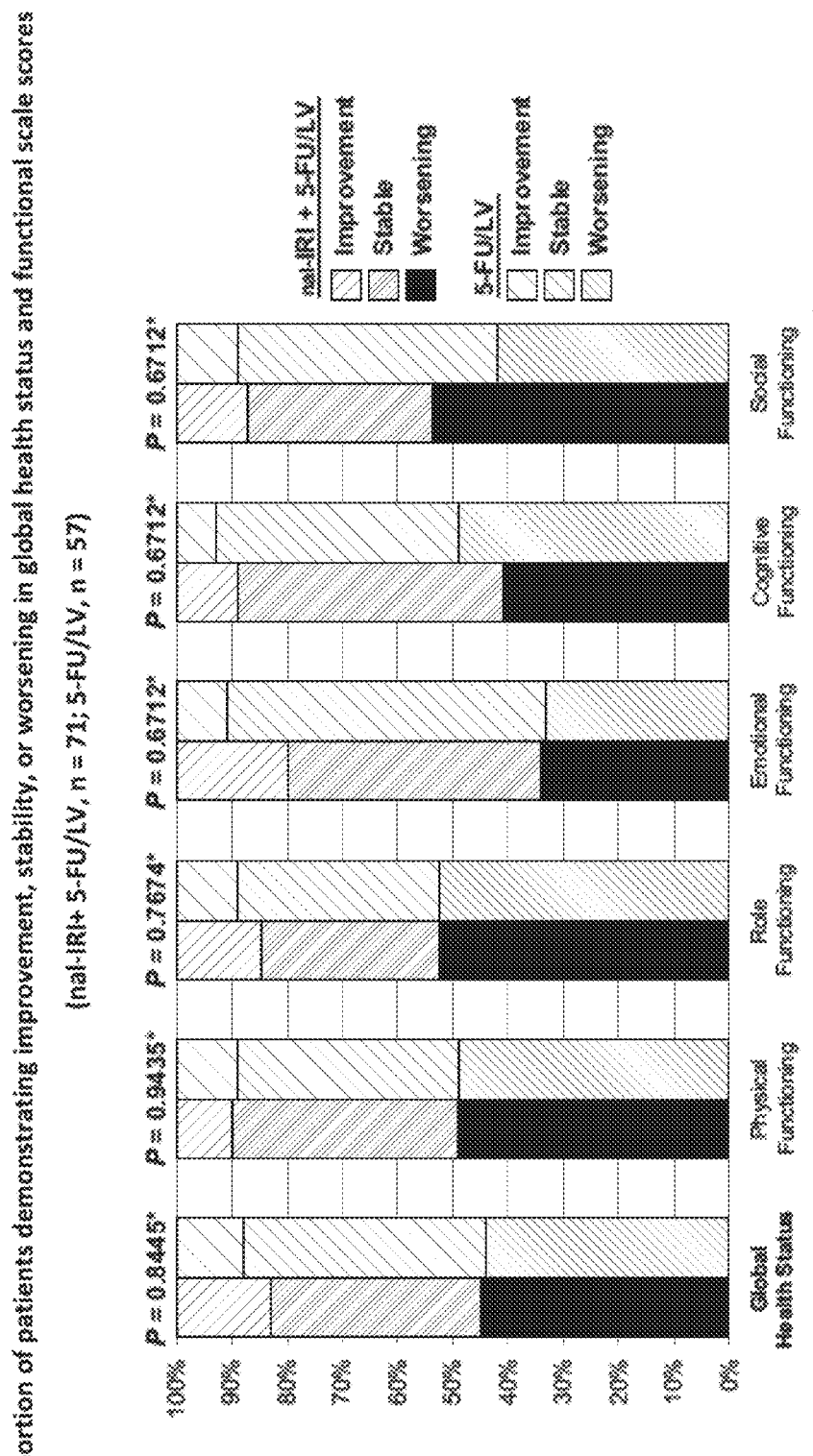
FIG. 26 is a graphical representation of the proportion of patients demonstrating improvement, stability, or worsening in global health status and functional scale scores (MM-398+5-FU/LV, n=71; 5-FU/LV, n=57).
Figure 27:
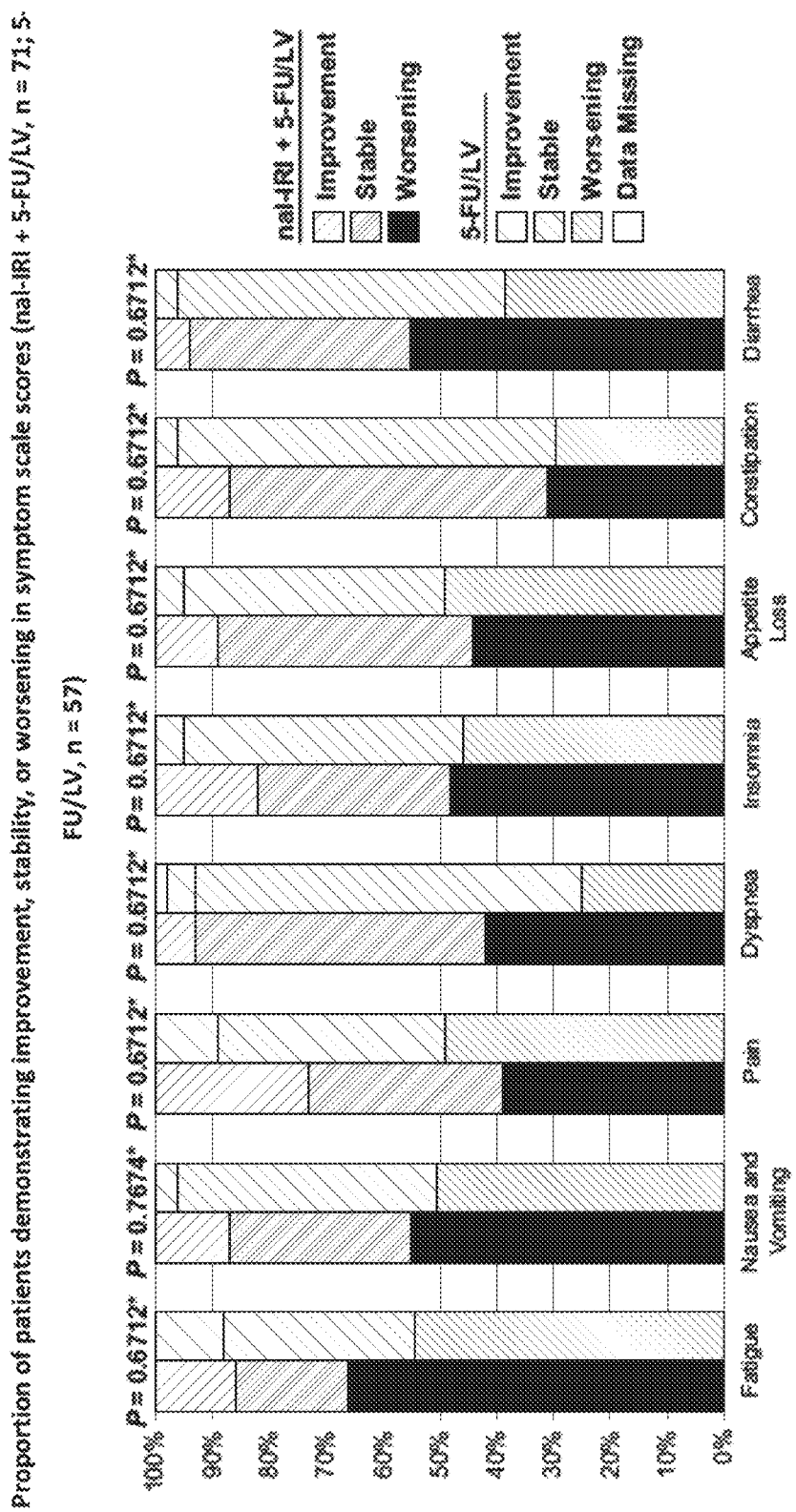
FIG. 27 is a graphical representation of the proportion of patients demonstrating improvement, stability, or worsening in symptom scale scores (MM-398+5-FU/LV, n=71; 5-FU/LV, n=57).
Figure 28:
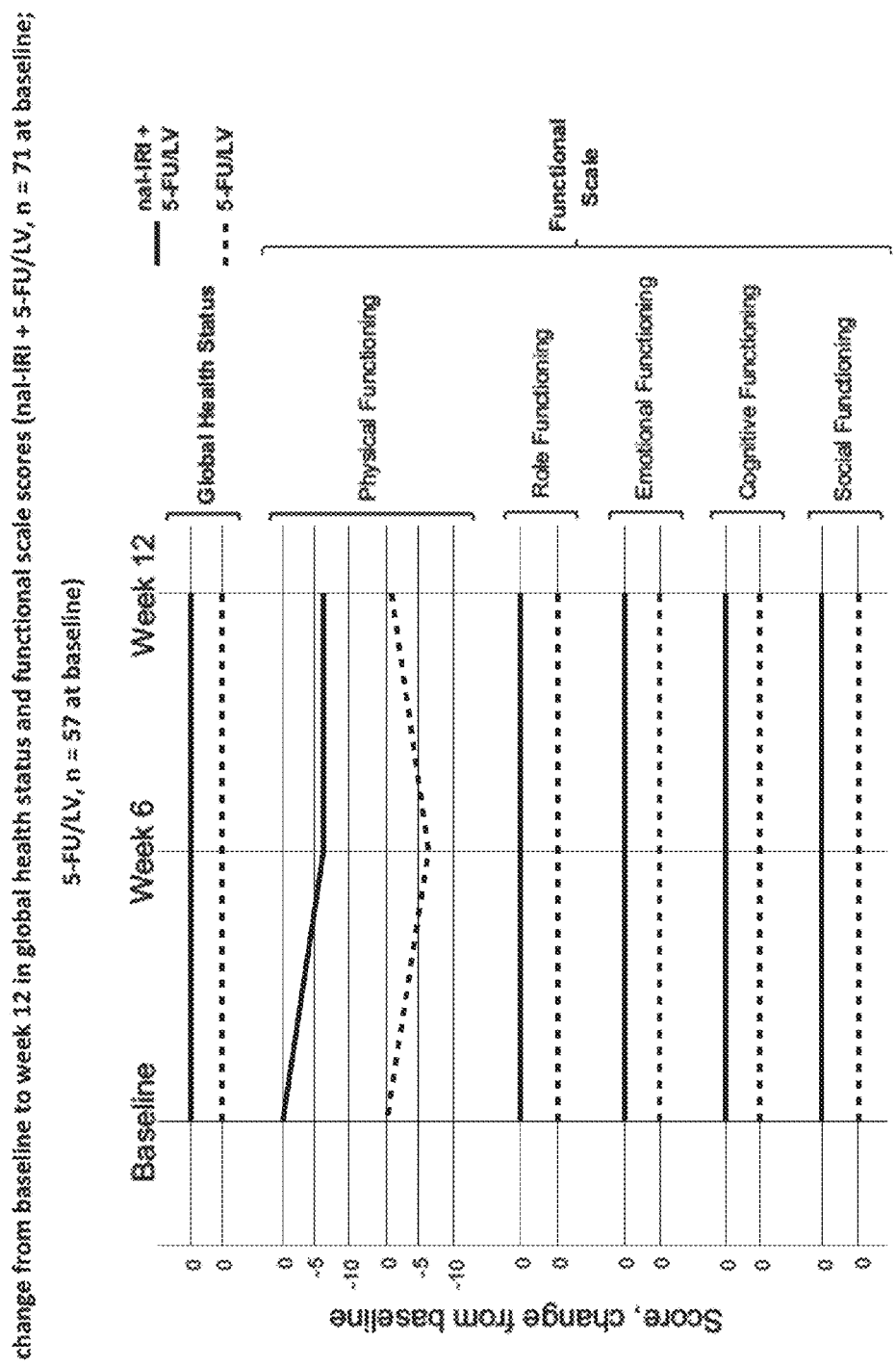
FIG. 28 is a graphical representation of the median change from baseline to week 12 in global health status and functional scale scores (MM-398+5-FU/LV, n=71 at baseline; 5-FU/LV, n=57 at baseline).
Figure 29:
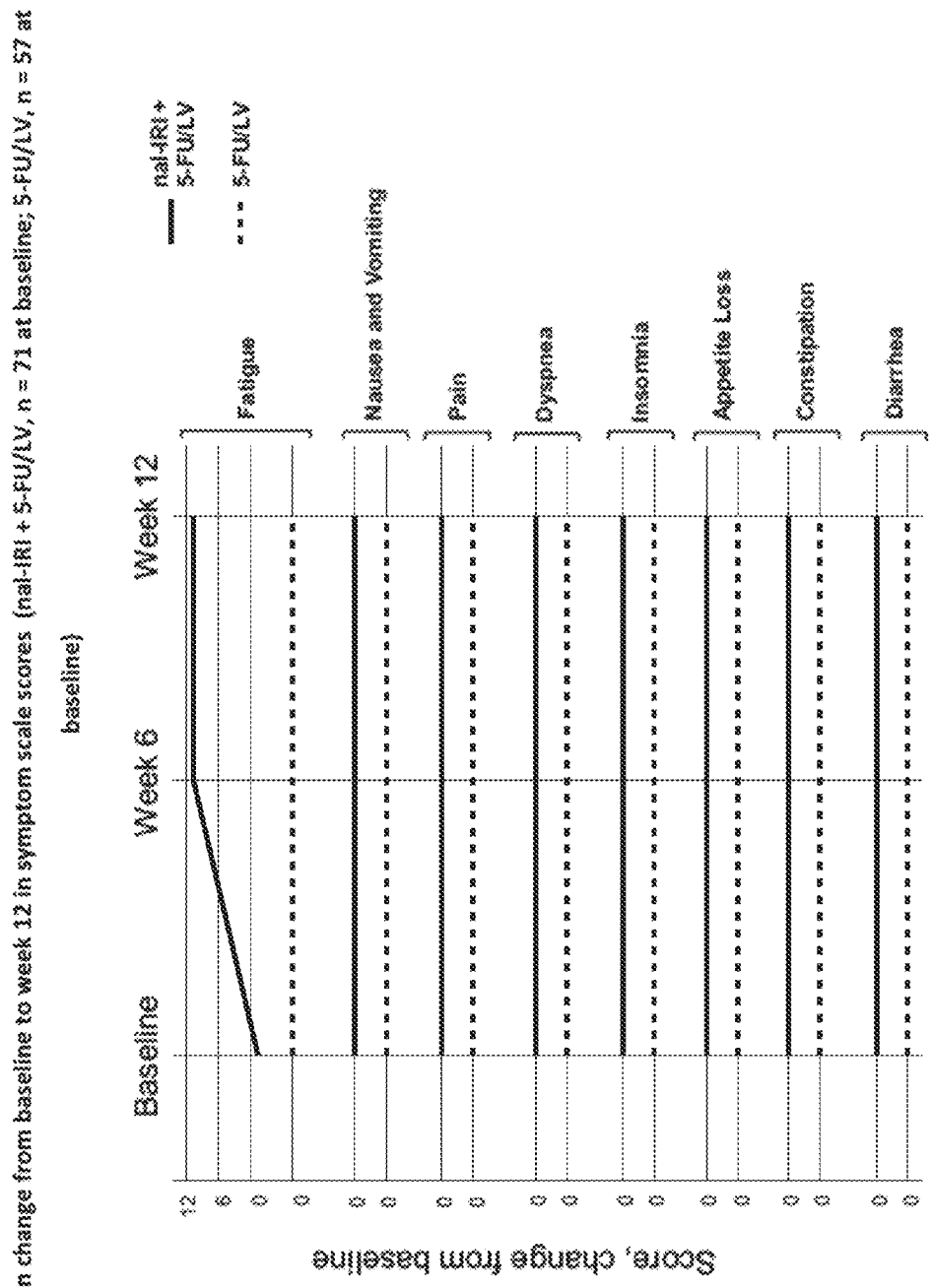
FIG. 29 is a graphical representation of the median change from baseline to week 12 in symptom scale scores (MM-398+5-FU/LV, n=71 at baseline; 5-FU/LV, n=57 at baseline).

After 378 events, MM-398+5-FU/LV retained an OS advantage relative to 5-FU/LV (Table 9 and FIG. 21A). With events in nearly all patients, the Kaplan-Meier OS curves converge at approximately 20 months, with 19 (16.2%) patients surviving beyond 20 months. No OS advantage was observed with MM-398 monotherapy versus 5-FU/LV (FIG. 21B). Median PFS was 3.1 months for MM-398+5-FU/LV versus 1.5 months for the 5-FU/LV combination control, and was 2.6 months for MM-398 monotherapy compared with 1.6 months for the 5-FU/LV monotherapy control (Table 9 and FIG. 22). ORR was higher than 5-FU/LV control for both MM-398+5-FU/LV (difference of 16% [95% CI, 9-24]) and MM-398 monotherapy (difference of 5% [95% CI, 1-9]; Table 9)

TABLE 9

Summary of the Updated Efficacy

| Endpoint | naI-IRI + 5-FU/LV (n = 117) | 5-FU/LV (n = 119) | Treatment effect* | naI-IRI (n = 151) | 5-FU/LV (n = 140) | Treatment effect* |
|---|---|---|---|---|---|---|
| median OS (95% CI), months | 6.2 (4.8-8.4) | 4.2 (3.3-5.3) | HR 0.75 P = 0.042 | 4.9 (4.2-5.6) | 4.2 (3.6-4.9) | HR 1.08 P = 0.513 |
| OS rate at 6 months (95% CI), % | 53 (44-62) | 38 (29-47) | — | | | — |
| OS rate at 12 months (95% CI), % | 26 (18-35) | 16 (10-24) | — | | | — |
| Median PFS (95% CI), months | 3.1 (2.7-4.2) | 1.5 (1.4-1.8) | HR 0.56 P < 0.001 | 2.7 (2.1-2.9) | 1.6 (1.4-1.8) | HR 0.81 P = 0.111 |
| ORR (95% CI), %[a] | 17 (10-24) | 1 (0-2) | P < 0.0001 | 6 (2-10) | 1 (0-2) | P = 0.020 |
| Best overall response, % | | | | | | |
| Partial response[b] | 17 | 1 | — | 6 | 1 | — |
| Stable disease[c] | 33 | 22 | — | 36 | 24 | — |
| Progressive disease | 29 | 47 | — | 34 | 48 | — |
| Other[d] | 3 | 2 | — | 2 | 1 | — |
| Not evaluable | 19 | 29 | — | 23 | 27 | — | naI-IRI, nanoliposomal irinotecan; 5-FU, 5-flurouracil; LV, leucovorin; OS, overall survival; CI, confidence interval; HR, hazard ratio; PFS, progression-free survival; ORR, objective response rate.
[a]Unstratified HR and log-rank P value.
[b]Designation of response did not require confirmation and was based solely on the investigator's assessment using RECIST v1.1 criteria.
[c]Minimum duration for stable disease from baseline is 6 weeks from the date of randomization.
[d]Patients without measurable (target) disease at baseline may have a best overall-response of non-complete response/non-partial response.

After 382 events, median OS was improved with MM-398+5-FU/LV vs 5-FU/LV (6.2 vs 4.2 mo; HR 0.75; 95% CI 0.57-0.99; P=0.038), but not for MM-398 vs 5-FU/LV (4.9 vs 4.2 mo; HR 1.07; 95% CI 0.84-1.36; P=0.567). Kaplan-Meier estimates of OS for MM-398+5-FU/LV and 5-FU/LV, respectively, were 53% and 38% at 6 mo, and 26% and 16% at 12 mo. Median progression-free survival was longer for MM-398+5-FU/LV vs 5-FU/LV (3.1 vs 1.5 mo; HR 0.57; 95% CI 0.43-0.76; P<0.001), but not for MM-398 vs 5-FU/LV (2.7 vs 1.6 mo; HR 0.81; 95% CI 0.63-1.04; P=0.111). Response rates per RECIST v1.1 were higher for MM-398+5-FU/LV vs 5-FU/LV (17% vs 1%; P<0.001) and for MM-398 vs 5-FU/LV (6% vs 1%; P=0.020). Grade ≥3 treatment-emergent adverse events in ≥10% of pts in either MM-398 arm were neutropenia (28%, 15%, and 1% in the MM-398+5-FU/LV, MM-398, and 5-FU/LV arms, respectively), fatigue (14%, 6%, and 4%), diarrhea (13%, 21%, and 5%), vomiting (12%, 14%, and 4%), anemia (9%, 11%, and 7%), and hypokalemia (3%, 12%, and 2%).

Safety and Tolerability Analysis of NAPOLI-1 Clinical Trial (Phase III)

Safety profile was manageable, with most frequent being grade ≥3 adverse events including neutropenia, fatigue and GI effects, such as diarrhea and vomiting (FIG. 17). The safety data described below are derived from NAPOLI-1. Serum bilirubin within the institutional normal range, albumin ≥3 g/dL, and Karnofsky Performance Status (KPS) ≥70 were required for study entry. The median duration of exposure was 9 weeks in the MM-398/5-FU/LV arm, 9 weeks in the MM-398 monotherapy arm, and 6 weeks in the 5-FU/LV arm. Neutropenia, diarrhea, nausea, and vomiting typically first occur early during the course of treatment with MM-398+5-FU/LV and tend to decrease in incidence and severity thereafter.

The most common adverse reactions (≥20%) of MM-398 were diarrhea, fatigue/asthenia, vomiting, nausea, decreased appetite, stomatitis, and pyrexia. The most common laboratory abnormalities (≥10% Grade 3 or 4) were lymphopenia and neutropenia. The most common serious adverse reactions (≥2%) of MM-398 were vomiting, diarrhea, neutropenic fever or sepsis, nausea, pyrexia, anemia, pneumonia, sepsis, dehydration, septic shock, acute renal failure, thrombocytopenia and ileus.

The most common adverse reactions (≥20%) of patients receiving MM-398 were diarrhea, fatigue/asthenia, vomiting, nausea, decreased appetite, stomatitis, and pyrexia. Severe (21%) or life-threatening (7%) neutropenia or neutropenic sepsis, of which 1% resulted in septic shock, occurred in patients receiving MM-398 in combination with 5-fluorouracil and leucovorin. In some embodiments, MM-398 is withheld from patients with an absolute neutrophil count below 1500/mm$^3$ or neutropenic fever. The blood cell counts of patients are preferably monitored periodically during treatment. Severe or life-threatening diarrhea occurred in 13% of patients receiving MM-398 in combination with 5FU and leucovorin.

Severe or life threatening neutropenia occurred in 27% of patients receiving MM-398/5-FU/LV compared to 2% of patients receiving 5-fluorouracil/leucovorin alone (5-FU/LV) in Study 1 described herein. The expected likelihood of severe or life threatening neutropenia (as a %) during treatment with MM-398/5-FU/LV in the protocol used in Study 1, is expressed by the parameter $P_{aen}$. In some embodiments, $P_{aen}$ is <50%. In some embodiments it is <45%, such as <40%, <35%, <30% or ≤27%.

In NAPOLI-1 study results, Grade 3 or 4 diarrhea occurred in 13% receiving MM-398/5-FU/LV compared to 4% receiving 5-FU/LV. The expected likelihood of Grade 3 or 4 diarrhea (as a %) during treatment with MM-398/5-FU/LV in the protocol used in Study 1, is expressed by the parameter $P_{aed}$. In some embodiments, $P_{aed}$ is <50%. In some embodiments it is <45%, such as <40%, <35%, <30%, <25%, <20%, <15% or ≤13%. In some embodiments, $t_{serv}$ is ≥6.1 months, $P_{aen}$ is ≤27% and $P_{aed}$ is ≤13%.

Adverse reactions led to permanent discontinuation of MM-398 in 11% of patients receiving MM-398/5-FU/LV; the most frequent adverse reactions resulting in discontinuation of MM-398 were diarrhea, vomiting, and sepsis. Dose reductions of MM-398 for adverse reactions occurred in 33% of patients receiving MM-398/5-FU/LV; the most frequent adverse reactions requiring dose reductions were neutropenia, diarrhea, nausea, and anemia. MM-398 was withheld or delayed for adverse reactions in 62% of patients receiving MM-398/5-FU/LV; the most frequent adverse reactions requiring interruption or delays were neutropenia, diarrhea, fatigue, vomiting, and thrombocytopenia.

Table 10 provides the frequency and severity of adverse reactions in Study 1 that occurred with higher incidence (≥5% difference for Grades 1-4 or ≥2% difference for Grades 3-4) in patients who received MM-398/5 FU/LV compared to patients who received 5-FU/LV arm.

TABLE 10

Adverse Reactions with Higher Incidence (≥5% Difference for Grades 1-4* or ≥2% Difference for Grades 3 and 4) in the MM-398/5-FU/LV.

| | MM-398/5-FU/LV N = 117 | | 5-FU/LV N = 134 | |
|---|---|---|---|---|
| Adverse Reaction | Grades 1-4 (%) | Grades 3-4 (%) | Grades 1-4 (%) | Grades 3-4 (%) |
| Gastrointestinal disorders | | | | |
| Diarrhea | 59 | 13 | 26 | 4 |
| Diarrhea, early† | 30 | 3 | 15 | 0 |
| Diarrhea, late‡ | 43 | 9 | 17 | 4 |
| Vomiting | 52 | 11 | 26 | 3 |
| Nausea | 51 | 8 | 34 | 4 |
| Stomatitis§ | 32 | 4 | 12 | 1 |
| Infections and infestations | | | | |
| Sepsis | 4 | 3 | 2 | 1 |
| Neutropenic fever/neutropenic sepsis♣ | 3 | 3 | 1 | 0 |
| Gastroenteritis | 3 | 3 | 0 | 0 |
| Device related infection | 3 | 3 | 0 | 0 |
| General disorders and administration site conditions | | | | |
| Fatigue/asthenia | 56 | 21 | 43 | 10 |
| Pyrexia | 23 | 2 | 11 | 1 |
| Metabolism and nutrition disorders | | | | |
| Decreased appetite | 44 | 4 | 32 | 2 |
| Weight loss | 17 | 2 | 7 | 0 |
| Dehydration | 8 | 4 | 7 | 2 |
| Skin and subcutaneous tissue disorders | | | | |
| Alopecia | 14 | 1 | 5 | 0 |

*NCI CTCAE v4.0
†Early diarrhea: onset within 24hours of MM-398 administration
‡Late diarrhea: onset >1 day after MM-398 administration
§Includes stomatitis, aphthous stomatitis, mouth ulceration, mucosal inflammation.
♣Includes febrile neutropenia.

398 pts were treated with MM-398+5-FU/LV (n=117), MM-398 (n=147), or 5-FU/LV (n=134). In the MM-398+5-FU/LV arm, most first occurrences of neutropenia, diarrhea, nausea, and vomiting were during the first 6 wk of treatment, with incidence and severity generally decreasing thereafter (Table 11). Similarly, prevalence and severity were highest in the first 6 wk and tended to decrease over time. Similar trends were observed in the MM-398 and 5-FU/LV arms.

TABLE 11

| Incidence, % | MM-398 + 5-FU/LV Period | | | MM-398 Period | | | 5-FU/LV Period | | |
|---|---|---|---|---|---|---|---|---|---|
| | 1 | 2 | 3 | 1 | 2 | 3 | 1 | 2 | 3 |
| Neutropenia grade | n = 117 | n = 73 | n = 34 | n = 147 | n = 95 | n = 43 | n = 134 | n = 111 | n = 43 |
| 1 | 1 | 3 | 3 | 1 | 2 | 0 | 1 | 0 | 0 |
| 2 | 8 | 3 | 3 | 8 | 3 | 0 | 1 | 2 | 2 |
| 3 | 14 | 4 | 9 | 5 | 1 | 0 | 2 | 0 | 0 |
| 4 | 7 | 0 | 0 | 6 | 2 | 0 | 0 | 0 | 0 |
| 5 | 0 | 0 | 0 | 0 | 0 | 0 | 0 | 0 | 0 |
| Diarrhea grade | n = 117 | n = 51 | n = 24 | n = 147 | n = 46 | n = 11 | n = 134 | n = 89 | n = 32 |
| 1 | 21 | 4 | 0 | 25 | 11 | 18 | 15 | 5 | 6 |
| 2 | 17 | 12 | 4 | 20 | 7 | 9 | 2 | 1 | 0 |
| 3 | 12 | 0 | 4 | 16 | 4 | 0 | 2 | 1 | 3 |
| 4 | 0 | 0 | 0 | 1 | 0 | 0 | 0 | 0 | 0 |
| 5 | 0 | 0 | 0 | 1 | 0 | 0 | 0 | 0 | 0 |
| Nausea grade | n = 117 | n = 56 | n = 28 | n = 147 | n = 53 | n = 25 | n = 134 | n = 87 | n = 26 |
| 1 | 21 | 5 | 7 | 23 | 4 | 8 | 19 | 4 | 12 |
| 2 | 16 | 0 | 7 | 27 | 4 | 8 | 5 | 4 | 4 |
| 3 | 7 | 2 | 0 | 5 | 2 | 0 | 2 | 2 | 0 |
| 4 | 0 | 0 | 0 | 0 | 0 | 0 | 0 | 0 | 0 |
| 5 | 0 | 0 | 0 | 0 | 0 | 0 | 0 | 0 | 0 |
| Vomiting grade | n = 117 | n = 61 | n = 35 | n = 147 | n = 61 | n = 28 | n = 134 | n = 89 | n = 29 |
| 1 | 19 | 5 | 11 | 27 | 2 | 7 | 16 | 2 | 4 |
| 2 | 14 | 0 | 9 | 10 | 3 | 4 | 5 | 1 | 4 |
| 3 | 10 | 0 | 3 | 12 | 2 | 0 | 1 | 1 | 4 |
| 4 | 0 | 0 | 0 | 0 | 0 | 0 | 0 | 0 | 0 |
| 5 | 0 | 0 | 0 | 0 | 0 | 0 | 0 | 0 | 0 |

Cholinergic Reactions:

MM-398 can cause cholinergic reactions manifesting as rhinitis, increased salivation, flushing, bradycardia, miosis, lacrimation, diaphoresis, and intestinal hyperperistalsis with abdominal cramping and early onset diarrhea. In Study 1, Grade 1 or 2 cholinergic symptoms other than early diarrhea occurred in 12 (4.5%) MM-398-treated patients. Six of these 12 patients received atropine; in 1 of the 6 patients who received atropine, the atropine was administered for cholinergic symptoms other than diarrhea.

Infusion Reactions:

Infusion reactions, consisting of allergic reaction, rash, urticaria, periorbital edema, or pruritus, occurring on the day of MM-398 administration were reported in 3% of patients receiving MM-398 or MM-398/5-FU/LV.

Additional clinically significant adverse reactions occurring in <10% of MM-398/5-FU/LV-treated patients were:

Cardiovascular:

Severe Hypotension

Laboratory abnormalities that occurred with higher incidence in the MM-398/5 FU/LV arm compared to the 5-FU/LV arm (≥5% difference) are summarized in the following table 12.

TABLE 12

Laboratory Abnormalities with Higher Incidence (≥5% Difference) in the MM-398/5-FU/LV Arm*#

| Laboratory abnormality | MM-398/5-FU/LV | | 5-FU/LV | |
|---|---|---|---|---|
| | Grades 1-4 (%) | Grades 3-4 (%) | Grades 1-4 (%) | Grades 3-4 (%) |
| Hematology | | | | |
| Anemia | 97 | 6 | 86 | 5 |
| Decreased lymphocytes | 81 | 27 | 75 | 17 |
| Decreased leukocytes | 67 | 16 | 20 | 0 |
| Decreased neutrophil counts | 52 | 20 | 6 | 2 |
| Decreased platelet counts | 41 | 2 | 33 | 0 |

TABLE 12-continued

Laboratory Abnormalities with Higher Incidence (≥5% Difference) in the MM-398/5-FU/LV Arm*#

| Laboratory abnormality | MM-398/5-FU/LV | | 5-FU/LV | |
|---|---|---|---|---|
| | Grades 1-4 (%) | Grades 3-4 (%) | Grades 1-4 (%) | Grades 3-4 (%) |
| Hepatic | | | | |
| Increased alanine aminotransferase (ALT) | 51 | 6 | 37 | 1 |
| Decreased albumin | 43 | 2 | 30 | 0 |
| Metabolic | | | | |
| Decreased magnesium | 35 | 0 | 21 | 0 |
| Decreased potassium | 32 | 2 | 19 | 2 |
| Decreased calcium | 32 | 1 | 20 | 0 |
| Decreased phosphate | 29 | 4 | 18 | 1 |
| Decreased sodium | 27 | 5 | 12 | 3 |
| Renal | | | | |
| Increased creatinine | 18 | 0 | 13 | 0 |

*NCI CTCAE v4.0, worst grade shown
Percent based on number of patients with a baseline and at least one post-baseline measurement.

Of the 264 patients who received MM-398 as a single agent or in combination with 5-FU and leucovorin in Study 1, 49% were ≥65 years old and 13% were ≥75 years old. No overall differences in safety and effectiveness were observed between these patients and younger patients.

The safety profiles of MM-398+5-FU/LV and MM-398 monotherapy described in the current updated analysis did not change appreciably from that reported in the primary analysis. The most frequently reported grade ≥3 TEAEs in the MM-398—containing arms were neutropenia, diarrhea, vomiting, and fatigue (Table 13). TEAEs led to dose delay, reduction, and/or discontinuation in 73% of patients in the MM-398+5-FU/LV arm, 56% of patients in the MM-398 monotherapy arm, and 37% of patients in the 5-FU/LV arm. The most common reasons for dose reduction in the MM-398+5-FU/LV and MM-398 monotherapy arms were gastrointestinal events (12% and 17%, respectively) and neutropenia (18% and 10%). The rate of treatment discontinuation due to a TEAE was 12% with MM-398+5-FU/LV, 14% with MM-398, and 8% with 5-FU/LV; neutropenia, diarrhea, and vomiting were the most common reasons for discontinuation in the MM-398-containing arms. Grade ≥3 febrile neutropenia occurred in 2 (2%) patients receiving MM-398+5-FU/LV and 6 (4%) patients receiving MM-398; 1 and 5 patients, respectively, required a dose reduction but no patient discontinued treatment due to febrile neutropenia. No additional deaths due to treatment-related TEAEs have been reported since the primary analysis.

TABLE 13

Grade ≥3 TEAE (Treatment Emergent Adverse Event), %

| Grade ≥3 TEAE, % | naI-IRI + 5-FU/LV (n = 117) | naI-IRI monotherapy (n = 151) | 5-FU/LV (n = 134) |
|---|---|---|---|
| Any TEAE | 80 | 76 | 56 |
| Neutropenia$^a$ | 28 | 15 | 2 |
| Fatigue | 14 | 6 | 4 |
| Diarrhea | 13 | 21 | 5 |
| Vomiting | 12 | 14 | 4 |
| Anemia | 9 | 11 | 7 |
| Asthenia | 8 | 7 | 7 |
| Nausea | 8 | 5 | 3 |
| White blood cell count decreased | 8 | 3 | 0 |
| Abdominal pain | 7 | 8 | 7 |
| Decreased appetite | 5 | 9 | 2 |
| Hypokalemia | 3 | 12 | 2 |
| Hyponatremia | 3 | 6 | 2 |
| Hyperglycemia | 2 | 5 | 2 |

TEAE, treatment-emergent adverse event; MM-398, nanoliposomal irinotecan; 5-FU, 5-fluorouracil; LV, leucovorin. The tabel includes all grade ≥3 TEAEs reproted for ≥5% of patients in any treatment arm.
$^a$Neutropenia includes agranulocytosis, febrile neutropenia, granulocytopenia, neutropenia, neutropenic sepsis, decreased neutrophil count, and pancytopenia.

The most common grade ≥3 treatment-emergent adverse events (TEAEs) in the MM-398+5-FU/LV arm were neutropenia, fatigue, diarrhea, and vomiting. Based on NAPOLI-1, the MM-398+5-FU/LV regimen received regulatory approval from the US Food and Drug Administration for the treatment of patients with metastatic adenocarcinoma of the pancreas after disease progression following gemcitabine-based therapy. Here, we present results of a prespecified safety analysis by patient subgroup from NAPOLI-1.

TEAEs were graded by NCI CTCAE v4.0 and coded by MedDRA v14.1 for the following prespecified subgroups: sex, age (<65 vs ≥65 years), ethnicity (white vs Asian), UGT1A1*28 status, prior conventional irinotecan therapy (yes vs no), and prior 5-FU therapy (yes vs no). All TEAEs were followed until resolution or patient discontinuation. Analyses were performed on the safety population (ie, those who received ≥1 dose of study medication). Results herein are for the MM-398+5-FU/LV arm unless otherwise noted.

Overall, the incidence and severity of TEAEs were similar between men (n=67) and women (n=50). Patients aged ≥65 years (n=54) generally had a higher incidence of TEAEs than those <65 years (n=63) (eg, stomatitis: 20.4% vs 7.9%; anemia: 46.3% vs 30.2%), although the most common types of TEAEs were similar regardless of age. Overall, Asian (n=33) patients had a higher incidence of grade ≥3 TEAEs than white (n=73) patients (87.9% vs 69.9%), primarily because of an increased incidence of neutropenia (24.2% vs 12.3%) and decreased neutrophil counts (33.3% vs 1.4%); febrile neutropenia was reported in 3.0% of Asian patients and 0 white patients. Gastrointestinal disorders also occurred slightly more frequently in Asian patients than white patients (any grade: 100% vs 87.7%), although diarrhea was less frequent and less severe among Asian patients (any grade: 48.5% vs 61.6%; grade ≥3: 3.0% vs 19.2%). The UGT1A1 gene encodes an enzyme responsible for glucuronidation of the active metabolite of irinotecan, SN-38. Patients homozygous for the UGT1A1*28 allele (UGT1A1 7/7 genotype) may be at increased risk for neutropenia during irinotecan treatment due to reduced glucuronidation of SN-38. However, in this analysis, there were no differences in incidence, type, and severity of TEAEs between patients homozygous (n=7) for the UGT1A1*28 allele and those who were not (n=110). There were also no notable differences in the incidence or severity of TEAEs between patients with (n=12) and without (n=105) prior conventional irinotecan therapy, or between patients with (n=50) or without (n=67) prior 5-FU therapy.

Overall, the safety profile of MM-398+5-FU/LV was generally similar across patient subgroups, apart from an increased risk of grade ≥3 neutropenia/reduced neutrophil counts in Asian patients. The results of this prespecified subgroup analysis further support the tolerability profile of MM-398+5-FU/LV in patients with mPAC previously treated with gemcitabine-based therapy.

The median overall survival (OS) increased significantly with MM-398+5-FU/LV relative to 5-FU/LV (6.1 vs 4.2 months; unstratified hazard ratio [HR], 0.67 [95% confidence interval (CI), 0.49-0.92]; P=0.012), but did not differ significantly between MM-398 monotherapy and 5-FU/LV (4.9 vs 4.2 months; unstratified HR 0.99 [95% CI, 0.77-1.28]; P=0.94).

Adverse events that resulted in a dose reduction occurred in 39 (33%) patients in the MM-398+5-FU/LV arm, 46 (31%) patients in the MM-398 monotherapy arm, and 5 (4%) patients in the 5-FU/LV arm. Adverse events leading to treatment discontinuation occurred in 13 (11%) patients in the MM-398+5-FU/LV arm, 17 (12%) patients in the MM-398 monotherapy arm, and 10 (7%) patients in the 5-FU/LV arm.

Patients were initially randomized to MM-398 monotherapy (120 mg/m$^2$ irinotecan hydrochloride trihydrate salt equivalent to 100 mg/m$^2$ irinotecan free base every 3 weeks) or 5-FU/LV (200 mg/m$^2$ LV and 2000 mg/m$^2$ 5-FU, every week for the first 4 weeks of each 6-week cycle). Once safety data for the combination regimen became available from a concurrent study in metastatic colorectal cancer, the protocol was amended to include a third arm, MM-398+5-FU/LV (80 mg/m$^2$ irinotecan hydrochloride trihydrate salt [equivalent to 70 mg/m$^2$ irinotecan free base], 400 mg/m$^2$ LV, and 2400 mg/m$^2$ 5-FU over 46 hours, every 2 weeks).

The initial MM-398 dose in the MM-398+5-FU/LV arm was 60 mg/m$^2$ (salt) for patients homozygous for the UGT1A1*28 allele (TA7/TA7 genotype) and could be increased to the standard dose (80 mg/m$^2$ (salt)) in the absence of drug-related toxic effects. Randomization was stratified by baseline albumin levels (≥4.0 g/dL vs <4.0 g/dL) KPS (70 and 80 vs ≥90), and ethnicity (white vs east Asian vs all others).

TEAEs were graded by National Cancer Institute Common Terminology Criteria for Adverse Events, version 4.0, and coded by Medical Dictionary for Regulatory Activities, version 14.1. All TEAEs were followed until resolution or patient discontinuation. The safety analysis population included all patients who received ≥1 dose of study drug. The presence of the UGT1A1*28 allele was determined by genotype testing, and homozygous patients were identified (A7/TA7 genotype)

Eligibility Criteria:

Key Inclusion Criteria: Adults ≥18 years of age; Histologically or cytologically confirmed PDAC; Documented measurable or nonmeasurable distant metastatic disease (as defined by Response Evaluation Criteria in Solid Tumors, version 1.1); Disease progression after prior gemcitabine or gemcitabine-containing therapy in a neoadjuvant, adjuvant (only if distant metastases occurred within 6 months of completing adjuvant therapy), locally advanced, or metastatic setting; KPS score ≥70; Adequate hematologic (including absolute neutrophil count >1.5×109 cells/L), hepatic (including normal serum total bilirubin and albumin levels ≥30 g/L), and renal function.

Key Exclusion Criteria: Active central nervous system metastasis; Clinically significant gastrointestinal disorder; Severe arterial thromboembolic events <6 months before inclusion; New York Heart Association class III or IV congestive heart failure, ventricular arrhythmias, or uncontrolled blood pressure; Active infection or uncontrolled fever.

Of the 417 patients included in the intention-to-treat population, 398 (95%) received ≥1 dose of any study drug (safety analysis population).

Median duration of exposure to MM-398 in the MM-398 combination arm was 8.7 weeks (interquartile range [IQR], 5.4-22.0 weeks); mean dose intensity of MM-398 over 6 weeks was 167.5 mg/m$^2$ (standard deviation [SD], 52.05 mg/m$^2$). Median duration of exposure to 5-FU was 8.7 weeks (IQR, 5.4-22.0 weeks) in the MM-398 combination arm and 6.0 weeks (IQR, 5.9-12.1 weeks) in the control arm; mean dose intensities of 5-FU over 6 weeks were 5065.0 mg/m$^2$ (SD, 1539.1 mg/m$^2$) and 6718.0 mg/m$^2$ (SD, 1770.18 mg/m$^2$), respectively.

Incidence of any-grade and grade ≥3 TEAEs was similar between patients aged <65 years and those aged ≥65 years in each treatment arm. Grade ≥3 TEAEs of note (difference of ≥5% between subgroups): In the MM-398 combination arm, incidence of vomiting (14.3% vs 7.4%) was higher in patients <65 years; incidence of nausea (11.1% vs 4.8%) was higher in patients ≥65 years.

Incidence of any-grade TEAEs was similar between white and east Asian patients in each treatment arm, with the exception of diarrhea, which occurred less frequently in east Asians. Incidence of grade ≥3 TEAEs in the control arm was similar between white and east Asian patients (56.5% vs 54.5%), whereas the incidence of grade ≥3 TEAEs in the MM-398 combination arm was higher for east Asians compared with whites (87.9% vs 69.9%). Grade ≥3 TEAEs of note (difference of ≥5% between subgroups). In the MM-398 combination arm, incidence of diarrhea (19.2% vs 3.0%), fatigue (19.2% vs 0%), and vomiting (13.7% vs 6.1%) was higher in white patients; incidence of anemia (21.2% vs 5.5%), neutropenia (54.5% vs 17.8%), and white blood cell decrease (21.2% vs 2.7%) was higher in east Asian patients. In the control arm, incidence of abdominal pain (8.2% vs 2.3%) was higher in white patients; incidence of anemia (13.6% vs 3.5%) was higher in east Asian patients.

UGT1A1*28 Allele (TA7/TA7 Genotype): Although the low number of patients with the TA7/TA7 genotype makes comparison difficult the incidence of any-grade and grade ≥3 TEAEs appeared to be similar between patients with or without the TA7/TA7 genotype. In the MM-398 combination arm, 3 of the 7 patients with the TA7/TA7 genotype were able to escalate the MM-398 dose to 80 mg/m$^2$ without needing dose reduction. 1 patient escalated but required dose reduction back to 60 mg/m$^2$; 2 patients maintained the initial dose; 1 patient required dose reduction to 40 mg/m$^2$; 1 additional patient in the MM-398 combination arm with the TA7/TA7 genotype discontinued treatment (without dose reduction) because of grade 3 vomiting. Incidence of any-grade and grade ≥3 TEAEs was similar between patients with albumin levels ≥4.0 g/dL or <4.0 g/dL. Grade ≥3 TEAEs of note (difference of ≥5% between subgroups). In the MM-398 combination arm, incidence of diarrhea (17.6% vs 6.4%) and fatigue (16.2% vs 10.6%) was higher in patients with albumin levels ≥4.0 g/dL. In the control arm, incidence of diarrhea (8.1% vs 1.4%) was higher in patients with albumin levels <4.0 g/dL.

Karnofsky Performance Status: Incidence of any-grade TEAEs was similar between patients with KPS score of ≥90 or <90. Incidence of grade ≥3 TEAEs was similar between patients with KPS score of ≥90 or <90 in the MM-398 combination arm; incidence of grade ≥3 TEAEs was lower in patients with KPS score of ≥90 vs patients with KPS score of <90 in the control arm (40.9% vs 70.6%). Grade ≥3 TEAEs of note (difference of ≥5% between subgroups): In the MM-398 combination arm, incidence of decreased appetite (8.3% vs 1.4%) and abdominal pain (10.4% vs 4.3%) was higher in patients with KPS score <90; In the control arm, incidence of abdominal pain (8.8% vs 3.0%) was higher in patients with KPS score <90.

Patient Quality of Life Evaluation

Patients with mPDAC frequently experience a significant symptom burden. This in turn negatively impacts their QoL. QoL was a secondary endpoint of the study.

QoL was assessed using the European Organization for Research and Treatment of Cancer quality-of-life core questionnaire (EORTC-QLQ-C30), which includes functional scales (physical, role, cognitive, emotional, and social); symptom scales (appetite loss, constipation, diarrhea, dyspnea, fatigue, insomnia, nausea and vomiting, and pain); and a global health and quality-of-life scale. Patients were to complete the questionnaire at treatment start, every 6 weeks, and 30 days post-follow-up visit. The population analyzed included all patients who provided baseline and at ≥1 subsequent EORTC-QLQ-C30 assessment. Linear transformations were applied to the raw scores to produce reported scores in the 0-100 range. In the responder analysis, patients were classified as improved (≥10% increase in scale of breadth at a post-baseline time point and remained above baseline for ≥6 weeks), worsened (did not meet improvement criteria and died, or had ≥10% decrease from baseline in scale of breadth at a post-baseline time point), or stable (did not meet criteria for improvement or worsening) for each subscale. Pairwise treatment group comparisons on response classification were performed for each subscale using Cochran-Mantel-Haenszel testing adjusted for multiplicity with a Benjamini-Hochberg correction to control false discovery rate at 0.05 level for the 15 comparisons.

A total of 154 patients (MM-398+5-FU/LV, n=71; 5-FU/LV, n=83) comprised the population for this analysis of which 69% (49/71) of patients in the MM-398+5-FU group and 53% (44/83) in the 5-FU/LV group had evaluable data at 12 weeks. At baseline, median Global Health Status scores were near the midpoint of the scoring range, median Functional Scale scores were high, and Symptom Scale scores were low, with baseline values similar between groups. The observed median change in score at 12 weeks was 0 for both treatment groups for Global Health Status and for the following subscale scores: role functioning, emotional functioning, cognitive functioning, social functioning, nausea and vomiting, pain, dyspnea, insomnia, appetite loss, constipation, diarrhea, and financial difficulties. For subscale scores for which the median change was not 0 (MM-398+ 5-FU/LV: physical functioning and fatigue), the between-group differences were not substantial. Additionally, there were no significant differences in the proportion of patients classified as improved, worsened, or stable between the treatment groups. Across subscales, adjusted P values for the comparisons were >0.05 (NS).

In NAPOLI-1, evaluable MM-398+5-FU/LV-treated patients with data through 12 weeks tended to maintain baseline QoL over 12 weeks, and there were no significant differences versus the 5-FU/LV-treated patients in QoL response despite the addition of a second cytotoxic agent. These results are limited by the small number of patients and variability in QoL subscale scores.

The median overall survival (OS) increased significantly with MM-398+5-FU/V relative to 5-FU/LV (6.1 vs 4.2 months; unstratified hazard ratio [HR], 0.67 [95% confidence interval (CI), 0.49-0.92]; P=0.012), but did not differ significantly between MM-398 monotherapy and 5-FU/LV (4.9 vs 4.2 months; unstratified HR 0.99 [95% CI, 0.77-1.28]; P=0.94).

Median PFS was significantly longer with MM-398+5-FU/V compared with 5-FU/LV (3.1 vs 1.5 months; unstratified HR 0.56; 95% CI, 0.41-0.75; P=0.0001).

Median ORR was significantly higher with MM-398+5-FU/V compared with 5-FU/LV (16% vs 1%; P<0.0001).

MM-398+5-FU/LV exhibited a manageable safety profile; grade 3/4 adverse events (AEs) occurring more frequently with MM-398+5-FU/LV vs 5-FU/LV included neutropenia (27% vs 1%), fatigue (14% vs 4%), diarrhea (13% vs 4%), and vomiting (11% vs 3%). 71 patients (61% of the ITT population randomized under protocol version 2) in the MM-398+5-FU/LV arm and 57 patients (48% of the ITT population randomized under protocol version 2) in the 5-FU/LV arm provided baseline and ≥1 subsequent EORTC assessment (PRO population). Patient demographics and baseline characteristics were similar between the treatment arms. No substantial differences were identified in the proportion of patients exhibiting improved, stable, or worsening QoL in symptom scale scores between the MM-398+5-FU/LV and 5-FU/LV arms.

Baseline global health status and functional scale scores ranged from 58-83 and were similar between the treatment arms. Overall, there were no appreciable changes from baseline in global health status and functional scale scores between the MM-398+5-FU/LV and 5-FU/LV arms. The observed median change from baseline to week 6 in physical functioning score was 6.7 points in both arms; which corresponds to "a little" decrease. Baseline symptom scale scores ranged from 0-33 and were similar between the treatment arms. Overall, there were no appreciable changes from baseline in symptom scale scores between the MM-398+5-FU/LV and 5-FU/LV arms. The observed median change from baseline to week 6 in fatigue score was approximately 11 points in the MM-398+5-FU/LV arm, which corresponds to a "moderate" increase.

MM-398+5-FU/LV significantly improves OS in patients with mPDAC previously treated with gemcitabine-based therapy compared with 5-FU/LV. Global health status and functional scale scores were not significantly different between treatment arms at baseline, and showed no appreciable change over 12 weeks. Median symptom scale scores at baseline ranged from 0-33 (low levels of symptomatology), and showed no appreciable change over 12 weeks. MM-398+5-FU/LV provides a new treatment option that does not compromise QoL in patients with mPDAC previously treated with gemcitabine-based therapy.

Endnotes

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features set forth herein. The disclosure of each and every US, international, or other patent or patent application or publication referred to herein is hereby incorporated herein by reference in its entirety.

What is claimed is:

1. A method of treating patients with metastatic adenocarcinoma of the pancreas after disease progression following gemcitabine-based therapy who are not homozygous for the UTG1A1*28 allele, the method comprising intravenously administering to the patient in need thereof an antineoplastic therapy once every two weeks, the antineoplastic therapy consisting of:
   a. administering liposomal irinotecan as an intravenous infusion in an amount providing 70 mg/m$^2$ of irinotecan free base, the liposomal irinotecan composition comprising irinotecan encapsulated in irinotecan liposomes having a diameter of approximately 110 nm and an irinotecan terminal elimination half-life in the patient of 25.8 hours;
   b. 200 mg/m$^2$ of the (l) form of leucovorin; and
   c. 2,400 mg/m$^2$ of 5-fluorouracil.

2. The method of claim 1, wherein liposomal irinotecan has an area under the plasma concentration curve extrapolated to time infinity ($AUC_{0-\infty}$) of 1091-1705 [h·µg/mL].

3. The method of claim 1, wherein liposomal irinotecan has an area under the plasma concentration curve extrapolated to time infinity ($AUC_{0-\infty}$) of 1364 [h·µg/mL].

4. The method of claim 1, wherein liposomal irinotecan has a maximum plasma concentration of 29-47 micrograms/mL.

5. The method of claim 1, wherein liposomal irinotecan has a maximum plasma concentration of 37 micrograms/mL.

6. The method of claim 1, wherein the irinotecan liposomes are unilamellar lipid bilayer vesicles comprising phosphatidylcholine, cholesterol, and a polyethyleneglycol-derivatized phosphatidyl-ethanolamine.

7. The method of claim 1, wherein the irinotecan liposomes are approximately 110 nm in diameter.

8. The method of claim 1, wherein the irinotecan liposomes encapsulate an aqueous space containing irinotecan in a gelated or precipitated state as the sucrose octasulfate salt.

9. The method of claim 1, wherein the liposomal irinotecan comprises 1,2-distearoyl-sn-glycero-3-phosphocholine (DSPC), cholesterol, and methoxy-terminated polyethylene glycol (MW 2000)-distearoylphosphatidyl ethanolamine (MPEG-2000-DSPE).

10. The method of claim 1, wherein the 200 mg/m$^2$ of the (l) form of leucovorin is provided by administering 400 mg/m$^2$ of the (l+d) form of leucovorin.

11. A method of treating patients with metastatic adenocarcinoma of the pancreas after disease progression following gemcitabine-based therapy who are not homozygous for the UTG1A1*28 allele, the method comprising intravenously administering to the patient in need thereof an antineoplastic therapy once every two weeks, the antineoplastic therapy consisting of:

a. administering liposomal irinotecan as an intravenous infusion over 90 minutes in an amount providing 70 mg/m² of irinotecan free base, the liposomal irinotecan composition comprising irinotecan encapsulated in irinotecan liposomes having an area under the plasma concentration curve extrapolated to time infinity ($AUC_{0-\infty}$) of about 1091-1705 [h·µg/mL]; followed by
b. 200 mg/m² of the (l) form of leucovorin; and
c. 2,400 mg/m² of 5-fluorouracil.

12. The method of claim 11, wherein the irinotecan liposomes have a diameter of approximately 110 nm and comprise phosphatidylcholine, cholesterol, and a polyethyleneglycol-derivatized phosphatidyl-ethanolamine.

13. The method of claim 11, wherein the 200 mg/m² of the (l) form of leucovorin is provided by administering 400 mg/m² of the (l+d) form of leucovorin.

14. The method of claim 11, wherein liposomal irinotecan has a maximum plasma concentration of about 29-47 micrograms/mL.

15. The method of claim 11, wherein the irinotecan liposomes encapsulate an aqueous space containing irinotecan in a gelated or precipitated state as the sucrose octasulfate salt.

16. A method of treating pancreatic cancer in a human patient who has previously been treated with gemcitabine, the method comprising intravenously administering to the patient in need thereof an antineoplastic therapy once every two weeks, the antineoplastic therapy consisting of: a single dose of 70 mg/m² of irinotecan free base in an irinotecan nanoparticle composition comprising irinotecan nanoparticles having a diameter of 80-140 nm, administered in combination with 200 mg/m² of the (l) form of leucovorin and 2,400 mg/m² of 5-fluorouracil, to treat the pancreatic cancer in the human patient, wherein the irinotecan nanoparticle composition has one or more characteristics selected from the group consisting of:
    a. an area under the plasma concentration curve extrapolated to time infinity ($AUC_{0-28}$) of about 1091-1705 [h·µh/mL]; and
    b. a maximum plasma concentration of about 29-47 micrograms/mL.

17. The method of claim 16, wherein the irinotecan liposome has an irinotecan terminal elimination half-life in the patient of at least about 2-fold higher than that of 125 mg/m² free irinotecan as CPT-11 irinotecan hydrochloride injection.

18. The method of claim 16, wherein the irinotecan nanoparticles comprise irinotecan encapsulated in a unilamellar lipid bilayer vesicle composed of phosphatidylcholine, cholesterol, and a polyethyleneglycol-derivatized phosphatidyl-ethanolamine, and the 200 mg/m² of the (l) form of leucovorin is provided by administering 400 mg/m² of the (l+d) form of leucovorin.

19. The method of claim 16, wherein the irinotecan nanoparticle composition has an irinotecan terminal elimination half-life in the patient of about 25.8 hours.

20. The method of claim 16, wherein the irinotecan is converted to SN-38 within the human patient and the AUC of the SN-38 increases less than proportionally with the dose of the liposomal irinotecan.

21. A method of treating patients with metastatic adenocarcinoma of the pancreas after disease progression following gemcitabine-based therapy, the method comprising intravenously administering to the patient in need thereof an antineoplastic therapy once every two weeks, the antineoplastic therapy consisting of: an intravenous infusion of liposomal irinotecan in an amount providing a total of 70 mg/m² of irinotecan free base, in combination with therapeutically effective amounts of 5-fluorouracil and leucovorin.

22. The method of claim 21, wherein the patient is not homozygous for the UTG1A1*28 allele and the liposomal irinotecan comprises irinotecan encapsulated in irinotecan liposomes having a diameter of approximately 110 nm and an irinotecan terminal elimination half life in the patient of 25.8 hours.

23. The method of claim 22, wherein each intravenous infusion of liposomal irinotecan is administered over 90 minutes.

24. The method of claim 23, wherein
    a. the irinotecan liposomes encapsulate an aqueous space containing irinotecan in a gelated or precipitated state as the sucrose octasulfate salt; and
    b. the liposomal irinotecan comprises 1,2-distearoyl-sn-glycero-3-phosphocholine (DSPC), cholesterol, and methoxy-terminated polyethylene glycol (MW 2000)-distearoylphosphatidyl ethanolamine (MPEG-2000-DSPE).

* * * * *

UNITED STATES PATENT AND TRADEMARK OFFICE
CERTIFICATE OF CORRECTION

PATENT NO. : 9,717,724 B2  
APPLICATION NO. : 15/241128  
DATED : August 1, 2017  
INVENTOR(S) : Eliel Bayever et al.

Page 1 of 1

It is certified that error appears in the above-identified patent and that said Letters Patent is hereby corrected as shown below:

On the Title Page

In the Related U.S. Application Data, "Continuation-in-part of application No. 14/406,776, filed as application No. PCT/US2013/045495 on Jun. 12, 2013, now Pat. No. 9,452,162." should read "Continuation-in-part of Application No. 14/406,776, filed Dec. 10, 2014, now Pat. No. 9,452,162 which is a §371 national stage entry of PCT/US2013/045495, filed Jun. 12, 2013.".

In the Claims

Column 41, Line 38, in Claim 16, delete "$(AUC_{0\_28})$" and replace with "$(AUC_{0-\infty})$".

Column 41, Line 39, in Claim 16, delete "[h· µh/mL]" and replace with "[h· µg/mL]".

Signed and Sealed this  
Tenth Day of April, 2018

Andrei Iancu  
*Director of the United States Patent and Trademark Office*